United States Patent [19]

Spatz et al.

[11] 4,289,903

[45] Sep. 15, 1981

[54] PARA-PHENYLALKOXY PHENYLUREA AND THIOUREA COMPOUNDS AND HERBICIDAL USE THEREOF

[75] Inventors: David M. Spatz, Trenton; Barrington Cross, Rocky Hill, both of N.J.

[73] Assignee: American Cyanamid Company, Stamford, Conn.

[21] Appl. No.: 51,584

[22] Filed: Jun. 25, 1979

[51] Int. Cl.$^3$ .................. C07C 127/15; C07C 127/17; A01N 7/00; A01N 17/08

[52] U.S. Cl. ......................................... 564/20; 71/88; 71/99; 71/105; 71/107; 71/119; 71/120; 260/465 E; 260/340.9 R; 560/11; 560/13; 560/16; 560/18; 560/39; 560/251; 560/138; 560/22; 564/27; 564/28; 564/29; 564/49; 564/50; 564/51; 564/52; 564/53

[58] Field of Search ............ 260/552 R, 553 A, 465 E

[56] References Cited

U.S. PATENT DOCUMENTS

| | | | |
|---|---|---|---|
| 3,912,489 | 10/1975 | Fischer | 71/91 |
| 4,013,450 | 3/1977 | Olin et al. | 71/99 |
| 4,058,392 | 11/1977 | Thomas et al. | 260/553 A |
| 4,129,435 | 12/1978 | Takematsu et al. | 71/120 |
| 4,129,436 | 12/1978 | Takemoto et al. | 71/120 |

*Primary Examiner*—Donald G. Daus
*Assistant Examiner*—James H. Turnipseed
*Attorney, Agent, or Firm*—Harry H. Kline

[57] ABSTRACT

There are provided certain p-phenylalkoxy phenylurea and thiourea compounds useful for the control of undesirable plants in the presence of agronomic crops and to methods for the preparation of said phenylalkoxy phenylurea and thiourea compounds.

18 Claims, No Drawings

PARA-PHENYLALKOXY PHENYLUREA AND THIOUREA COMPOUNDS AND HERBICIDAL USE THEREOF

SUMMARY OF THE INVENTION

The present invention relates to herbicidal urea compounds of formula (I):

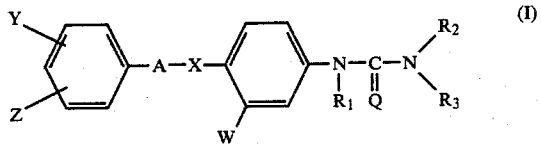

wherein X is selected from O,S,SO and $SO_2$; Q is O or S; Y is selected from the group consisting of hydrogen, halogen, HO, $C_1-C_4$ alkoxy, $C_2-C_5$ alkenyl, $C_2-C_5$ alkynyl, CN, $CF_3$, $CH_3S$, $CH_3O_2S$, $NO_2$, $C_1-C_4$ alkylamino, NHCHO, $NH_2$,

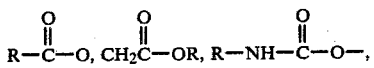

$CH_2=CHCH_2O$, $CH\equiv C-CH_2O$, $CF_2HO$, $CF_3O$, and $CF_2ClO$; Z is selected from hydrogen, halogen, $C_1-C_4$ alkyl, $C_1-C_4$ alkoxy, $CF_3$ and $NO_2$; A represents a $C_2-C_8$ carbon chain which may be saturated or unsaturated, and is optionally either monosubstituted with $C_1-C_3$ alkyl, $C_1-C_3$ alkoxy, halogen, CN, $CF_3$, $CH_3S$, OH, O, $NO_2$, $NH_2$, di($C_1-C_3$) alkylamino, $CH_3SO_2$,

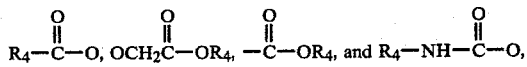

or is optionally disubstituted wherein the second substituent is selected from $C_1-C_3$ alkyl and halogen; or A is a moiety represented by formula:

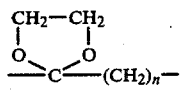

wherein n is an integer of from 1 to 7; R is $C_1-C_4$ alkyl; $R_1$ is selected from hydrogen, $CH_3$ and CHO; $R_2$ is selected from $C_1-C_4$ alkyl optionally substituted with $C_1-C_3$ alkoxy or halogen, $C_3-C_5$ alkenyl and $C_3-C_5$ alkynyl; $R_3$ is selected from hydrogen, $C_1-C_4$ alkyl optionally substituted with $C_1-C_3$ alkoxy or halogen, $C_3-C_5$ alkenyl, $C_3-C_5$ alkynyl and CHO; with the proviso that one of $R_1$, $R_2$ and $R_3$ must be selected from hydrogen or CHO; $R_4$ is $C_1-C_3$ alkyl; W is selected from hydrogen, halogen, $C_1-C_4$ alkyl, $C_1-C_4$ alkoxy, $CH_3S$, $CH_3O_2S$, CN, $NO_2$, $(CH_3)_2N$, $CF_3$, $CF_3O_2S$, $COOC_2H_5$ and $CF_2HO_2S$.

A preferred group of compounds of formula (I) are those wherein X is selected from O and S; Q is O or S; Y and Z each are selected from the group consisting of hydrogen, Cl, F, $C_1-C_4$ alkyl, $C_1-C_4$ alkoxy and $NO_2$; A is a $C_2-C_5$ carbon chain saturated or unsaturated and optionally monosubstituted with Br, Cl, F, $CH_3$, $CH_3O$, O,OH, $NH_2$ di($C_1-C_2$) alkylamino and NHCHO, or is optionally disubstituted, wherein the second substituent is selected from $CH_3$ or halogen, or A is a moiety selected from

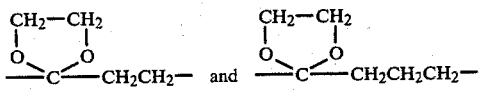

$R_1$ is hydrogen and CHO; $R_2$ is selected from $C_1-C_2$ alkyl, $C_3-C_5$ alkenyl, $C_3-C_4$ alkynyl and $C_2H_4OC_2H_5$; $R_3$ is selected from hydrogen, $C_1-C_2$ alkyl and CHO; W is selected from $CH_3$, $CH_3O$, $CF_3$, CN, Br, Cl, F, I, $NO_2$ and $CH_3S$.

Three more (equally) preferred groups of compounds of formula (I) can be represented by formula (Ia) below:

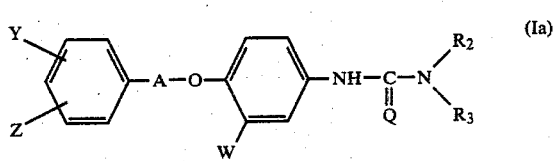

wherein in one of these preferred groups Y and Z each are selected from hydrogen, $CH_3$, Cl and F; A is a $C_2-C_3$ saturated alkylene chain having an optional $CH_3$ branch; $R_2$ is selected from hydrogen, $CH_3$ and $C_2H_5$; $R_3$ is selected from $CH_3$ and $C_2H_5$; W is Cl; and Q is O or S. In the second of the above referred to groups as represented by formula (Ia) Y and Z each are selected from hydrogen, $CH_3$, Cl and F; A is a $C_2-C_3$ saturated alkylene chain having an optional $CH_3$ branch; $R_2$ is selected from hydrogen, $CH_3$ and $C_2H_5$; $R_3$ is selected from $CH_3$ and $C_2H_5$; W is $NO_2$, $CH_3$, $CH_3O$, CN; and Q is O or S. In the third of the above referred to groups as represented by formula (Ia) Y and Z each are selected from hydrogen, $CH_3$, Cl, F; A is an unsaturated alkylene chain ($C_2-C_4$) having an optional methyl branch; $R_2$ is selected from hydrogen, $CH_3$ and $C_2H_5$; $R_3$ is selected from $CH_3$ and $C_2H_5$; W is hydrogen, Cl, $NO_2$, $CH_3$ $CH_3O$, CN; and Q is O or S.

Among the compounds represented by formula (I) above, the following are of particular interest:
3-[3-chloro-4-(phenethyloxy)phenyl]-1.1-dimethylurea,
1-[3-chloro-4-(phenethyloxy)phenyl]-3-methylurea,
3-[3-chloro-4-($\beta$-methylphenethyloxy)phenyl]-1,1-dimethylurea,
3-[3-chloro-4-($\alpha$-methylphenethyloxy)phenyl]1,1-dimethylurea,
1,1-dimethyl-3-[3-nitro-4-(phenethyloxy)phenyl]urea,
3-[3-chloro-4-(phenethyloxy)phenyl]-1,1-diethylurea,
3-[3-chloro-4-(3-phenylpropoxy)phenyl]-1,1-dimethylurea, and
1,1-dimethyl-3-[4-(phenethyloxy)phenyl]urea The present invention also relates to methods for the preparation of compounds of formula (I) and to methods for the control of monocotyledonous and dicotyledonous plant species using a herbicidally effective amount of a compound of formula (I).

Phenylurea compounds, which may be illustrated schematically by formula (II)

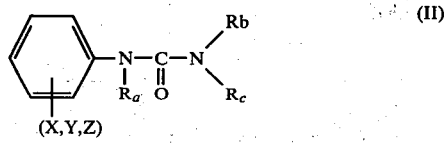

wherein $R_a$ to $R_c$ and X,Y and Z represent various substituents, are known to be herbicides, and a number of patents and published reports attest to their herbitoxic activity. Their use in the agriculture is, however, quite limited and is usually in preemergence applications.

Benzyloxyphenylurea compounds, which may be schematically illustrated by formula (III) below:

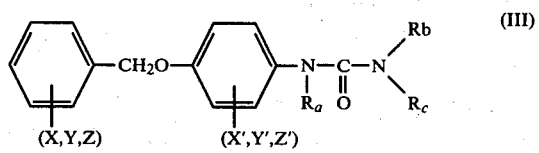

wherein X,X',Y,Y',Z,Z' and $R_a$ to $R_c$ represent various substituents, possess postemergence herbicidal activity but lack useful agronomic crop selectivity, nor is their herbicidal activity outstanding.

It has now been found, that the novel para-phenylalkoxy phenylurea compounds of the present invention show not only excellent broadleaf control when applied postemergence but also show an unexpected and useful degree of crop tolerance to wheat, barley, sorghum, corn and rice. Some of these compounds, especially the compounds wherein W is $NO_2$ also show a useful degree of crop tolerance to cotton and soybeans. Crop selectivity may be further modified by applying these compounds to said crops at different growth stages.

Said compounds also display preemergence herbicidal activity although at higher rates than those needed for postemergence control.

The compounds of formula (I) wherein X is O and A is $C_2$-$C_8$ alkylene may be conveniently prepared by the route shown below:

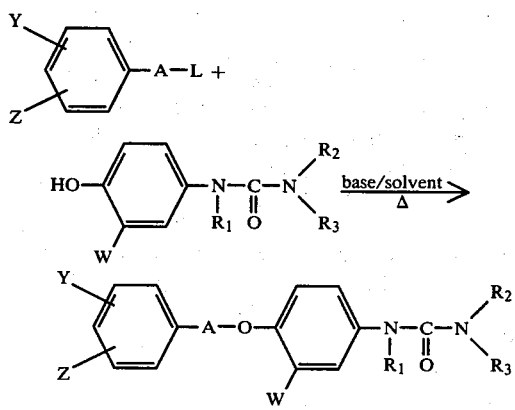

wherein Y,Z,W,$R_1$,$R_2$ and $R_3$ are as hereinabove defined except when Y=OH, $NH_2$ in which case they are suitably protected, L is selected from $-OSO_2CH_3$ or halide. Thus the methanesulfonate ester of the appropriately substituted phenylalkanol or the corresponding phenalkylhalide of formula (IV) is reacted with an ureidophenol of formula (V) in the presence of an organic or inorganic base, preferably potassium t-butoxide, and a solvent such as dimethylformamide in the temperature range of from 20° C. to 90° C. and preferably 60° C. to 80° C., for a period of time sufficient to essentially complete the reaction.

Formula (I) compounds, in which the alkylene chain (A) is substituted, may be prepared as follows:

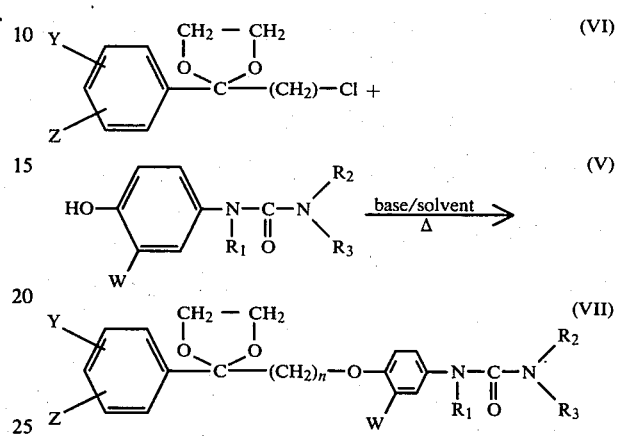

wherein Y,Z,W and $R_1$ to $R_3$ are as hereinabove defined and n is an integer of from 1 to 7. Next, the thus obtained compound of formula (VII) is hydrolyzed to yield the corresponding benzoylalkoxyphenylurea as illustrated below:

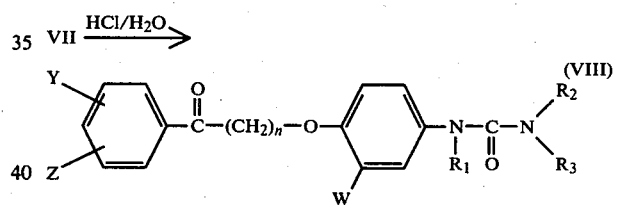

In the above depicted sequence the appropriately substituted 1,3-dioxolane of formula (VI) is reacted with an ureidophenol of formula (V) in the presence of an organic or inorganic base, preferably potassium t-butoxide and a solvent such as DMF in the temperature range of from 20° C. to 90° C., preferably 50° to 80° C. for a period of time sufficient to essentially complete the reaction. The thus obtained urea of formula (VII) is then hydrolyzed with an aqueous acid, such as hydrochloric acid to yield a benzoylalkoxyphenylurea of formula (VIII). The benzoylalkoxyphenylurea compounds of formula (VIII) may be reduced by known methods to the corresponding alcohols which are valuable intermediates for the preparation of formula (I) compounds wherein the alkylene chain (A) is substituted as defined above. Such a preparation may be schematically illustrated as follows:

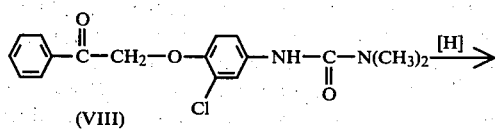

-continued

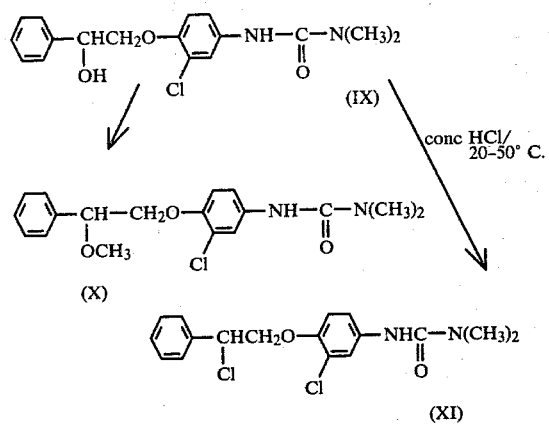

An alternate route leading to formula (I) compounds comprises reacting an isocyanate or isothiocyanate of formula (XII)

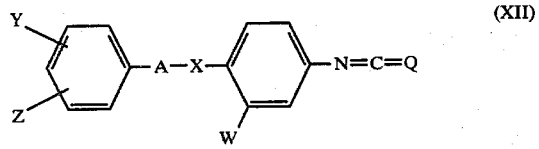

with an equimolar or excess amount of an amine of formula

to yield the desired formula (I) compound:

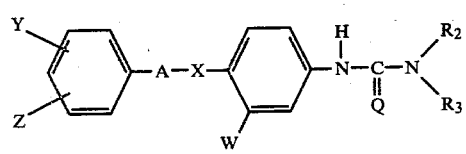

wherein $R_1$ is hydrogen and X,Y,Z,W,$R_2$ and $R_3$ are as hereinabove defined.

Similarly, the appropriate aniline of formula (XIII)

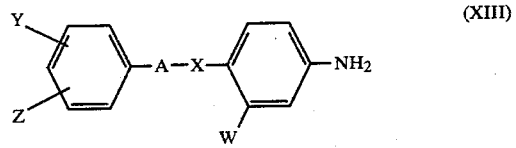

may be reacted with an isocyanate or isothiocyanate of formula $R_3-N=C=Q$ to yield a formula (I) compound of structure

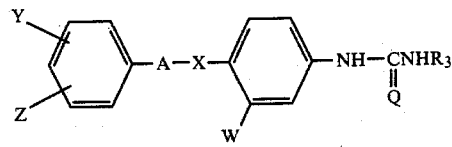

wherein $R_1$ and $R_2$ are both hydrogen, and $R_3$ is an hereinabove defined.

Conveniently, the methanesulfonate ester of an appropriately substituted phenylalkanol of formula (IV) and an appropriately substituted ureidophenol of formula (V) may be reacted in a two phase system using a phase transfer catalyst such as benzyl tributylammonium chloride and the like, to obtain the desired herbicide of formula (I):

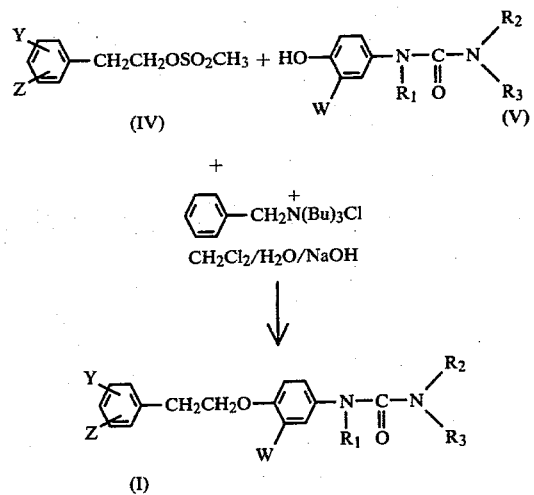

The above described preparations are further illustrated in the experimental detail appended hereto.

Formula (I) compounds, wherein X is SO or $SO_2$ are prepared by a slightly different route, as shown below:

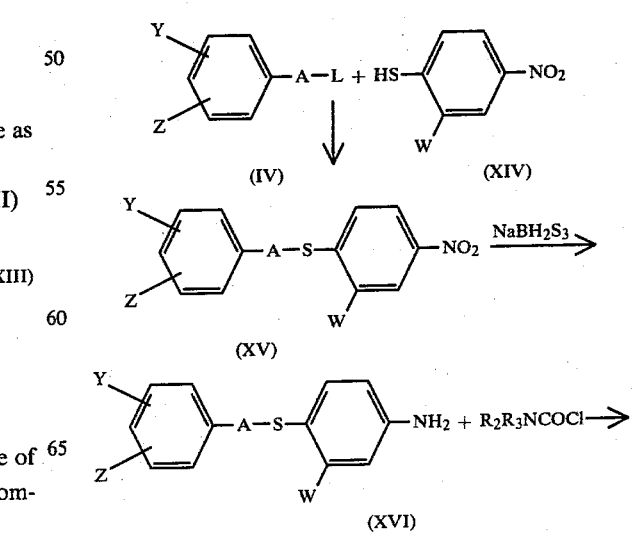

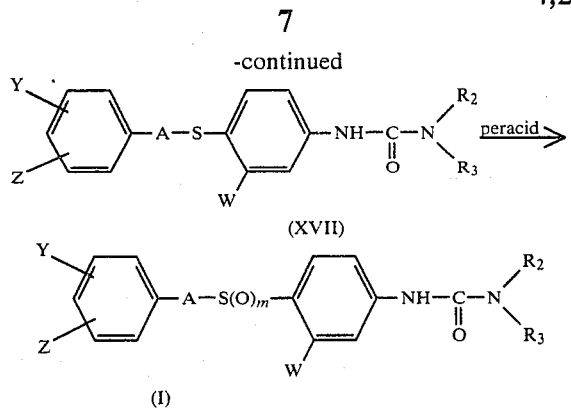

wherein A,W,Y,Z,R$_2$ and R$_3$ are as defined above except that Y cannot be NO$_2$ and m is an integer of 1 or 2.

By the above depicted route, p-nitrothiophenol of formula (XIV) is reacted with the appropriately substituted methanesulfonate ester of a phenylalkanol or the corresponding phenalkyl halide of formula (IV) in the presence of an inorganic or organic base, preferably potassium t-butoxide and a solvent, such as DMF, in the temperature range of from 20° C. to 90° C., and preferably 60° C. to 80° C. for a period of time sufficient to essentially complete the reaction. The nitro compound (XV) obtained by the above reaction is then reduced with sulfurated sodium borohydride to afford the amine of formula (XVI). This amine (XVI) is then reacted with dialkylcarbamoylchloride or the appropriate isocyanate to yield the corresponding urea (XVII). Oxidation of this compound (XVII) affords the desired urea (I).

Of interest are the following compounds represented by formula (I) above:

3-[3-chloro-4-(phenethyloxy)phenyl]-1,3-dimethylurea,
3-[3-chloro-4-(phenethyloxy)phenyl]-3-formyl-1,1-dimethylurea,
3-[3-bromo-4-(phenethyloxy)phenyl]-1,1-dimethylurea,
3-[3-fluoro-4-(phenethyloxy)phenyl]-1,1-dimethylurea,
3-[3-trifluoromethyl-4-(phenethyloxy)phenyl]-1,1-dimethylurea,
3-[3-trifluoromethylsulfonyl-4-(phenethyloxy)phenyl]-1,1-dimethylurea,
3-[3-carboethoxy-4-(phenethyloxy)phenyl]-1,1-dimethylurea,
3-[3-methylthio-4-(phenethyloxy)phenyl]-1,1-dimethylurea,
3-[3-methylsulfonyl-4-(phenethyloxy)phenyl]-1,1-dimethylurea,
3-[3-cyano-4-(phenethyloxy)phenyl]-1,1-dimethylurea,
3-[4-(2-benzoylethyloxy)-3-chlorophenyl]-1,1-dimethylurea,
3-[4-(3-benzoylpropoxy)-3-chlorophenyl]-1,1-dimethylurea,
3-{3-chloro-4-[2-(2-phenyl-1,3-dioxolan-2-yl)ethyloxy]phenyl}-1,1-dimethylurea.
3-{3-chloro-4-[3-(2-phenyl-1,3-dioxolan-2-yl)propoxy]phenyl}-1,1-dimethylurea,
3-[3-chloro-4-(β-hydroxyphenethyloxy)phenyl]-1,1-dimethylurea,
3-{3-chloro-4-[(4-hydroxy-4-phenyl)butoxy]phenyl}-1,1-dimethylurea,
3-{3-chloro-4-[(2-methyl-3-phenyl)propoxy]phenyl}-1,1-dimethylurea,
3-{3-chloro-4-[(2-fluoro-3-phenyl)propoxy]phenyl}-1,1-dimethylurea.
3-{3-chloro-4-[(2-bromo-3-phenyl)propoxy]phenyl}-1,1-dimethylurea,
3-{3-chloro-4-[(2-hydroxy-3-phenyl)propoxy]phenyl}-1,1-dimethylurea,
3-{3-chloro-4-[(2-methoxy-3-phenyl)propoxy]phenyl}-1,1-dimethylurea,
3-{3-chloro-4-[(2-cyano-3-phenyl)propoxy]phenyl}-1,1-dimethylurea,
3-{3-chloro-4-[2-methylthio-3-phenyl)propoxy]phenyl}-1,1-dimethylurea,
3-{3-chloro-4-[(3-chloro-3-phenyl)propoxy]phenyl}-1,1-dimethylurea,
3-{3-chloro-4-[(3-methoxy-3-phenyl)propoxy]phenyl}-1,1-dimethylurea,
3-{3-chloro-4-[(3-bromo-3-phenyl)propoxy]phenyl}-1,1-dimethylurea,
3-{3-chloro-4-[3-cyano-3-phenyl)propoxy]phenyl}-1,1-dimethylurea,
3-{3-chloro-4-[4-methoxy-4-phenyl)butoxy]phenyl}-1,1-dimethylurea,
3-{3-chloro-4-[(4-chloro-4-phenyl)butoxy]phenyl}-1,1-dimethylurea,
3-[3-chloro-4-(β,β-dimethylphenethyloxy)phenyl]1,1-dimethylurea,
3-[3-chloro-4-(α,β-dimethylphenethyloxy)phenyl]-1,1-dimethylurea,
3-[3-chloro-4-(β-bromo-phenethyloxy)phenyl]-1,1-dimethylurea,
3-[3-chloro-4-(β-methoxyphenethyloxy)phenyl]-1,1-dimethylurea,
3-[3-chloro-4-(β-cyanophenethyloxy)phenyl]-1,1-dimethylurea.
3-[3-chloro-4-(3-methoxyphenethyloxy)phenyl]-1,1-dimethylurea,
3-[3-chloro-4-(2-methoxyphenethyloxy)phenyl]-1,1-dimethylurea.
3-[-chloro-4-(β,4-dimethylphenethyloxy)phenyl]-1,1-dimethylurea.
3-[3-chloro-4-(α,4-dimethylphenethyloxy)phenyl]-1,1-dimethylurea.
3-[3-chloro-4-(β-methyl-4-methoxyphenethyloxy)phenyl]-1,1-dimethylurea.
3-[3-chloro-4-(β-methyl-3-methoxyphenethyloxy)phenyl]-1,1-dimethylurea.
3-[3-chloro-4-(4-hydroxyphenethyloxy)phenyl]-1,1-dimethylurea.
3-[3-chloro-4-(4-methylsulfonylphenethyloxy)phenyl]-1,1-dimethylurea.
3-[3-chloro-4-(4-methylcarbamoyloxyphenethyloxy)phenyl]-1,1-dimethylurea.
3-[3-chloro-4-(4-t-butylcarbamoyloxyphenethyloxy)phenyl]-1,1-dimethylurea.
3-{3-chloro-4-[4-(2-propynyloxy)phenethyloxy]phenyl}-1,1-dimethylurea.
3-{3-chloro-4-[4-(2-propenyloxy)phenethyloxy]phenyl}-1,1-dimethylurea.
3-{3-chloro-4-[(4-propoxy)phenethyloxy]phenyl}-1,1-dimethylurea.
1,1-dimethyl-3-[3-nitro-4-(β-methylphenethyloxy)phenyl]urea.
1,1-dimethyl-3-[3-nitro-4-(4-methylphenethyloxy)phenyl]urea.
1,1-dimethyl-3-[3-nitro-4-(4-methoxyphenethyloxy)phenyl]urea.
1,1-dimethyl-3-[3-nitro-4-(α-methylphenethyloxy)phenyl]urea.
1,1-dimethyl-3-[3-difluoromethanesulfonyl-4-(phenethyloxy)phenyl]urea.

1,1-dimethyl-3-[3,5-dinitro-4-(phenethyloxy)phenyl]urea.
3-{3-chloro-4-[3-(4-nitrophenyl)propoxy]phenyl}1,1-dimethylurea.
1-methyl-3-[3-nitro-4-(α-methylphenethyloxy)phenyl]urea.
1-methyl-3-[3-nitro-4-(phenethyloxy)phenyl]urea.
1,1-dimethyl-3-[3-nitro-4-(phenethyloxy)phenyl]thiourea.
1,1-dimethyl-3-[3-nitro-4-(α-methylphenethyloxy)phenyl]thiourea.
1,1-dimethyl-3-[3-nitro-4-(β-methylphenethyloxy)phenyl]thiourea.

These compounds can be prepared by one or more of the above discussed synthetic methods.

As stated above, formula (I) compounds of the present invention show excellent postemergence control of broadleaf weeds coupled with crop selectivity in the presence of sorghum, rice and wheat.

Said compounds also display preemergence herbicidal activity coupled with selectivity, however at somewhat higher rates than needed for postemergence control.

Surprisingly, we also find that the compounds of the invention are highly effective as fungicides useful in the treatment of agronomic crops.

In practice, the active compounds are generally formulated as dusts, dust concentrates, wettable powders, emulsion concentrates, flowable concentrates and the like.

Dusts can be prepared by grinding about 1% to 15% by weight of active compound with about 99% to 85% by weight of an inert diluent such as attaclay, diatomaceous earth, kaolin, pumice, talc and the like.

Dust concentrates are made in a similar fashion excepting that percent by weight of active ingredient is increased to about 16% to 75% of the composition.

Wettable powders are prepared in the same manner as dust concentrates, but usually contain, in addition to the active ingredient and solid diluent, from about 1% to 5% by weight of a wetting agent such as sodium isopropylnaphthalene sulfonate or the sodium salt of a sulfonated naphthalene formaldehyde condensate, and from about 1% to 5% by weight of a dispersing agent such as hydroxyethyl cellulose. A typical formulation would be 50% by weight of active ingredient, 2% of dispersing agent, 5% of wetting agent and 43% attapulgite.

Emulsion concentrates are prepared by dissolving 15% to 70% by weight of the compound in 85% to 30% by weight of a solvent such as benzene, toluene, xylene, kerosene, 2-methoxy ethanol, propylene glycol, diethylene glycol, diethylene glycol monomethyl ester, formamide, methylformamide and the like, and mixtures thereof. Advantageously, surfactants such as polyoxyethylated vegetable oil or an alkyl phenoxy polyoxyethylene ethanol are also incorporated in amounts of 1% to 5% by weight of said concentrate.

In using wettable powders, emulsion concentrates, flowable concentrates and the like, the formulated material is generally dispersed in water and applied at a rate of from 0.03 kg per hectare to about 2 kg per hectare to the plants or to the soil containing the seeds of said plants.

The invention is further illustrated by the following examples which are not to be taken as being limitative thereof.

EXAMPLE 1

General Method for the Preparation of Phenylalkoxyphenyl dimethylurea compounds

[Method A]

The appropriate ureidophenol (0.03 mol), dimethylformamide (DMF; 200 ml) and potassium t-butoxide (0.03 mol) are mixed and stirred at room temperature under a nitrogen atmosphere for one hour. Next, the appropriate methanesulfonate ester (0.03 mol) is added and the reaction mixture heated at 80° C. from 2 to 18 hours. The solution is then cooled down and the DMF removed under vacuum. The residue is dissolved in methylene chloride and water (made basic with a few drops of 1 N sodium hydroxide). The organic layer is washed with water and filtered through a 5 cm thick layer of neutral alumina. The alumina layer is washed with acetonitrile, filtrate and washings are combined and evaporated to afford the desired urea. The product may be further purified by recrystallization from the appropriate solvent.

The compounds made by this procedure are listed in Table I below.

EXAMPLE 2

Preparation of 3-[3-chloro-4-(phenethyloxy)phenyl]-1,1-dimethylurea

[Method B]

Dimethylamine (7.0 ml; 0.068 mol) is added at room temperature and under a nitrogen atmosphere to a 0.11 M solution of 3-chloro-4-(phenethyloxy) phenylisocyanate in toluene (145 ml, 0.016 mol). The reaction is exothermic and the temperature of the mixture rises to 40° C. The solution is stirred overnight and then treated with 10% aqueous sodium hydroxide (50 ml). The organic layer is separated and washed in succession with 50 ml portions of 10% aqueous sodium hydroxide, water, 3 N hydrochloric acid (twice), water and brine. The solution is dried over potassium carbonate and then concentrated under vacuum to an amber oil. The oil is dissolved in hot hexane-ethyl acetate mixture with the formation of a precipitate. The mixture is cooled and filtered to afford 4.27 g (0.0123 mol; 77%) of title product, m.p. 89°–90° C.

Analysis. Calculated for $C_{19}H_{23}N_2O_2Cl$: C 65.78; H, 6.70; N 8.07; Cl 10.22; Found: C 65.69; H 6.75; N 8.08; Cl 10.29.

Other compounds prepared by the above method from the appropriate dialkylamines and isocyanates are listed in Table I.

TABLE I $$G-X-\underset{W}{\underset{|}{C_6H_3}}-\underset{R_1}{\underset{|}{N}}-\underset{O}{\underset{\|}{C}}-N(R_2)(R_3)$$

| G | X | W | $R_1$ | $R_2$ | $R_3$ | m.p. °C. | Recryst. Solvent(s) | Analysis Calc'd. | Analysis Found | Method |
|---|---|---|---|---|---|---|---|---|---|---|
| C₆H₅—CH₂CH₂ | O | Cl | H | CH₃ | CH₃ | 113–114 | toluene-hexane | C 64.05 H 6.01 N 8.79 Cl 11.12 | C 64.31 H 6.19 N 8.78 Cl 11.12 | A |
| C₆H₅—CH₂CH₂ | O | NO₂ | H | CH₃ | CH₃ | 90–92 | isopropanol | C 61.99 H 5.81 N 12.76 | C 62.09 H 5.82 N 12.79 | A |
| C₆H₅—CH₂CH₂ | O | H | H | CH₃ | CH₃ | 143–144 | methyl cyclohexane | C 71.80 H 7.09 N 9.85 | C 71.67 H 7.06 N 9.96 | A |
| C₆H₅—CH₂CH₂ | SO₂ | Cl | H | CH₃ | CH₃ | 138–139 | toluene-hexane | C 55.65 H 5.22 N 7.64 S 8.74 Cl 9.66 | C 56.42 H 5.61 N 7.70 S 7.84 Cl 9.53 | A |
| F—C₆H₄—CH₂CH₂ | O | Cl | H | CH₃ | CH₃ | 111–112 | toluene-hexane | C 60.63 H 5.39 N 8.32 Cl 10.53 F 5.64 | C 60.77 H 5.37 N 8.50 Cl 10.48 F 5.53 | A |
| Cl—C₆H₄—CH₂CH₂ | O | Cl | H | CH₃ | CH₃ | 130–132 | toluene-hexane | C 57.81 H 5.14 N 7.93 Cl 20.08 | C 58.52 H 5.21 N 8.00 Cl 19.69 | A |
| CH₃—C₆H₄—CH₂CH₂ | O | Cl | H | CH₃ | CH₃ | 110–111 | hexane-toluene | C 64.95 H 6.36 N 8.42 Cl 10.65 | C 64.87 H 6.38 N 8.42 Cl 10.29 | A |
| CH₃O—C₆H₄—CH₂CH₂ | O | Cl | H | CH₃ | CH₃ | 136.5–138.5 | toluene | C 61.97 H 6.07 N 8.03 Cl 10.16 | C 63.09 H 6.29 N 7.81 Cl 9.83 | A |
| NO₂—C₆H₄—CH₂CH₂ | O | Cl | H | CH₃ | CH₃ | 126–131 | — | | | D |
| CH₃O—(CH₃O)C₆H₃—CH₂CH₂ | O | Cl | H | CH₃ | CH₃ | 114–117 | toluene | C 60.23 H 6.12 N 7.40 Cl 9.36 | C 60.31 H 6.30 N 7.30 Cl 9.56 | A |
| Cl—(Cl)C₆H₃—CH₂CH₂ | O | Cl | H | CH₃ | CH₃ | | | | | |
| (Cl)(Cl)C₆H₃—CH₂CH₂ | O | Cl | H | CH₃ | CH₃ | | | | | |
| Cl—(Cl)C₆H₃—CH₂CH₂ | O | Cl | H | CH₃ | CH₃ | | | | | |
| C₆H₅—CH₂CH₂ | O | Cl | CHO | CH₃ | CH₃ | | | | | |
| C₆H₅—CH₂CH₂CH₂ | O | Cl | H | CH₃ | CH₃ | 102–103 | toluene-hexane | C 64.98 H 6.36 N 8.42 Cl 10.66 | C 65.12 H 6.48 N 8.52 Cl 10.70 | A |
| C₆H₅—CH₂CH₂CH₂ | O | NO₂ | H | CH₃ | CH₃ | 104.5–105.5 | isopropanol | C 62.96 H 6.16 N 12.24 | C 62.67 H 6.19 N 12.31 | A |
| C₆H₅—CH₂CH₂CH₂ | O | H | H | CH₃ | CH₃ | 126.5–127.5 | acetonitrile | C 72.45 H 7.43 N 9.56 | C 72.46 H 7.46 N 9.56 | A |
| CH₃O—C₆H₄—CH₂CH₂CH₂ | O | Cl | H | CH₃ | CH₃ | 111–113 | toluene | C 62.89 H 6.39 N 7.72 Cl 9.77 | C 63.02 H 6.55 N 7.80 Cl 9.80 | A |

TABLE I-continued structure: G—X—(phenyl with W substituent)—N(R1)—C(=O)—N(R2)(R3)

| G | X | W | R1 | R2 | R3 | m.p. °C. | Recryst. Solvent(s) | Analysis Calc'd | Analysis Found | Method |
|---|---|---|----|----|----|---------|---------------------|-----------------|----------------|--------|
| Ph-CH₂CH(CH₃)- | O | Cl | H | CH₃ | CH₃ | 101-104 | purified by silica gel chromatography (CH₂Cl₂) | C 64.81 H 6.58 N 8.29 Cl 10.48 | C 64.98 H 6.36 N 8.42 Cl 10.66 | A |
| Ph-CH(CH₃)CH₂- | O | Cl | H | CH₃ | CH₃ | 94.5-96.5 | purified by silica gel chromatography (CH₂Cl₂) | C 64.98 H 6.36 N 8.42 Cl 10.66 | C 64.59 H 6.59 N 8.34 Cl 10.04 | A |
| Ph-CH(C₂H₅)CH₂- | O | Cl | H | CH₃ | CH₃ | 105-106 | methyl cyclohexane | C 65.77 H 6.68 N 8.08 Cl 10.22 | C 65.67 H 7.08 N 8.09 Cl 10.22 | A |
| Ph-CH₂CH(C₂H₅)- | O | Cl | H | CH₃ | CH₃ | 84.5-86 | toluene-heptane | C 65.77 H 6.68 N 8.08 Cl 10.22 | C 66.02 H 6.76 N 2.07 Cl 10.24 | A |
| Ph-CH(CH₃)CH₂CH₂- | O | Cl | H | CH₃ | CH₃ | 101.5-102 | toluene-hexane | C 65.77 H 6.68 N 8.08 Cl 10.22 | C 65.83 H 6.64 N 8.12 Cl 10.20 | A |
| Ph-CH₂CH₂CH(CH₃)- | O | Cl | H | CH₃ | CH₃ | 70-72(d) | purified by silica gel chromatography | C 65.77 H 6.68 N 8.08 Cl 10.22 | C 65.86 H 6.82 N 8.08 Cl 10.22 | A |
| Ph-CH₂CH₂CH₂CH₂- | O | Cl | H | CH₃ | CH₃ | 79-81 | toluene-hexane | C 65.77 H 6.68 N 8.08 Cl 10.22 | C 66.00 H 6.72 N 8.07 Cl 10.27 | A |
| Ph-(CH₂)₅- | O | Cl | H | CH₃ | CH₃ | 83-84 | toluene-hexane | C 66.62 H 7.12 N 7.74 Cl 9.86 | C 66.56 H 6.98 N 7.76 Cl 9.83 | A |
| Ph-CH₂CH₂- | O | Cl | H | H | CH₃ | 136-136.5 | toluene-methyl cyclohexane | C 63.06 H 5.62 N 9.19 Cl 11.63 | C 63.20 H 5.73 N 9.30 Cl 11.79 | A or C |
| Ph-CH₂CH₂CH₂- | O | Cl | H | H | CH₃ | 105-106.5 | toluene-hexane | C 64.01 H 6.01 N 8.79 Cl 11.12 | C 64.08 H 6.07 N 8.86 Cl 10.87 | A or C |
| Ph-CH₂CH₂- | O | Cl | H | C₂H₅ | C₂H₅ | 89-90 | ethyl acetate-hexane | C 65.78 H 6.70 N 8.07 Cl 10.22 | C 65.69 H 6.75 N 8.08 Cl 10.29 | B |
| Ph-CH₂CH₂- | O | Cl | H | CH₃ | C₂H₅ | | | | | |
| Ph-CH₂CH₂- | O | Cl | H | H | C₂H₅ | 129-130 | toluene | C 64.04 H 6.02 N 8.78 Cl 11.12 | C 64.26 H 6.05 N 8.58 Cl 11.06 | A or C |
| Ph-CH₂CH₂- | O | Cl | H | H | C₃H₇ | 131-132 | toluene | C 64.95 H 6.37 N 8.41 Cl 10.65 | C 65.18 H 6.58 N 8.44 Cl 10.09 | A or C |

EXAMPLE 3

Preparation of 3-[3-chloro-4-(phenethyloxy)phenyl]-1-ethylurea

[Method C]

A solution of 3-chloro-4-(phenethyloxy)aniline (2.50 g; 0.0101 mol) in toluene (100 ml) is stirred at room temperature under a nitrogen atmosphere and ethyl isocyanate (0.80 ml; 0.012 mol) added. The reaction mixture is stirred for 16 hours, and then the precipitated white solid is collected by filtration and washed with toluene to afford 1.96 g of title product, m.p. 129°-130° C.

Other compounds prepared by the above method from the appropriate anilines and alkyl isocyanates are listed in Table I.

EXAMPLE 4

Preparation of 3-[3-chloro-4-(4-nitrophenethyloxy) phenyl]-1,1-dimethylurea

[Method D]

A mixture of 4-nitrophenethyl alcohol methanesulfonate (4.9 g; 0.02 mol), 3-(3-chloro-4-hydroxyphenyl)-1,1-dimethylurea (2.2 g; 0.01 mol), water (50 ml), methylene chloride (50 ml), sodium hydroxide (0.6 g) and benzyl tributylammonium chloride (0.3 g; 0.001 mol) is stirred rapidly for five days at room temperature. The methylene chloride phase is then separated, washed with dilute base, saturated salt solution and dried over sodium sulfate. Evaporation of the solution yields an oily solid, which upon trituration with pentane affords the title product.

Other compounds prepared by the above method from the appropriate methanesulfonates and hydroxyphenylureas are listed in Table I.

EXAMPLE 5

Preparation of 3-[3-chloro-4-(phenethyloxy)phenyl]-1,1,3-trimethylurea

A mixture of sodium hydride (0.48 g; 0.01 mol as 50% dispersion in oil) and THF (25 ml) is prepared and maintained under a nitrogen atmosphere. Then 3-[3-chloro-4-(phenethyloxy)phenyl]-1,1-dimethylurea (3.19 g; 0.01 mol) is added to the above mixture. Hydrogen is evolved and a thick paste forms. After about 15 minutes methyl iodide (1.4 g; 0.01 mol) is added and the reaction mixture stirred for two hours at room temperature. After two hours reaction time the paste redissolves. Next, most of the THF is removed under vacuum, the residue dissolved in methylene chloride. The methylene chloride solution is washed with water, dried over sodium sulfate and evaporated to afford the title product as an oil.

EXAMPLE 6

Preparation of 3-chloro-4-(phenethyloxy)formanilide

A solution of 3-chloro-4-phenethyloxyaniline (6.3 g; 0.02 mol) in 88% formic acid (100 ml) is heated overnight at 85° C., and then most of the formic acid is removed under vacuum. The residue is dissolved in methylene chloride, the solution washed with 1 N hydrochloric acid, saturated sodium bicarbonate solution and saturated brine and is then dried over sodium sulfate. Evaporation of the solvent yields an oil which crystallizes; m.p. 69°–71° C.

Analysis Calculated for $C_{15}H_{14}NO_2Cl$: C 65.34; H 5.12; N 5.08; Cl 12.86; Found: C 65.40; H 5.21; N 5.08; Cl 13.04.

EXAMPLE 7

Preparation of 3-[3-chloro-4-(phenethyloxy)phenyl]-3-formyl-1-methylurea

A mixture of 3-chloro-4-(phenethyloxy)formanilide (2.9 g; 0.01 mol), triethylamine (1.52 g; 0.015 mol), methyl isocyanate (1.14 g; 0.02 mol) and anhydrous THF (25 ml) is stirred for 7 days at room temperature. Removal of the solvent under vacuum yields the product.

EXAMPLE 8

Preparation of 3-[3-chloro-4-(phenethyloxy)phenyl]-3-formyl-1,1-dimethylurea

A mixture of 3-chloro-4-(phenethyloxy)formanilide (2.9 g; 0.01 mol) and THF (25 ml) is prepared and maintained under a nitrogen atmosphere. Sodium hydride (0.48 g; 0.01 mol) is then added and the reaction mixture stirred one hour at room temperature. Next, dimethylcarbamyl chloride (1.1 g; 0.01 mol) is added, the resulting solution stirred overnight at room temperature and evaporated to afford the product.

EXAMPLE 9

Preparation of 1-(3-chloro-4-hydroxyphenyl)-3-methylurea

A solution of 4-amino-2-chlorophenol (21.5 g; 0.15 mol) in ethylacetate (400 ml) is cooled to 0° C. and then methyl isocyanate (18.6 g; 0.15 mol) added slowly. The solution is stirred for one hour and then evaporated under vacuum to afford 30 g of title product, m.p. 188°–189° C.

EXAMPLE 10

Preparation of 3-[3-chloro-4-(phenacyloxy)phenyl]-1,1-dimethylurea

A mixture of α-chloroacetophenone (4.64 g; 0.03 mol), anhydrous potassium fluoride and DMF (200 ml) is stirred for 15 minutes. Next, 3-(3-chloro-4-hydroxyphenyl)-1,1-dimethylurea (6.44 g; 0.03 mol) is added and the mixture stirred for 20 hours at room temperature and then for 24 hours at 80° C. The mixture is then drowned in water, and extracted with methylene chloride. The organic layer is separated, washed with water and filtered through a 5 cm pad of neutral alumina. The pad is washed with acetonitrile, filtrate and washings are combined and evaporated under vacuum to give a brown-yellow oil (7.0 g, 70.1%). This oil is purified by chromatographing on silica gel (eluent: methylene chloride) to afford the title compound: 6.75 g of a cream colored solid, m.p. 148°–150° C.

Analysis Calculated for: $C_{17}H_{17}ClN_2O_3$; C 61.35; H 5.15; N 8.42; Cl 10.65; Found: C 61.36; H 5.27; N 8.45; Cl 10.85.

EXAMPLE 11

Preparation of 3-chloro-4-(phenethyloxy)aniline hydrochloride

A mixture of 3-[3-chloro-4-(phenethyloxy) phenyl]-1,1-dimethylurea (16.68 g; 0.0523 mol), n-butanol (300 ml) and 50% aqueous sodium hydroxide (50 ml) is refluxed for 1.5 hours, and then poured onto 500 ml crushed ice. The resultant mixture is extracted with ether (2×200 ml). The ether solution is washed with brine, dried over potassium carbonate and cooled in an ice bath. Dry hydrochloric acid gas is bubbled through the solution. The precipitated amine hydrochloride is collected to afford 10.46 g (0.0368 mol) of product, a white solid, m.p. 198°–204° C.

EXAMPLE 12

Preparation of 3-chloro-4-(phenethyloxy)aniline

To a mixture of water (50 ml), ethanol (50 ml) and 50% aqueous sodium hydroxide (25 ml) is added 3-chloro-4-(phenethyloxy)aniline hydrochloride (8.25 g;

0.0290 mol). When the solid is all dissolved, the solution is extracted with ether (3×100 ml). The ether solution is washed with brine, dried over potassium carbonate and concentrated under vacuum to yield 5.16 g (77%) of a tan oil. This oil is distilled at 140° C. under 0.005 mm vacuum to afford the product, a colorless liquid.

Analysis Calculated for $C_{14}H_{14}NOCl$: C 67.87; H 5.71; N 5.65; Cl 14.31; Found: C 67.75; H 5.81; N 5.56; Cl 14.61.

EXAMPLE 13

Preparation of 3-chloro-4-(phenethyloxy)phenyl isocyanate

A mixture of 3-chloro-4-(phenethyloxy)aniline (16.06 g; 0.0648 mol), toluene (500 ml) and potassium carbonate (4.5 g; 0.035 mol) is prepared and maintained under nitrogen atmosphere. A 12.5% solution of phosgene in benzene (65 ml; 0.072 mol) is added to the above mixture. A precipitate forms immediately. The mixture is heated at 85° C. for 45 minutes. By the end of this period the precipitate has dissolved. The reaction mixture is cooled down and filtered. The product is not isolated but rather it is used immediately.

EXAMPLE 14

Preparation of 2-chloro-4-nitro-benzenethiol

A solution of sodium hydrosulfide hydrate (60 g technical; ~0.75 mol) in methanol (200 ml) is added to a solution of 3,4-dichloronitrobenzene (100.0 g; 0.52 mol) in methanol (750 ml) with cooling and at a rate to maintain the temperature of the reaction mixture below 40° C. After the addition is completed, the reaction mixture is stirred an additional 16 hours, and then poured on a mixture of ice and hydrochloric acid. The mixture remains strongly acidic. The precipitated yellow solid is filtered, washed and dried. This solid is purified by dissolving same in 25% aqueous sodium hydroxide, extracting the resultant solution several times with methylene chloride until the methylene chloride solution remains colorless. Next, concentrated hydrochloric acid is added to the aqueous solution dropwise to precipitate a light yellow solid and adjust the pH to 1–2. The thus formed slurry is filtered, the isolated solid is washed with water and dried to afford 52.6 g (55%) of title compound. A sample is recrystallized from cyclohexane, m.p. 77°–78° C. Lit. 73.5°–74° C. (ref. Nippon Kagaku Kaishi 1972, 756).

EXAMPLE 15

Preparation of 3-[3-amino-4-(phenethyloxy)phenyl]-1,1-dimethylurea

A mixture of 3-[3-nitro-4-(phenethyloxy)phenyl]-1,1-dimethylurea (5.8 g; 0.0175 mol), 5% palladium in $BaSO_4$ catalyst (6.0 g) and 95% ethyl alcohol (100 ml) is shaken in a hydrogen atmosphere at 2.8 kg/cm² pressure (40 psig) for 18 hours. The mixture is then filtered and the ethanol removed under vacuum. The residue is washed with toluene to afford the title compound, m.p. 125°–126° C.

Analysis Calculated for $C_{17}H_{21}N_3O_2$: C 68.21; H 7.07; N 14.04; Found: C 68.18; H 7.04; N 13.87.

EXAMPLE 16

Preparation of 2-chloro-4-nitrophenylphenethyl sulfide

[Method E]

Potassium t-butoxide (5.1 g; 0.0455 mol) is added slowly to a cooled solution of 2-chloro-4-nitrobenzenethiol (8.5 g; 0.045 mol) in dry dimethylformamide (DMF; 100 ml) with stirring. The reaction mixture is kept cold for two hours and is then allowed to warm up to room temperature at which point the solution becomes dark red. Next, a solution of 2-phenethylmethanesulfonate (9.0 g) in DMF (25 ml) is added to the above solution over a 30 minute period. The reaction mixture is heated and at 60° C. a slurry forms, which turns to a paste at 80° C. The paste is stirred and heated at 80° C. for 18 hours after which time it becomes a liquid. The reaction mixture is cooled and poured on ice (500 g) and extracted with ether (4×100 ml). The ether extracts are combined, washed with water, 10% sodium carbonate solution, saturated brine and dried over magnesium sulfate. The ethereal solution is evaporated to yield 11.0 g of a solid residue. Recrystallization from methanol (twice) yields 9.2 g (70%) of title compound, m.p. 64°–65° C.

Analysis Calculated for $C_{14}H_{12}ClNO_2S$: C 57.24; H 4.12; N 4.78; S 10.92; Cl 12.07; Found: C 57.40; H 4.17; N 4.68; S 10.64; Cl 12.09.

[Method F]

Anhydrous potassium carbonate (15 g; 0.11 mol) is added to a solution of 2-phenylethanethiol (13.7 g; =13.4 ml; 0.10 mol) in 3:1 methanol-$H_2O$ (200 ml). The above mixture is stirred and a solution of 3,4-dichloronitrobenzene (19.2 g; 0.10 mol) in methanol (100 ml) added, and the reaction mixture heated for 24 hours at 60° C. It is then cooled down and poured into ice cold dilute hydrochloric acid. The mixture is extracted with methylene chloride (3×), the organic phase washed with 10% sodium carbonate solution and brine and dried over magnesium sulfate. The methylene chloride solution is then evaporated to yield a yellow solid. Recrystallization from acetone-methanol affords 16.2 g of product, m.p. 62°–64° C.

This product has identical spectral properties to that prepared by Method E. A second crop of 9.94 g of product is isolated from the mother liquor giving a total yield of 89%.

EXAMPLE 17

Preparation of 2-chloro-4-aminophenyl phenethyl sulfide, hydrochloride

Dry tetrahydrofuran (THF; 20 ml) is added to a mixture of sodium borohydride (1.89 g; 0.05 mol) and sulfur (4.8 g; 0.15 mol). Vigorous gas evolution commences and the reaction mixture is cooled in a cold water bath. After the gas evolution ceases, a solution of 2-chloro-4-nitrophenyl phenethyl sulfide (14.65 g; 0.05 mol) in dry THF (50 ml) is added to the above mixture. The reaction mixture is stirred for 15 hours at room temperature and then at 80° C. for 2 hours. It is then cooled down, 20% sodium hydroxide (30 ml) added, and the mixture extracted with ether. The extract is washed with water, saturated brine and dried over magnesium sulfate. Ethanolic hydrogen chloride solution is added dropwise to the ethereal solution to precipitate the title product. The product is isolated by filtration, washed with ether

EXAMPLE 18

Preparation of
1,1-dimethyl-3-[3-chloro-4-(phenethylthio)phenyl]urea

Anhydrous potassium carbonate (10 g) and dimethylcarbamyl chloride (4.0 g; 0.037 mol) are added to a solution of 2-chloro-4-aminophenyl phenethyl sulfide hydrochloride (3.0 g; 0.01 mol) in dry DMF (75 ml) at 25° C. The reaction mixture is heated at 60° C. for 15 hours and then poured into ice water (500 ml). The precipitate (74%) of title product, a white solid, m.p. 133°–134° C.

EXAMPLE 19

Preparation of
1,1-dimethyl-3-[3-chloro-4-(phenethylsulfonyl)phenyl]urea

To a cold (5° C.) solution of 1,1-dimethyl-3-[3-chloro-4-(phenethylthio)phenyl]urea (2.48 g; 0.0074 mol) in dry chloroform (100 ml) is added m-chloroperbenzoic acid (3.0 g; 85% real). The reaction mixture is stirred for one hour at 5° C., after which time thin layer chromatographic (tlc) analysis indicates the absence of starting material and the presence of two new components. The mixture is kept at 5°–10° C. for 3 days after which time tlc indicates the presence of only one component. The mixture is filtered, the isolated solid washed with chloroform. The chloroform solutions are combined, washed with water, sodium bicarbonate solution and brine, and dried over magnesium sulfate. The solution is then evaporated, the residual oil triturated with toluene-pentane to afford the title product, 2.15 g (79%) of a solid, m.p. 136°–138° C.

and dried to afford 10.4 g (69%), m.p. 213°–214° C. (d). A sample is prepared for analysis by recrystallization from ethanol-ethyl acetate m.p. 213°–214° C. (d).

EXAMPLE 20

Preparation of
1-methyl-3-[3-chloro-4-phenethylthio)phenyl]urea

A solution of 2-chloro-4-aminophenyl phenethyl sulfide (1.35 g; 0.005 mol) in toluene is prepared by treating the aqueous suspension of the corresponding amine hydrochloride with excess sodium carbonate solution and then extracting the amine with toluene from the aqueous reaction mixture. The toluene solution of the amine is dried over magnesium sulfate, methyl isocyanate (0.6 g; 0.011 mol) added and the reaction mixture allowed to stand for 24 hours. After 24 hours, a white precipitate is present in the reaction mixture. Cyclohexane is added, the reaction mixture is filtered and the isolated solid recrystallized from toluene-hexane to afford 1.32 g (82.5%) of title product, m.p. 128°–129° C.

EXAMPLE 21

General procedure for the preparation of esters of methanesulfonic acid

A solution of the appropriate alcohol (0.1 mol) and triethylamine (0.15 mol) in methylene chloride (150 ml) is rapidly stirred, chilled to −15° C. and methanesulfonyl chloride (0.11 mol) added at a rate to maintain the reaction temperature below −10° C. After the addition is completed, the solution is stirred for 30 minutes in the cold and then at room temperature for two hours. Next, the methylene chloride solution is separated, washed with ice cold water, ice cold 10% hydrochloric acid, saturated sodium bicarbonate solution, saturated brine, and then dried over sodium sulfate. Finally, the appropriate ester is isolated by evaporating the methylene chloride solution under vacuum.

Esters of methanesulfonic acid prepared by the above procedure are listed in Table II below, together with their physical data, when such is available.

TABLE II

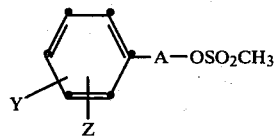

| No. | Y | Z | A | m.p.° C. | Calc'd | | Found | | Remarks |
|---|---|---|---|---|---|---|---|---|---|
| 1 | p-CH$_3$ | H | CH$_2$CH$_2$ | 50–52 | C | 56.05 | C | 55.80 | |
| | | | | | H | 6.58 | H | 6.71 | |
| | | | | | S | 14.96 | S | 14.71 | |
| 2 | H | H | CH$_3$<br>\|<br>CH$_2$CH— | straw oil | C | 56.05 | C | 56.12 | |
| | | | | | H | 6.58 | H | 6.76 | |
| | | | | | S | 14.96 | S | 15.18 | |
| 3 | p-Cl | H | CH$_2$CH$_2$ | 40–44 | C | 46.05 | C | 46.50 | |
| | | | | | H | 4.73 | H | 4.89 | |
| | | | | | S | 13.66 | S | 13.60 | |
| | | | | | Cl | 15.11 | Cl | 15.32 | |
| 4 | H | H | (CH$_2$)$_4$ | straw oil | C | 57.87 | C | 58.70 | |
| | | | | | H | 7.07 | H | 7.36 | |
| | | | | | S | 14.05 | S | 13.75 | |
| 5 | H | H | CH$_3$<br>\|<br>CHCH$_2$ | amber oil | | | | | lit. J.O.C. 38 (8) 1518 (1973) |
| 6 | H | H | (CH$_2$)$_3$ | amber oil | C | 56.04 | C | 55.98 | |
| | | | | | H | 6.54 | H | 6.71 | |
| | | | | | S | 14.96 | S | 14.94 | |
| 7 | H | H | (CH$_2$)$_5$ | amber oil | C | 54.48 | C | 54.72 | |
| | | | | | H | 7.49 | H | 7.86 | |
| | | | | | S | 13.23 | S | 13.08 | |
| 8 | H | H | CH$_2$CH$_2$ | amber oil | | | | | lit. J.O.C. 38 (8) 1518 (1973) |
| 9 | p-OCH$_3$ | H | CH$_2$CH$_2$ | yellow | C | 52.15 | C | 51.49 | |
| | | | | | H | 6.13 | H | 5.92 | |

TABLE II-continued

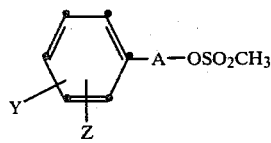

| No. | Y | Z | A | m.p.° C. | Calc'd | | Found | | Remarks |
|---|---|---|---|---|---|---|---|---|---|
| 10 | H | H | CH$_3$<br>\|<br>CH$_2$CH$_2$CH | oil<br>straw<br>oil | S<br>C<br>H<br>S | 13.93<br>57.87<br>7.07<br>14.05 | S<br>C<br>H<br>S | 13.36<br>57.23<br>7.14<br>12.96 | |
| 11 | H | H | C$_2$H$_5$<br>\|<br>CHCH$_2$ | brown<br>oil | C<br>H<br>S | 57.87<br>7.07<br>14.05 | C<br>H<br>S | 58.03<br>7.21<br>13.86 | |
| 12 | p-NO$_2$ | H | CH$_2$CH$_2$ | 80.5–82.5 | | | | | J.O.C. 38 1518 (1973)<br>m.p. 80–81° C. |
| 13 | p-OCH$_3$ | m-OCH$_3$ | CH$_2$CH$_2$ | yellow<br>oil | C<br>H<br>S | 50.75<br>6.20<br>12.32 | C<br>H<br>S | 50.42<br>5.74<br>12.23 | |
| 14 | H | H | C$_2$H$_5$<br>\|<br>CH$_2$CH | brown<br>oil | C<br>H<br>S | 57.87<br>7.07<br>14.05 | C<br>H<br>S | 58.17<br>7.38<br>13.88 | |
| 15 | H | H | CH$_3$<br>\|<br>CHCH$_2$CH$_2$ | | C<br>H<br>S | 58.87<br>7.07<br>14.05 | C<br>H<br>S | 58.17<br>7.38<br>13.88 | |

EXAMPLE 22

Preparation of 2-(3-chloropropyl)-2-phenyl-1,3-dioxolane

A mixture of γ-chlorobutyrophenone (33.2 g; 0.182 mol), ethylene glycol (20.3 ml; 0.363 mol), p-toluenesulfonic acid (a pinch) and toluene (300 ml) is heated at reflux for 40 hours, and the water formed in the reaction is azeotroped off. After 20 hours, more ethylene glycol (20.3 ml; 0.363 mol) is added. On completion of the reaction the mixture is extracted with saturated aqueous sodium bicarbonate solution (300 ml), the organic layer is washed with 1 N sodium hydroxide solution and then with water, and is evaporated to afford 37.0 g of a cream colored solid, m.p. 54°–55.5° C.

EXAMPLE 23

Preparation of 3-{3-chloro-4-(2-phenyl-1,3-dioxolan-2-yl)propoxy)-phenyl}-1,1-dimethylurea A mixture of 3-(3-chloro-4-hydroxyphenyl)-1,1-dimethylurea (6.44 g; 0.03 mol), potassium-t-butoxide (3.37 g; 0.03 mol) and DMF (200 ml) is stirred for 30 minutes, then 2-(3-chloropropyl)-2-phenyl-1,3-dioxolane (6.8 g; 0.03 mol) is added and the reaction mixture stirred for 5 days at 50° C. The reaction mixture is then poured into brine and extracted with methylene chloride. The organic layer is washed with water and filtered through a 5 cm deep bed of neutral alumina. The alumina bed is washed with acetonitrile, filtrate and washings are combined and evaporated to afford 11.42 g of product, a red-brown oil, which slowly crystallizes. Recrystallization from a toluene-hexane mixture (200 ml) yields 6.2 g of bronze colored needles, m.p. 127.5°–130° C.

EXAMPLE 24

Preparation of 3-[4-(3-benzoylpropoxy)-3-chlorophenyl]-1,1-dimethylurea

A mixture of 3-{3-chloro-4-[3-(2-phenyl-1,3-dioxolan-2-yl)propoxy]phenyl}-1,1-dimethylurea (2.03 g; 0.005 mol), tetrahydrofuran (10 ml) and 10% aqueous hydrochloric acid (2 ml) is stirred overnight. The reaction mixture is poured into brine (100 ml) and extracted with methylene chloride. The organic layer is washed with water, dried and evaporated to afford the product: 1.69 g of an off-white solid. Recrystallization from a toluene-hexane mixture (50 ml) yields 1.33 g of cream colored needles, m.p. 129°–130° C.

EXAMPLE 25

Postemergence Herbicidal Activity

The postemergence herbicidal activity of the compounds of the present invention is demonstrated by the following tests, wherein a variety of monocotyledonous, and dicotyledonous plants are treated with test compounds dispersed in aqueous acetone mixtures. In the tests, seedling plants are grown in separate cups for about 2 weeks. The test compounds are dispersed in 50/50 acetone/water mixtures containing 0.5% TWEEN ® 20, polyoxyethylene sorbitan monolaurate surfactant of Atlas Chemical Industries, in sufficient quantity to provide the equivalent of about 0.063 kg to 2.0 kg per hectare of active compound when applied to the plants through a spray nozzle operating at 2.81 kg/cm$^2$ pressure for a predetermined time. After spraying, the plants are placed on greenhouse benches and are cared for in the usual manner, commensurate with conventional greehouse practices. Two weeks after treatment, the seedling plants are examined and rated according to the rating system provided below. The data obtained are reported in Table III below. The data in said table have been obtained either by a single trial or by replicating a trial two or more times, in which case the data are reported as averages.

| RATING SYSTEM | |
|---|---|
| RATING | % CONTROL (COMPARED TO CHECK) |
| 9—Complete kill | 100 |
| 8—Approaching complete kill | 91–99 |
| 7—Good herbicidal effect | 80–90 |

RATING SYSTEM

| RATING | % CONTROL (COMPARED TO CHECK) |
|---|---|
| 6—Herbicidal effect | 65–79 |
| 5—Definite injury | 45–64 |
| 4—Injury | 30–44 |
| 3—Moderate effect | 10–29 |
| 2—Slight effect | 6–15 |
| 1—Trace effect | 1–5 |
| 0—No effect | 0 |

The above rating scale is based upon a visual observation of plant stand, vigor, malformation, size, chlorosis, and overall plant appearance as compared with a control.

| Plant Species | |
|---|---|
| Cocklebur | (*Xanthium pensylvanicum*) |
| Jimsonweed | (*Datura stramonium*) |
| Lambsquarters | (*Chenopodium album*) |
| Morningglory | (*Ipomoea*, spp) |
| Mustard, wild | (*Brassica kaber*) |
| Pigweed, redroot | (*Amaranthus retroflexus*) |
| Ragweed, common | (*Ambrosia artemisiifolia*) |
| Velvetleaf | (*Abutilon theophrasti*) |
| Bindweed, field | (*Convolvulus arvensis*) |
| Thistle, Canada | (*Cirsium arvense*) |
| Foxtail, green | (*Setaria viridis*) |
| Barnyardgrass | *Echinochloa crus-galli* |
| Blackgrass | *Alopecurus myosuroides* |
| Buckwheat, tartary | *Fagopyrum tataricum* |
| Canarygrass | *Phalaris minor* |
| Crabgrass | *Digitaria sanguinalis* |
| Johnsongrass | *Sorghum halepense* |
| Mayweed | *Matricaria chamomilla* |
| Nutsedge, purple | *Cyperus rotundus* |
| Nutsedge, yellow | *Cyperus esculentus* |
| Oat, wild | *Avena fatua* |
| Quackgrass | *Agropyron repens* |
| Barley | (*Hordeum vulgare*) |
| Corn | (*Zea mays*) |
| Cotton | (*Gossipium hirsutum*) |
| Rice** | (*Oryza sativa*) |
| Sorghum, grain | (*Sorghum bicolor*) |
| Soybeans | (*Glycine max*) |
| Wheat* | (*Triticum aestivum*) |
| Beet, sugar | (*Beta vulgaris*) |

*Cultivars used in tests: E(ra); A(nza); W(aldron)
**Cultivars used in tests: Upland; Star bonnet, Saturn

TABLE III

Evaluation of the Selective Postemergence Broadleaf Herbicidal Activity of the Compounds of the Invention in the Presence of Graminaceous Crops, Soybeans and Cotton (Rates are given in kg/ha)

| Rate (kg/ha): | 2.000 | 1.000 | .500 | .250 | .125 | .063 | .032 | .016 |
|---|---|---|---|---|---|---|---|---|
| 3-[3-Chloro-4-(5-phenylpentyloxy)phenyl]-1,1-dimethylurea | | | | | | | | |
| BARNYARDGRASS | 0.7 | 0.7 | 0.3 | 0.0 | 0.0 | 0.0 | 0.0 | 0.0 |
| CRABGRASS, (HAIR) | 0.0 | 0.0 | 0.0 | 0.0 | 0.0 | 0.0 | 0.0 | 0.0 |
| FOXTAIL, GREEN | 3.3 | 4.3 | 2.0 | 1.3 | 1.0 | 0.3 | 0.0 | 0.0 |
| NUTSEDGE, PURPLE | 2.5 | 0.5 | 0.0 | 0.0 | 0.0 | 0.0 | | |
| OAT, WILD | 0.3 | 0.0 | 0.0 | 0.0 | 0.0 | 0.0 | 0.0 | 0.0 |
| COCKLEBUR | 9.0 | 7.3 | 3.7 | 2.7 | 2.7 | 2.7 | 0.0 | 0.0 |
| JIMSONWEED | 3.7 | 1.0 | 0.0 | 0.0 | 0.0 | 0.0 | 0.0 | 0.0 |
| LAMBSQUARTERS, C | 7.7 | 5.3 | 4.0 | 3.3 | 3.0 | 1.3 | 0.0 | 0.0 |
| MORNINGGLORY SPP | 4.0 | 3.0 | 3.0 | 2.3 | 1.7 | 0.0 | 0.0 | 0.0 |
| MUSTARD, WILD | 9.0 | 8.7 | 9.0 | 9.0 | 5.0 | 4.3 | 0.0 | 0.0 |
| PIGWEED, REDROOT | 4.7 | 8.7 | 6.7 | 6.3 | 2.7 | 1.0 | 0.0 | 0.0 |
| RAGWEED, COMMON | 8.5 | 7.0 | 4.0 | 2.5 | 1.5 | 1.5 | | |
| VELVETLEAF | 5.7 | 1.7 | 1.7 | 0.0 | 0.0 | 0.0 | 0.0 | 0.0 |
| BARLEY, UNSPECIF | 1.5 | 1.0 | 1.0 | 0.0 | 0.0 | 0.0 | | |
| BARLEY, LARKER | 0.0 | 0.0 | 0.0 | 0.0 | 0.0 | 0.0 | 0.0 | 0.0 |
| CORN, FIELD | 2.7 | 1.5 | 1.0 | 0.3 | 0.0 | 0.0 | 0.0 | 0.0 |
| RICE, UPLAND | 0.3 | 0.3 | 0.3 | 0.0 | 0.0 | 0.0 | 0.0 | 0.0 |
| SORGHUM, GRAIN | 1.0 | 0.5 | 0.5 | 0.0 | 0.0 | 0.0 | | |
| SOYBEAN | 6.5 | 4.5 | 3.0 | 1.5 | 1.5 | 0.0 | | |
| WHEAT, SPRING, X | 0.0 | 0.0 | 0.0 | 0.0 | 0.0 | 0.0 | | |
| WHEAT, SPRING, E | 0.0 | 0.0 | 0.0 | 0.0 | 0.0 | 0.0 | 0.0 | 0.0 |
| WHEAT, SPRING, W | 0.0 | 0.0 | 0.0 | 0.0 | 0.0 | 0.0 | 0.0 | 0.0 |
| WHEAT, WINTER, X | 0.0 | 0.0 | 0.0 | 0.0 | 0.0 | 0.0 | | |
| 3-[3-Chloro-4-(phenethyloxy)phenyl]-1,1-dimethylurea | | | | | | | | |
| BARNYARDGRASS | 1.9 | 1.2 | 0.3 | 0.1 | 0.1 | 0.0 | 0.0 | 0.0 |
| BLACKGRASS | 3.0 | 3.0 | 2.0 | | | | | |
| CANARYGRASS, LIT | 7.0 | 4.0 | 4.0 | | | | | |
| CRABGRASS, (HAIR) | 6.0 | 5.5 | 4.5 | 3.5 | 0.0 | 1.0 | 0.0 | 0.0 |
| FOXTAIL, GREEN | 5.1 | 4.6 | 3.4 | 2.3 | 1.2 | 0.8 | 0.5 | 0.0 |
| JOHNSONGRASS (FR) | 1.0 | 1.0 | 0.0 | | | | | |
| NUTSEDGE, PURPLE | 1.5 | 1.4 | 1.1 | 0.3 | 0.2 | 0.1 | | |
| NUTSEDGE, YELLOW | 9.0 | 9.0 | 4.0 | | | | | |
| OAT, WILD | 1.5 | 0.8 | 0.3 | 0.1 | 0.0 | 0.0 | 0.0 | |
| QUACKGRASS | 1.0 | 1.0 | 0.0 | | | | | |
| BINDWEED, FIELD | 9.0 | 9.0 | 8.5 | 2.0 | 4.0 | 3.0 | 2.0 | |
| BUCKWHEAT, TARTA | 9.0 | 9.0 | 9.0 | | | | | |
| COCKLEBUR | 6.4 | 6.8 | 6.5 | 7.7 | 5.9 | 3.2 | 9.0 | |
| JIMSONWEED | 7.8 | 7.3 | 7.4 | 4.2 | 2.7 | 3.3 | 9.0 | |
| LAMBSQUARTERS, C | 8.9 | 8.8 | 8.8 | 8.2 | 7.2 | 5.0 | 4.3 | 0.0 |
| MAYWEED | 9.0 | 9.0 | 9.0 | | | | | |
| MORNINGGLORY SPP | 9.0 | 7.8 | 7.6 | 6.9 | 4.8 | 4.3 | 3.5 | 0.0 |
| MUSTARD, WILD | 9.0 | 9.0 | 8.8 | 9.0 | 8.6 | 8.4 | 6.3 | 2.0 |
| PIGWEED, REDROOT | 8.9 | 8.9 | 8.9 | 8.5 | 6.5 | 4.6 | 7.0 | 2.0 |
| PIGWEED SPP. | 9.0 | 9.0 | 9.0 | 8.3 | 6.0 | 6.0 | 3.0 | |

TABLE III-continued

Evaluation of the Selective Postemergence Broadleaf Herbicidal Activity of the Compounds of the Invention in the Presence of Graminaceous Crops, Soybeans and Cotton

| Rate (kg/ha): | (Rates are given in kg/ha) | | | | | | | |
|---|---|---|---|---|---|---|---|---|
| | 2.000 | 1.000 | .500 | .250 | .125 | .063 | .032 | .016 |
| RAGWEED, COMMON | 8.9 | 8.5 | 8.6 | 7.4 | 6.6 | 4.8 | 4.5 | |
| THISTLE, CANADA | 9.0 | 9.0 | 7.0 | 7.0 | 9.0 | 9.0 | 0.0 | |
| VELVETLEAF | 8.0 | 7.4 | 5.7 | 4.3 | 2.6 | 1.8 | 1.3 | 0.0 |
| BARLEY, UNSPECIF | 2.8 | 2.4 | 2.0 | 1.0 | 0.5 | 0.5 | | |
| BARLEY, LARKER | 2.0 | 1.0 | 0.0 | 0.0 | 0.0 | 0.0 | 0.0 | 0.0 |
| SUGAR-BEET | | 9.0 | 9.0 | 9.0 | 9.0 | 9.0 | 9.0 | |
| CORN, FIELD | 3.1 | 3.7 | 3.7 | 2.4 | 1.9 | 1.5 | 1.0 | |
| COTTON | 9.0 | 9.0 | 9.0 | 9.0 | 1.0 | 6.0 | 2.5 | |
| RICE, UPLAND | 3.3 | 3.0 | 2.2 | 1.6 | 0.6 | 0.4 | | 0.0 |
| RICE, STAR BONNE | 7.0 | 6.0 | 3.0 | 2.0 | 2.0 | 2.0 | 2.0 | |
| RICE, NATO | 8.0 | 6.0 | 2.0 | 2.0 | 2.0 | 1.0 | 1.0 | |
| RICE, SATURN | 7.0 | 3.3 | 3.3 | 2.0 | 2.0 | 1.5 | 0.5 | |
| SORGHUM, GRAIN | 2.4 | 1.2 | 0.9 | 0.5 | 0.3 | 0.5 | | |
| SOYBEAN | 7.9 | 7.1 | 6.1 | 4.6 | 2.3 | 1.1 | 0.5 | |
| WHEAT, SPRING, X | 1.8 | 1.3 | 1.1 | 0.5 | 0.2 | 0.2 | | |
| WHEAT, SPRING, E | 2.0 | 1.7 | 1.7 | 1.0 | 0.0 | 0.0 | 0.0 | |
| WHEAT, SPRING, W | 4.0 | 4.0 | 3.0 | 3.0 | 2.0 | 1.0 | 0.0 | 0.0 |
| WHEAT, SPRING, A | 5.0 | 5.0 | 3.0 | 3.0 | 1.0 | 1.0 | 0.0 | |
| WHEAT, WINTER, X | 1.0 | 0.0 | 0.0 | 0.0 | 0.0 | 0.0 | | |
| 3-[3-Chloro-4-(3-phenylpropoxy)phenyl]-1,1-dimethylurea | | | | | | | | |
| BARNYARDGRASS | 1.4 | 1.0 | 0.2 | 0.2 | 0.0 | 0.0 | 0.0 | 0.0 |
| BLACKGRASS | 3.0 | 3.0 | 3.0 | | | | | |
| CANARYGRASS, LIT | 9.0 | 9.0 | 9.0 | | | | | |
| CRABGRASS, (HAIR) | 2.0 | 4.0 | 1.0 | 0.0 | 0.0 | 0.0 | 0.0 | |
| FOXTAIL, GREEN | 3.4 | 3.2 | 1.8 | 1.2 | 0.8 | 0.5 | 0.0 | 0.0 |
| JOHNSONGRASS (FR) | 1.0 | 1.0 | 0.0 | | | | | |
| NUTSEDGE, PURPLE | 1.3 | 0.8 | 0.5 | 0.0 | 2.0 | 0.7 | | |
| NUTSEDGE, YELLOW | 3.0 | 9.0 | 3.0 | | | | | |
| OAT, WILD | 1.0 | 2.8 | 2.3 | 0.8 | 0.3 | 0.0 | 0.0 | 0.0 |
| QUACKGRASS | 2.0 | 1.0 | 0.0 | | | | | |
| BINDWEED, FIELD | 9.0 | 9.0 | 9.0 | | | | | |
| BUCKWHEAT, TARTA | 9.0 | 9.0 | 9.0 | | | | | |
| COCKLEBUR | 9.0 | 7.2 | 7.2 | 6.5 | 4.0 | 2.4 | 1.0 | |
| JIMSONWEED | 4.8 | 3.3 | 4.0 | 4.0 | 3.8 | 2.8 | 0.0 | 9.0 |
| LAMBSQUARTERS, C | 7.5 | 7.8 | 7.8 | 7.4 | 6.2 | 5.0 | 1.5 | 0.0 |
| MAYWEED | 9.0 | 9.0 | 9.0 | | | | | |
| MORNINGGLORY SPP | 9.0 | 9.0 | 9.0 | 7.3 | 2.8 | 1.5 | | 0.0 |
| MUSTARD, WILD | 9.0 | 9.0 | 9.0 | 9.0 | 8.5 | 8.0 | 3.7 | 2.0 |
| PIGWEED, REDROOT | 9.0 | 9.0 | 9.0 | 7.8 | 5.0 | 4.8 | 4.5 | 9.0 |
| PIGWEED SPP. | 9.0 | 9.0 | 9.0 | 4.0 | 2.0 | 0.0 | 0.0 | |
| RAGWEED, COMMON | 8.8 | 7.4 | 5.0 | 3.8 | 1.2 | 0.4 | 0.0 | |
| THISTLE, CANADA | 9.0 | 9.0 | 9.0 | | | | | |
| VELVETLEAF | 9.0 | 8.0 | 6.4 | 4.8 | 2.6 | 8.6 | 0.0 | 0.0 |
| BARLEY, UNSPECIF | 4.0 | 4.0 | 2.0 | 1.3 | 0.5 | 0.3 | 0.0 | |
| BARLEY, LARKER | 0.0 | 0.0 | 0.0 | 0.0 | 0.0 | 0.0 | 0.0 | 0.0 |
| CORN, FIELD | 7.3 | 6.0 | 6.5 | 2.8 | 0.5 | 0.8 | 0.0 | 0.0 |
| COTTON | | 9.0 | 9.0 | 5.0 | 1.0 | 1.0 | 0.0 | |
| RICE, UPLAND | 3.3 | 2.3 | 1.5 | 1.0 | 0.5 | 0.3 | 0.0 | 0.0 |
| RICE, STAR BONNE | 4.0 | 4.0 | 3.0 | 0.0 | 0.0 | 0.0 | 0.0 | |
| RICE, NATO | 1.0 | 1.0 | 0.0 | 0.0 | 0.0 | 0.0 | 0.0 | |
| RICE, SATURN | 1.0 | 1.0 | 0.0 | 1.0 | 0.0 | 0.0 | 0.0 | |
| SORGHUM, GRAIN | 1.3 | 1.3 | 1.0 | 0.7 | 0.7 | 0.7 | | |
| SOYBEAN | 8.8 | 8.8 | 9.0 | 4.5 | 1.8 | 1.3 | 0.0 | |
| WHEAT, SPRING, X | 2.0 | 2.0 | 1.0 | 0.0 | 0.0 | 0.0 | 0.0 | |
| WHEAT, SPRING, E | 6.0 | 5.0 | 5.0 | 1.0 | 0.0 | 0.0 | 0.0 | 0.0 |
| WHEAT, SPRING, W | 3.0 | 3.0 | 3.0 | 0.0 | 0.0 | 0.0 | 0.0 | 0.0 |
| WHEAT, SPRING, A | 2.0 | 2.0 | 1.0 | 1.0 | 0.0 | 0.0 | 0.0 | |
| WHEAT, WINTER, X | 2.0 | 2.0 | 0.0 | 0.0 | 0.0 | 0.0 | | |
| 1,1-Dimethyl-3-[4-phenethyloxy)phenyl]urea | | | | | | | | |
| BARNYARDGRASS | 2.0 | 1.0 | 0.0 | 0.0 | 0.0 | 0.0 | 0.0 | |
| BLACKGRASS | 0.0 | 0.0 | 0.0 | | | | | |
| CANARYGRASS, LIT | 6.0 | 4.0 | 3.0 | | | | | |
| CRABGRASS, (HAIR) | | 1.0 | 0.0 | 0.0 | 0.0 | 0.0 | 0.0 | |
| FOXTAIL, GREEN | 3.0 | 1.5 | 1.0 | 1.0 | 0.5 | 0.0 | 0.0 | |
| NUTSEDGE, PURPLE | 0.0 | 0.0 | 0.0 | 0.0 | 0.0 | 0.0 | | |
| NUTSEDGE, YELLOW | 9.0 | 9.0 | 3.0 | | | | | |
| OAT, WILD | 2.5 | 3.3 | 1.7 | 0.5 | 0.0 | 0.0 | 0.0 | |
| QUACKGRASS | 1.0 | 0.0 | 0.0 | | | | | |
| BINDWEED, FIELD | 9.0 | 9.0 | 9.0 | | | | | |
| BUCKWHEAT, TARTA | 9.0 | 9.0 | 9.0 | | | | | |
| COCKLEBUR | 9.0 | 7.7 | 9.0 | 9.0 | 8.5 | 7.5 | 7.0 | |
| JIMSONWEED | 9.0 | 9.0 | 8.0 | 6.0 | 3.0 | 3.0 | 0.0 | |
| LAMBSQUARTERS, C | 9.0 | 9.0 | 9.0 | 9.0 | 8.5 | 5.5 | 4.0 | |
| MAYWEED | 9.0 | 9.0 | 9.0 | | | | | |
| MORNINGGLORY SPP | 9.0 | 9.0 | 8.5 | 8.5 | 8.5 | 6.0 | 0.0 | 7.0 |
| MUSTARD, WILD | 9.0 | 9.0 | 8.0 | 6.0 | 6.0 | 4.5 | 7.0 | |

TABLE III-continued
Evaluation of the Selective Postemergence Broadleaf Herbicidal Activity of the Compounds of the Invention in the Presence of Graminaceous Crops, Soybeans and Cotton

| Rate (kg/ha): | 2.000 | 1.000 | .500 | .250 | .125 | .063 | .032 | .016 |
|---|---|---|---|---|---|---|---|---|
| PIGWEED, REDROOT | 9.0 | 9.0 | 9.0 | 7.5 | 6.5 | 2.0 | 1.0 | |
| RAGWEED, COMMON | 9.0 | 6.5 | 4.0 | 3.5 | 2.0 | 2.0 | 0.0 | |
| THISTLE, CANADA | 9.0 | 9.0 | 9.0 | | | | | |
| VELVETLEAF | 3.0 | 6.0 | 5.5 | 5.5 | 0.5 | 0.0 | 0.0 | |
| BARLEY, UNSPECIF | 4.0 | 4.0 | 3.5 | 2.0 | 1.0 | 0.0 | 0.0 | |
| BARLEY, LARKER | 2.0 | 2.0 | 2.0 | | | | | |
| CORN, FIELD | 6.0 | 7.0 | 4.3 | 4.0 | 1.5 | 1.0 | 2.0 | |
| COTTON | | 9.0 | 9.0 | 9.0 | 9.0 | 0.0 | 0.0 | |
| RICE, UPLAND | 4.0 | 2.5 | 2.0 | 2.0 | 0.5 | 0.0 | 0.0 | |
| RICE, SATURN | 4.0 | 4.0 | 3.0 | | | | | |
| SORGHUM, GRAIN | 2.0 | 2.0 | 1.0 | 1.0 | 1.0 | 0.0 | | |
| SOYBEAN | 9.0 | 9.0 | 9.0 | 7.5 | 1.5 | 1.0 | 0.0 | |
| WHEAT, SPRING, X | 1.0 | 2.0 | 1.5 | 1.0 | 0.0 | 0.0 | 0.0 | |
| WHEAT, SPRING, E | 2.0 | 1.0 | 1.0 | | | | | |
| 1,1-Dimethyl-3-[4-(3-phenylpropoxy)phenyl]urea | | | | | | | | |
| BARNYARDGRASS | | 0.0 | 0.0 | 0.0 | 0.0 | 0.0 | 0.0 | |
| CRABGRASS, (HAIR) | | 3.0 | 3.0 | 2.0 | 0.0 | 0.0 | 0.0 | |
| FOXTAIL, GREEN | | 3.0 | 2.0 | 0.0 | 0.0 | 0.0 | 0.0 | |
| OAT, WILD | | 7.0 | 3.0 | 1.0 | 0.0 | 0.0 | 0.0 | |
| COCKLEBUR | | 9.0 | 4.0 | 4.0 | 4.0 | 0.0 | 0.0 | |
| JIMSONWEED | | 5.0 | | | | | | |
| LAMBSQUARTERS, C | | 9.0 | 7.0 | 7.0 | 4.0 | 4.0 | 4.0 | |
| MORNINGGLORY SPP | | 9.0 | 9.0 | 6.0 | 6.0 | 3.0 | 0.0 | |
| MUSTARD, WILD | | 9.0 | 9.0 | 9.0 | 9.0 | 7.0 | 5.0 | |
| PIGWEED, REDROOT | | 9.0 | 9.0 | 9.0 | 9.0 | 3.0 | 0.0 | |
| RAGWEED, COMMON | | 6.0 | 2.0 | 0.0 | 0.0 | 0.0 | 0.0 | |
| VELVETLEAF | | 9.0 | 1.0 | 0.0 | 0.0 | 0.0 | 0.0 | |
| BARLEY, UNSPECIF | | 2.0 | 2.0 | 1.0 | 0.0 | 0.0 | 0.0 | |
| CORN, FIELD | | 4.0 | 9.0 | 9.0 | 2.0 | 0.0 | 0.0 | |
| COTTON | | 9.0 | 9.0 | 9.0 | 3.0 | | 0.0 | |
| RICE, UPLAND | | 3.0 | 3.0 | 3.0 | 3.0 | 1.0 | 0.0 | |
| SOYBEAN | | 6.0 | | 3.0 | 0.0 | 0.0 | 0.0 | |
| WHEAT, SPRING, X | | 2.0 | 0.0 | 0.0 | 0.0 | 0.0 | 0.0 | |
| 3-[3-Chloro-4-(4-phenylbutoxy)phenyl]-1,1-dimethylurea | | | | | | | | |
| BARNYARDGRASS | 1.0 | 0.0 | 0.0 | 0.0 | 0.0 | 0.0 | 0.0 | |
| CRABGRASS, (HAIR) | | 2.0 | 0.0 | 0.0 | 0.0 | 0.0 | 0.0 | |
| FOXTAIL, GREEN | 7.0 | 3.0 | 1.5 | 1.0 | 1.0 | 0.5 | 0.0 | |
| NUTSEDGE, PURPLE | 3.0 | 3.0 | 3.0 | 3.0 | 2.0 | 2.0 | | |
| OAT, WILD | 2.0 | 4.5 | 3.0 | 2.0 | 1.5 | 0.0 | 0.0 | |
| COCKLEBUR | 9.0 | 9.0 | 9.0 | 9.0 | 7.5 | 7.5 | 9.0 | |
| JIMSONWEED | 9.0 | 9.0 | 5.5 | 5.5 | 3.0 | 3.0 | 0.0 | |
| LAMBSQUARTERS, C | 6.0 | 7.5 | 6.0 | 6.0 | 5.0 | 2.5 | 2.0 | |
| MORNINGGLORY SPP | 9.0 | 9.0 | 9.0 | 8.5 | 8.5 | 8.5 | 2.0 | |
| MUSTARD, WILD | 9.0 | 9.0 | 9.0 | 9.0 | 9.0 | 9.0 | 9.0 | |
| PIGWEED, REDROOT | 8.0 | 8.5 | 7.5 | 7.5 | 6.0 | 4.5 | 2.0 | |
| RAGWEED, COMMON | 9.0 | 8.0 | 8.5 | 5.5 | 4.0 | 2.5 | 0.0 | |
| VELVETLEAF | 9.0 | 5.0 | 4.0 | 1.5 | 1.0 | 0.0 | 0.0 | |
| BARLEY, UNSPECIF | 3.0 | 2.5 | 2.5 | 0.5 | 0.0 | 0.0 | 0.0 | |
| CORN, FIELD | 7.0 | 8.0 | 6.0 | 3.0 | 2.0 | 1.5 | 0.0 | |
| COTTON | | 9.0 | 9.0 | 4.0 | 3.0 | 3.0 | 0.0 | |
| RICE, UPLAND | 0.0 | 1.0 | 1.0 | 1.0 | 0.5 | 0.0 | 0.0 | |
| SORGHUM, GRAIN | 2.0 | 1.0 | 0.0 | 0.0 | 0.0 | 0.0 | | |
| SOYBEAN | 8.0 | 5.5 | 3.0 | 3.5 | 2.0 | 1.0 | 0.0 | |
| WHEAT, SPRING, X | | 3.0 | | 0.0 | 0.0 | 0.0 | 0.0 | |
| WHEAT, WINTER, X | 6.0 | 3.0 | 2.0 | 2.0 | 0.0 | 0.0 | | |
| 3-[3-Chloro-4-(4-fluorophenethyloxy)phenyl]-1,1-dimethylurea | | | | | | | | |
| BARNYARDGRASS | 0.0 | 0.0 | 0.0 | 0.0 | 0.0 | 0.0 | | |
| CRABGRASS, (HAIR) | 2.0 | 1.0 | 0.0 | 0.0 | 0.0 | 0.0 | | |
| FOXTAIL, GREEN | 9.0 | 9.0 | 9.0 | 3.0 | 0.0 | 0.0 | | |
| OAT, WILD | 1.0 | 0.0 | 0.0 | 0.0 | 0.0 | 0.0 | | |
| COCKLEBUR | 9.0 | 7.0 | 6.0 | 5.0 | 4.0 | 4.0 | | |
| JIMSONWEED | 9.0 | 8.0 | 7.0 | 7.0 | 7.0 | 7.0 | | |
| LAMBSQUARTERS, C | 9.0 | 9.0 | 9.0 | 9.0 | 7.0 | 6.0 | | |
| MORNINGGLORY SPP | 9.0 | 9.0 | 4.0 | 3.0 | 3.0 | 3.0 | | |
| MUSTARD, WILD | 9.0 | 9.0 | 9.0 | 9.0 | 9.0 | 9.0 | | |
| PIGWEED, REDROOT | 9.0 | 9.0 | 9.0 | 9.0 | 9.0 | 0.0 | | |
| RAGWEED, COMMON | 9.0 | 9.0 | 9.0 | 9.0 | 3.0 | 2.0 | | |
| VELVETLEAF | 8.0 | 6.0 | 3.0 | 2.0 | 0.0 | 0.0 | | |
| CORN, FIELD | 9.0 | 9.0 | 9.0 | 2.0 | 0.0 | 0.0 | | |
| COTTON | 9.0 | 9.0 | 3.0 | 2.0 | 2.0 | 2.0 | | |
| RICE, UPLAND | 4.0 | 4.0 | 2.0 | 0.0 | 2.0 | 0.0 | | |
| SORGHUM, GRAIN | 2.0 | 0.0 | 0.0 | 0.0 | 0.0 | 0.0 | | |
| SOYBEAN | 9.0 | 9.0 | 8.0 | 8.0 | 8.0 | 2.0 | | |
| WHEAT, SPRING, X | 2.0 | 6.0 | 3.0 | 3.0 | 3.0 | 2.0 | | |
| 3-[3-Chloro-4-($\beta$-methylphenethyloxy)phenyl]-1,1-dimethylurea | | | | | | | | |
| BARNYARDGRASS | 0.5 | 0.5 | 0.0 | 0.0 | 0.0 | 0.0 | | |

TABLE III-continued
Evaluation of the Selective Postemergence Broadleaf Herbicidal Activity of the Compounds of the Invention in the Presence of Graminaceous Crops, Soybeans and Cotton

| Rate (kg/ha): | 2.000 | 1.000 | .500 | .250 | .125 | .063 | .032 | .016 |
|---|---|---|---|---|---|---|---|---|
| CRABGRASS, (HAIR) | 6.0 | 8.0 | 7.0 | 3.0 | 2.0 | 0.0 | | |
| FOXTAIL, GREEN | 5.5 | 5.3 | 2.7 | 1.7 | 1.7 | 0.7 | 0.0 | |
| NUTSEDGE, PURPLE | 3.0 | 1.0 | 1.0 | 0.0 | 0.0 | 0.0 | | |
| OAT, WILD | 3.5 | 2.5 | 1.0 | 0.5 | 0.0 | 0.0 | | |
| BINDWEED, FIELD | | 9.0 | 9.0 | 9.0 | 9.0 | 0.0 | 0.0 | |
| COCKLEBUR | 8.5 | 8.7 | 8.7 | 6.0 | 9.0 | 4.7 | 9.0 | |
| JIMSONWEED | 6.0 | 9.0 | 5.3 | 5.5 | 3.3 | 3.3 | 1.0 | |
| LAMBSQUARTERS, C | 9.0 | 9.0 | 9.0 | 5.7 | 7.3 | 2.7 | 0.0 | |
| MORNINGGLORY SPP | 9.0 | 9.0 | 9.0 | 4.0 | 3.7 | 1.0 | 1.0 | |
| MUSTARD, WILD | 9.0 | 9.0 | 9.0 | 9.0 | 8.7 | 9.0 | 3.0 | |
| PIGWEED, REDROOT | 8.5 | 9.0 | 9.0 | 7.5 | 7.0 | 3.5 | | |
| PIGWEED SPP. | | 9.0 | 9.0 | 9.0 | 7.0 | 3.0 | 0.0 | |
| RAGWEED, COMMON | 9.0 | 8.7 | 7.3 | 5.3 | 5.7 | 3.0 | 0.0 | |
| THISTLE, CANADA | | 2.0 | | 9.0 | 9.0 | 4.0 | 0.0 | |
| VELVETLEAF | 5.0 | 6.0 | 4.0 | 1.3 | 0.7 | 0.0 | 0.0 | |
| BARLEY, UNSPECIF | 2.0 | 2.0 | 2.0 | 0.0 | 0.0 | 0.0 | | |
| SUGAR-BEET | | 9.0 | 9.0 | 2.0 | 6.0 | 4.0 | 4.0 | |
| CORN, FIELD | 1.0 | 5.0 | 4.7 | 1.0 | 3.7 | 1.7 | 2.0 | |
| COTTON | 9.0 | 9.0 | 9.0 | 9.0 | 8.5 | .5 | 3.0 | |
| RICE, UPLAND | 4.5 | 1.5 | 1.0 | 1.0 | 0.5 | 0.5 | | |
| RICE, SATURN | | 4.0 | 4.0 | 2.0 | 2.0 | 0.0 | 0.0 | |
| SORGHUM, GRAIN | 1.0 | 0.0 | 0.0 | 0.0 | 0.0 | 0.0 | | |
| SOYBEAN | 8.0 | 6.7 | 4.3 | 2.3 | 1.7 | 0.0 | 0.0 | |
| WHEAT, SPRING, X | 5.0 | 4.0 | 3.0 | 1.5 | 1.0 | 1.0 | | |
| WHEAT, SPRING, E | | 1.0 | 1.0 | 0.0 | 0.0 | 0.0 | 0.0 | |
| 3-[3-Chloro-4-(4-chlorophenethyloxy)phenyl]-1,1-dimethylurea | | | | | | | | |
| BARNYARDGRASS | 1.0 | 0.0 | 0.0 | 0.0 | 0.0 | 0.0 | | |
| CRABGRASS, (HAIR) | 2.0 | 1.0 | 0.0 | 0.0 | 0.0 | 0.0 | | |
| FOXTAIL, GREEN | 3.0 | 2.0 | 0.0 | 0.0 | 0.0 | 0.0 | | |
| OAT, WILD | 1.0 | 1.0 | 0.0 | 0.0 | 0.0 | 0.0 | | |
| COCKLEBUR | 9.0 | 9.0 | 8.0 | 7.0 | 7.0 | 7.0 | | |
| JIMSONWEED | 9.0 | 9.0 | 9.0 | 8.0 | 9.0 | 9.0 | | |
| LAMBSQUARTERS, C | 9.0 | 9.0 | 9.0 | 9.0 | 9.0 | 8.0 | | |
| MORNINGGLORY SPP | 4.0 | 3.0 | 1.0 | 0.0 | 0.0 | 0.0 | | |
| MUSTARD, WILD | 9.0 | 9.0 | 9.0 | 9.0 | 9.0 | 9.0 | | |
| PIGWEED, REDROOT | 9.0 | 9.0 | 9.0 | 8.0 | 8.0 | 8.0 | | |
| RAGWEED, COMMON | 9.0 | 8.0 | 7.0 | 7.0 | 7.0 | 7.0 | | |
| VELVETLEAF | 2.0 | 1.0 | 0.0 | 0.0 | 0.0 | 0.0 | | |
| CORN, FIELD | 2.0 | 2.0 | 2.0 | 2.0 | 0.0 | 0.0 | | |
| COTTON | 9.0 | 9.0 | 9.0 | 9.0 | 9.0 | 0.0 | | |
| RICE, UPLAND | 3.0 | 3.0 | 3.0 | 1.0 | 0.0 | 0.0 | | |
| SORGHUM, GRAIN | 0.0 | 0.0 | 0.0 | 0.0 | 0.0 | 0.0 | | |
| SOYBEAN | 3.0 | 3.0 | 3.0 | 0.0 | 0.0 | 0.0 | | |
| WHEAT, SPRING, X | 3.0 | 2.0 | 1.0 | 1.0 | 1.0 | 0.0 | | |
| 3-[3-Chloro-4-(α-methylphenethyloxy)phenyl]-1,1-dimethylurea | | | | | | | | |
| BARNYARDGRASS | 0.0 | 0.0 | 0.0 | 0.0 | 0.0 | 0.0 | | |
| CRABGRASS, (HAIR) | 9.0 | 6.0 | 3.0 | 1.0 | 0.0 | 0.0 | | |
| FOXTAIL, GREEN | 9.0 | 5.5 | 5.0 | 1.5 | 0.5 | 0.0 | 0.0 | |
| OAT, WILD | 1.0 | 0.0 | 0.0 | 0.0 | 0.0 | 0.0 | | |
| BINDWEED, FIELD | | 9.0 | 7.0 | 7.0 | 2.0 | 0.0 | 0.0 | |
| COCKLEBUR | 8.0 | 8.5 | 8.5 | 8.5 | 4.5 | 3.5 | 2.0 | |
| JIMSONWEED | 9.0 | 8.0 | 9.0 | 9.0 | 4.5 | 4.5 | 0.0 | |
| LAMBSQUARTERS, C | 9.0 | 9.0 | 9.0 | 6.0 | 6.0 | 4.5 | 0.0 | |
| MORNINGGLORY SPP | 9.0 | 9.0 | 9.0 | 6.0 | 2.5 | 0.0 | 0.0 | |
| MUSTARD, WILD | 9.0 | 9.0 | 9.0 | 9.0 | 9.0 | 9.0 | 0.0 | |
| PIGWEED, REDROOT | 9.0 | 9.0 | 9.0 | 9.0 | 3.0 | 2.0 | | |
| PIGWEED SPP. | | 9.0 | 9.0 | 9.0 | 2.0 | 0.0 | 0.0 | |
| RAGWEED, COMMON | 9.0 | 9.0 | 8.5 | 4.5 | 2.5 | 1.0 | 0.0 | |
| THISTLE, CANADA | | 9.0 | 3.0 | 9.0 | 2.0 | 0.0 | 0.0 | |
| VELVETLEAF | 9.0 | 8.0 | 4.0 | 1.0 | 0.0 | 0.0 | 0.0 | |
| SUGAR-BEET | | 9.0 | 9.0 | 9.0 | 9.0 | 0.0 | 0.0 | |
| CORN, FIELD | | 9.0 | 9.0 | 5.0 | 4.0 | 0.0 | 0.0 | |
| COTTON | 9.0 | 9.0 | 8.5 | 5.0 | 0.0 | 0.0 | 0.0 | |
| RICE, UPLAND | 1.0 | 1.0 | 1.0 | 1.0 | 0.0 | 0.0 | | |
| RICE, SATURN | | 5.0 | 3.0 | 0.0 | 0.0 | 0.0 | 0.0 | |
| SORGHUM, GRAIN | 1.0 | 1.0 | 0.0 | 0.0 | 0.0 | 0.0 | | |
| SOYBEAN | 9.0 | 4.5 | 4.0 | 2.8 | 0.0 | 0.0 | 0.0 | |
| WHEAT, SPRING, X | 3.0 | 2.0 | 2.0 | 2.0 | 0.0 | 0.0 | | |
| WHEAT, SPRING, E | | 1.0 | 0.0 | 0.0 | 0.0 | 0.0 | 0.0 | |
| 1-[3-Chloro-4-(phenethoxy)phenyl]-3-methylurea | | | | | | | | |
| BARNYARDGRASS | 1.0 | 0.0 | 0.0 | 0.0 | 0.0 | 0.0 | | |
| FOXTAIL, GREEN | 4.0 | 4.5 | 4.5 | 2.0 | 1.0 | 0.5 | 0.0 | |
| NUTSEDGE, PURPLE | 1.0 | 1.0 | 0.0 | 0.0 | 0.0 | 0.0 | | |
| OAT, WILD | 1.0 | 1.0 | 0.0 | 0.0 | 0.0 | 0.0 | | |
| BINDWEED, FIELD | | 2.0 | 9.0 | 7.0 | 9.0 | 1.0 | 0.0 | |
| COCKLEBUR | 9.0 | 9.0 | 9.0 | 9.0 | 3.5 | 3.0 | 4.0 | |

TABLE III-continued
Evaluation of the Selective Postemergence Broadleaf Herbicidal Activity of the Compounds of the Invention in the Presence of Gramineaceous Crops, Soybeans and Cotton

| Rate (kg/ha): | 2.000 | 1.000 | .500 | .250 | .125 | .063 | .032 | .016 |
|---|---|---|---|---|---|---|---|---|
| JIMSONWEED | 4.0 | 3.0 | 9.0 | 4.5 | 4.5 | 4.5 | 9.0 | |
| LAMBSQUARTERS, C | 9.0 | 9.0 | 8.5 | 6.5 | 5.0 | 2.0 | 1.0 | |
| MORNINGGLORY SPP | 9.0 | 8.5 | 9.0 | 9.0 | 5.0 | 2.5 | 1.0 | |
| MUSTARD, WILD | 9.0 | 9.0 | 9.0 | 9.0 | 8.5 | 7.5 | 3.0 | |
| PIGWEED, REDROOT | 9.0 | 9.0 | 9.0 | 6.0 | 5.0 | 4.0 | | |
| PIGWEED SPP. | | 9.0 | 9.0 | 9.0 | 7.0 | 6.0 | 0.0 | |
| RAGWEED, COMMON | 9.0 | 9.0 | 9.0 | 8.0 | 7.0 | 6.5 | 6.0 | |
| THISTLE, CANADA | | 9.0 | 9.0 | 9.0 | 9.0 | 0.0 | 0.0 | |
| VELVETLEAF | 8.0 | 7.5 | 7.5 | 2.5 | 1.0 | 0.5 | 0.0 | |
| BARLEY, UNSPECIF | 3.0 | 2.0 | 2.0 | 1.0 | 1.0 | 0.0 | | |
| SUGAR-BEET | | 9.0 | 9.0 | 9.0 | 9.0 | 7.0 | 3.0 | |
| CORN, FIELD | 2.0 | 5.0 | 5.0 | 5.0 | 4.5 | 0.5 | 0.0 | |
| COTTON | | 9.0 | 7.0 | 2.0 | 2.0 | 1.0 | 1.0 | |
| RICE, UPLAND | 1.0 | 1.0 | 0.0 | 0.0 | 0.0 | 0.0 | | |
| RICE, SATURN | | 4.0 | 2.0 | 2.0 | 1.0 | 0.0 | 0.0 | |
| SORGHUM, GRAIN | 1.0 | 1.0 | 1.0 | 1.0 | 0.0 | 0.0 | | |
| SOYBEAN | 8.0 | 3.3 | 2.5 | 1.3 | 0.8 | 0.5 | 0.0 | |
| WHEAT, SPRING, X | | 1.0 | 1.0 | 0.0 | 0.0 | 0.0 | | |
| WHEAT, SPRING, E | | 0.0 | 0.0 | 0.0 | 0.0 | 0.0 | 0.0 | |
| 1,1-Dimethyl-3-[3-nitro-4-(3-phenylpropoxy)phenyl]urea | | | | | | | | |
| BARNYARDGRASS | | 0.0 | 0.0 | 0.0 | 0.0 | 0.0 | | |
| FOXTAIL, GREEN | | 3.0 | 2.0 | 1.0 | 0.0 | 0.0 | | |
| NUTSEDGE, PURPLE | | 0.0 | 0.0 | 0.0 | 0.0 | 0.0 | | |
| OAT, WILD | | 0.0 | 0.0 | 0.0 | 0.0 | 0.0 | | |
| COCKLEBUR | | 9.0 | 3.0 | 0.0 | 0.0 | 0.0 | | |
| JIMSONWEED | | 0.0 | 0.0 | 0.0 | 0.0 | 0.0 | | |
| LAMBSQUARTERS, C | | 9.0 | 8.0 | 8.0 | 6.0 | 3.0 | | |
| MORNINGGLORY SPP | | 3.0 | 3.0 | 2.0 | 1.0 | | | |
| MUSTARD, WILD | | 9.0 | 9.0 | 9.0 | 7.0 | 6.0 | | |
| PIGWEED, REDROOT | | 9.0 | 8.0 | 8.0 | 7.0 | 3.0 | | |
| RAGWEED, COMMON | | 8.0 | 3.0 | 0.0 | 0.0 | 0.0 | | |
| VELVETLEAF | | 9.0 | 3.0 | 1.0 | 0.0 | 0.0 | | |
| BARLEY, UNSPECIF | | 0.0 | 0.0 | 0.0 | 0.0 | 0.0 | | |
| CORN, FIELD | | 3.0 | 1.0 | 0.0 | 0.0 | 0.0 | | |
| RICE, UPLAND | | 0.0 | 0.0 | 0.0 | 0.0 | 0.0 | | |
| SORGHUM, GRAIN | | 0.0 | 0.0 | 0.0 | 0.0 | 0.0 | | |
| SOYBEAN | | 2.0 | 1.0 | 0.0 | 0.0 | 0.0 | | |
| WHEAT, SPRING, X | | 0.0 | 0.0 | 0.0 | 0.0 | 0.0 | | |
| 1-[3-Chloro-4-(phenethyloxy)phenyl]-3-(2-ethoxyethyl)urea | | | | | | | | |
| BARNYARDGRASS | 0.0 | 0.0 | 0.0 | 0.0 | 0.0 | 0.0 | | |
| FOXTAIL, GREEN | 0.0 | 0.0 | 0.0 | 0.0 | 0.0 | 0.0 | 0.0 | |
| NUTSEDGE, PURPLE | 0.0 | 0.0 | 0.0 | 0.0 | 0.0 | 0.0 | | |
| OAT, WILD | 0.0 | 0.0 | 0.0 | 0.0 | 0.0 | 0.0 | | |
| BINDWEED, FIELD | | 2.0 | 0.0 | 0.0 | 0.0 | 0.0 | 0.0 | |
| COCKLEBUR | 7.0 | 9.0 | 6.5 | 3.0 | 0.0 | 0.0 | 0.0 | |
| JIMSONWEED | 0.0 | 4.5 | 4.5 | 0.0 | 0.0 | 0.0 | 0.0 | |
| LAMBSQUARTERS, C | 4.0 | 5.5 | 3.5 | 2.0 | 1.0 | 0.5 | 0.0 | |
| MORNINGGLORY SPP | 2.0 | 7.5 | 5.0 | 5.0 | 1.5 | 0.0 | 0.0 | |
| MUSTARD, WILD | 6.0 | 8.5 | 5.5 | 2.0 | 0.0 | 1.0 | 0.0 | |
| PIGWEED, REDROOT | 9.0 | 9.0 | 9.0 | 6.0 | 3.0 | 1.0 | | |
| PIGWEED SPP. | | 8.0 | 3.0 | 1.0 | 0.0 | 0.0 | 0.0 | |
| RAGWEED, COMMON | 9.0 | 8.0 | 7.5 | 4.0 | 1.5 | 0.0 | 0.0 | |
| THISTLE, CANADA | | 3.0 | 1.0 | 0.0 | 0.0 | 0.0 | 0.0 | |
| VELVETLEAF | 0.0 | 0.5 | 0.0 | 0.0 | 0.0 | 0.0 | 0.0 | |
| BARLEY, UNSPECIF | 0.0 | 0.0 | 0.0 | 0.0 | 0.0 | 0.0 | | |
| SUGAR-BEET | | 1.0 | | 1.0 | 0.0 | 0.0 | 0.0 | |
| CORN, FIELD | 0.0 | 4.0 | 2.0 | 1.0 | 0.0 | 0.0 | 0.0 | |
| COTTON | | 3.0 | 0.0 | 0.0 | 0.0 | 0.0 | 0.0 | |
| RICE, UPLAND | 0.0 | 0.0 | 0.0 | 0.0 | 0.0 | 0.0 | | |
| RICE, SATURN | | 1.0 | 0.0 | 0.0 | 0.0 | 0.0 | 0.0 | |
| SORGHUM, GRAIN | 0.0 | 0.0 | 0.0 | 0.0 | 0.0 | 0.0 | | |
| SOYBEAN | 0.0 | 0.3 | 0.0 | 0.0 | 0.0 | 0.0 | 0.0 | |
| WHEAT, SPRING, X | 0.0 | 0.0 | 0.0 | 0.0 | 0.0 | 0.0 | | |
| WHEAT, SPRING, E | | 0.0 | 0.0 | 0.0 | 0.0 | 0.0 | 0.0 | |
| 3'-Chloro-4'-phenethyloxy-4-morpholinecarboxanilide | | | | | | | | |
| BARNYARDGRASS | 0.0 | 0.0 | 0.0 | 0.0 | 0.0 | 0.0 | | |
| FOXTAIL, GREEN | 3.0 | 2.0 | 1.0 | 1.0 | 0.0 | 0.0 | | |
| NUTSEDGE, PURPLE | 0.0 | 0.0 | 0.0 | 0.0 | 0.0 | 0.0 | | |
| OAT, WILD | 0.0 | 0.0 | 0.0 | 0.0 | 0.0 | 0.0 | | |
| COCKLEBUR | 8.0 | 9.0 | 9.0 | 9.0 | 9.0 | 0.0 | | |
| JIMSONWEED | 0.0 | 0.0 | 0.0 | 0.0 | 0.0 | 0.0 | | |
| LAMBSQUARTERS, C | 9.0 | 8.0 | 3.0 | 0.0 | 0.0 | 0.0 | | |
| MORNINGGLORY SPP | 9.0 | 0.0 | 0.0 | 0.0 | 0.0 | 0.0 | | |
| MUSTARD, WILD | 9.0 | 9.0 | 9.0 | 9.0 | 6.0 | 0.0 | | |
| PIGWEED, REDROOT | 9.0 | 9.0 | 9.0 | 3.0 | 2.0 | 1.0 | | |
| RAGWEED, COMMON | 0.0 | 0.0 | 0.0 | 0.0 | 0.0 | 0.0 | | |

TABLE III-continued
Evaluation of the Selective Postemergence Broadleaf Herbicidal Activity of the Compounds of the Invention in the Presence of Graminaceous Crops, Soybeans and Cotton

| Rate (kg/ha): | (Rates are given in kg/ha) | | | | | | | |
|---|---|---|---|---|---|---|---|---|
| | 2.000 | 1.000 | .500 | .250 | .125 | .063 | .032 | .016 |
| VELVETLEAF | 1.0 | 0.0 | 0.0 | 0.0 | 0.0 | 0.0 | | |
| BARLEY, UNSPECIF | 0.0 | 0.0 | 0.0 | 0.0 | 0.0 | 0.0 | | |
| CORN, FIELD | 0.0 | 0.0 | 0.0 | 0.0 | 0.0 | 0.0 | | |
| RICE, UPLAND | 0.0 | 0.0 | 0.0 | 0.0 | 0.0 | 0.0 | | |
| SORGHUM, GRAIN | 0.0 | 0.0 | 0.0 | 0.0 | 0.0 | 0.0 | | |
| SOYBEAN | 0.0 | 0.0 | 0.0 | 0.0 | 0.0 | 0.0 | | |
| WHEAT, SPRING, X | 0.0 | 0.0 | 0.0 | 0.0 | 0.0 | 0.0 | | |
| 3-[3-Chloro-4-(4-methylphenethyloxy)phenyl]-1,1-dimethylurea | | | | | | | | |
| BARNYARDGRASS | 0.0 | 0.0 | 0.0 | 0.0 | 0.0 | 0.0 | | |
| FOXTAIL, GREEN | 2.0 | 0.0 | 0.0 | 0.0 | 0.0 | 0.0 | | |
| NUTSEDGE, PURPLE | 0.0 | 0.0 | 0.0 | 0.0 | 0.0 | 0.0 | | |
| OAT, WILD | 0.0 | 0.0 | 0.0 | 0.0 | 0.0 | 0.0 | | |
| COCKLEBUR | 9.0 | 3.0 | 3.0 | | 0.0 | 0.0 | | |
| JIMSONWEED | 0.0 | 0.0 | 0.0 | 0.0 | 0.0 | 0.0 | | |
| LAMBSQUARTERS, C | 9.0 | 9.0 | 9.0 | 9.0 | 0.0 | 0.0 | | |
| MORNINGGLORY SPP | 9.0 | 9.0 | 9.0 | 4.0 | 0.0 | 0.0 | | |
| MUSTARD, WILD | 9.0 | 9.0 | 9.0 | 9.0 | 0.0 | 0.0 | | |
| PIGWEED, REDROOT | 9.0 | 9.0 | 9.0 | 4.0 | | 0.0 | | |
| RAGWEED, COMMON | 9.0 | 9.0 | 5.0 | 9.0 | 9.0 | 0.0 | | |
| VELVETLEAF | 2.0 | 0.0 | 0.0 | 0.0 | 0.0 | 0.0 | | |
| BARLEY, UNSPECIF | 0.0 | 0.0 | 0.0 | 0.0 | 0.0 | 0.0 | | |
| CORN, FIELD | 0.0 | 0.0 | 0.0 | 0.0 | 0.0 | 0.0 | | |
| RICE, UPLAND | 1.0 | 3.0 | 0.0 | 0.0 | 0.0 | 0.0 | | |
| SORGHUM, GRAIN | 0.0 | 0.0 | 0.0 | 0.0 | 0.0 | 0.0 | | |
| SOYBEAN | 6.0 | 0.0 | 2.0 | 1.0 | 0.0 | 0.0 | | |
| WHEAT, SPRING, X | 0.0 | 0.0 | 0.0 | 0.0 | 0.0 | 0.0 | | |
| 3-[3-Chloro-4-(4-methoxyphenethyloxy)phenyl]-1,1-dimethylurea | | | | | | | | |
| BARNYARDGRASS | 0.0 | 0.0 | 0.0 | 0.0 | 0.0 | 0.0 | | |
| FOXTAIL, GREEN | 1.0 | 0.0 | 0.0 | 0.0 | 0.0 | 0.0 | | |
| NUTSEDGE, PURPLE | 0.0 | 0.0 | 0.0 | 0.0 | 0.0 | 0.0 | | |
| OAT, WILD | 0.0 | 0.0 | 0.0 | 0.0 | 0.0 | 0.0 | | |
| COCKLEBUR | 9.0 | 2.0 | 0.0 | 0.0 | 0.0 | 0.0 | | |
| JIMSONWEED | 9.0 | 9.0 | 9.0 | 0.0 | 0.0 | 0.0 | | |
| LAMBSQUARTERS, C | 9.0 | 8.0 | 0.0 | 0.0 | 0.0 | 0.0 | | |
| MORNINGGLORY SPP | 9.0 | 4.0 | 3.0 | 0.0 | 0.0 | 0.0 | | |
| MUSTARD, WILD | 9.0 | 9.0 | 9.0 | 0.0 | 0.0 | 0.0 | | |
| PIGWEED, REDROOT | 9.0 | 7.0 | | 0.0 | 0.0 | 0.0 | | |
| RAGWEED, COMMON | 9.0 | 9.0 | 9.0 | 0.0 | 0.0 | 0.0 | | |
| VELVETLEAF | 3.0 | 0.0 | 0.0 | 9.9 | 0.0 | 0.0 | | |
| BARLEY, UNSPECIF | 0.0 | 0.0 | 0.0 | 0.0 | 0.0 | 0.0 | | |
| CORN, FIELD | 0.0 | 0.0 | 0.0 | 0.0 | 0.0 | 0.0 | | |
| RICE, UPLAND | 4.0 | 0.0 | 0.0 | 0.0 | 0.0 | 0.0 | | |
| SORGHUM, GRAIN | 0.0 | 0.0 | 0.0 | 0.0 | 0.0 | 0.0 | | |
| SOYBEAN | 9.0 | 0.0 | 0.0 | 0.0 | 0.0 | 0.0 | | |
| WHEAT, SPRING, X | 0.0 | 0.0 | 0.0 | 0.0 | 0.0 | 0.0 | | |
| 1,1-Dimethyl-3-[3-nitro-4-(phenethyloxy)phenyl]urea | | | | | | | | |
| BARNYARDGRASS | 1.0 | 0.0 | 0.0 | 0.0 | 0.0 | 0.0 | | |
| FOXTAIL, GREEN | 4.0 | 4.5 | 2.0 | 0.5 | 0.5 | 0.0 | 0.0 | |
| NUTSEDGE, PURPLE | 1.0 | 0.0 | 0.0 | 0.0 | 0.0 | 1.0 | | |
| OAT, WILD | 2.0 | 1.0 | 0.0 | 0.0 | 0.0 | 0.0 | | |
| BINDWEED, FIELD | | 9.0 | 9.0 | 4.0 | 1.0 | 0.0 | 0.0 | |
| COCKLEBUR | 9.0 | 8.5 | 8.5 | 8.0 | 6.5 | 8.0 | 2.0 | |
| JIMSONWEED | 2.0 | 5.0 | 5.0 | 4.5 | 4.5 | 4.5 | 0.0 | |
| LAMBSQUARTERS, C | 8.0 | 8.5 | 8.5 | 8.0 | 5.0 | 1.0 | 0.0 | |
| MORNINGGLORY SPP | 9.0 | 9.0 | 9.0 | 9.0 | 5.0 | 6.5 | 0.0 | |
| MUSTARD, WILD | 9.0 | 9.0 | 9.0 | 9.0 | 8.5 | 8.0 | 0.0 | |
| PIGWEED, REDROOT | 7.0 | 8.0 | 8.0 | 8.0 | 4.0 | 8.0 | | |
| PIGWEED SPP. | | 9.0 | 9.0 | 9.0 | 5.0 | 0.0 | 0.0 | |
| RAGWEED, COMMON | 9.0 | 9.0 | 9.0 | 8.5 | 8.0 | 7.5 | 0.0 | |
| THISTLE, CANADA | | 9.0 | 9.0 | 7.0 | 3.0 | 0.0 | 0.0 | |
| VELVETLEAF | 9.0 | 8.5 | 6.0 | 2.0 | 1.5 | 1.0 | 0.0 | |
| BARLEY, UNSPECIF | 4.0 | 3.0 | 2.0 | 2.0 | 2.0 | 0.0 | | |
| SUGAR-BEET | | 9.0 | 9.0 | 9.0 | 9.0 | 4.0 | 3.0 | |
| CORN, FIELD | 2.0 | 5.5 | 5.5 | 5.5 | 5.0 | 5.0 | 2.0 | |
| COTTON | | 8.0 | 1.0 | 2.0 | 1.0 | 1.0 | 0.0 | |
| RICE, UPLAND | 1.0 | 1.0 | 0.0 | 0.0 | 0.0 | 0.0 | | |
| RICE, SATURN | | 4.0 | 1.0 | 1.0 | 1.0 | 0.0 | 0.0 | |
| SORGHUM, GRAIN | 2.0 | 2.0 | 1.0 | 1.0 | 0.0 | 0.0 | | |
| SOYBEAN | 9.0 | 8.0 | 2.3 | 1.3 | 0.0 | 0.0 | 0.0 | |
| WHEAT, SPRING, X | 2.0 | 2.0 | 1.0 | 1.0 | 1.0 | 0.0 | | |
| WHEAT, SPRING, E | | 1.0 | 0.0 | 0.0 | 0.0 | 0.0 | 0.0 | |
| 3-{3-Chloro-4-[3-(4-methoxyphenyl)propoxy]-phenyl}-1,1-dimethylurea | | | | | | | | |
| BARNYARDGRASS | 0.0 | 0.0 | 0.0 | 0.0 | 0.0 | 0.0 | | |
| FOXTAIL, GREEN | 1.0 | 0.0 | 0.0 | 0.0 | 0.0 | 0.0 | | |
| NUTSEDGE, PURPLE | 0.0 | 0.0 | 0.0 | 0.0 | 0.0 | 0.0 | | |
| OAT, WILD | 0.0 | 0.0 | 0.0 | 0.0 | 0.0 | 0.0 | | |

TABLE III-continued

Evaluation of the Selective Postemergence Broadleaf Herbicidal Activity of the Compounds of the Invention in the Presence of Graminaceous Crops, Soybeans and Cotton

| Rate (kg/ha): | 2.000 | 1.000 | .500 | .250 | .125 | .063 | .032 | .016 |
|---|---|---|---|---|---|---|---|---|
| COCKLEBUR | 9.0 | 9.0 | 9.0 | 5.0 | 5.0 | 3.0 | | |
| JIMSONWEED | 9.0 | 0.0 | 0.0 | 0.0 | 0.0 | 0.0 | | |
| LAMBSQUARTERS, C | 8.0 | 8.0 | 8.0 | 1.0 | 0.0 | 0.0 | | |
| MORNINGGLORY SPP | 0.0 | 4.0 | 0.0 | 0.0 | 0.0 | 0.0 | | |
| MUSTARD, WILD | 9.0 | 9.0 | 9.0 | 9.0 | 9.0 | 9.0 | | |
| PIGWEED, REDROOT | 4.0 | 4.0 | 4.0 | 2.0 | | 0.0 | | |
| RAGWEED, COMMON | 2.0 | 1.0 | 0.0 | 0.0 | 0.0 | 0.0 | | |
| VELVETLEAF | 0.0 | 0.0 | 0.0 | 0.0 | 0.0 | 0.0 | | |
| BARLEY, UNSPECIF | 0.0 | 0.0 | 0.0 | 0.0 | 0.0 | 0.0 | | |
| CORN, FIELD | 0.0 | 0.0 | 0.0 | 0.0 | 0.0 | 0.0 | | |
| RICE, UPLAND | 0.0 | 0.0 | 0.0 | 0.0 | 0.0 | 0.0 | | |
| SORGHUM, GRAIN | 0.0 | 0.0 | 0.0 | 0.0 | 0.0 | 0.0 | | |
| SOYBEAN | 0.0 | 0.0 | 0.0 | 0.0 | 0.0 | 0.0 | | |
| WHEAT, SPRING, X | 0.0 | 0.0 | 0.0 | 0.0 | 0.0 | 0.0 | | |
| 3-[3-Chloro-4-(3-phenylbutoxy)phenyl]-1,1-dimethylurea | | | | | | | | |
| BARNYARDGRASS | 0.0 | 0.0 | 0.0 | 0.0 | 0.0 | 0.0 | | |
| FOXTAIL, GREEN | 4.0 | 4.0 | 4.0 | 1.0 | 1.0 | 1.0 | | |
| NUTSEDGE, PURPLE | 3.0 | 3.0 | 5.0 | 1.0 | 0.0 | 0.0 | | |
| OAT, WILD | 0.0 | 0.0 | 0.0 | 0.0 | 0.0 | 0.0 | | |
| COCKLEBUR | 9.0 | 9.0 | 9.0 | 0.0 | 0.0 | 0.0 | | |
| JIMSONWEED | 0.0 | 0.0 | 0.0 | 0.0 | 0.0 | 0.0 | | |
| LAMBSQUARTERS, C | 9.0 | 9.0 | 9.0 | | 8.0 | 2.0 | | |
| MORNINGGLORY SPP | 9.0 | 0.0 | | 0.0 | 0.0 | 0.0 | | |
| MUSTARD, WILD | 9.0 | 9.0 | 9.0 | 9.0 | 9.0 | 8.0 | | |
| PIGWEED, REDROOT | 9.0 | 9.0 | 9.0 | 9.0 | 3.0 | 0.0 | | |
| RAGWEED, COMMON | 9.0 | 9.0 | 9.0 | 9.0 | 9.0 | 2.0 | | |
| VELVETLEAF | 3.0 | 2.0 | 1.0 | 0.0 | 0.0 | 0.0 | | |
| BARLEY, UNSPECIF | 1.0 | 1.0 | 0.0 | 0.0 | 0.0 | 0.0 | | |
| CORN, FIELD | 1.0 | 0.0 | 0.0 | 0.0 | 0.0 | 0.0 | | |
| RICE, UPLAND | 2.0 | 2.0 | 1.0 | 1.0 | 0.0 | 0.0 | | |
| SORGHUM, GRAIN | 1.0 | 1.0 | 0.0 | 0.0 | 0.0 | 0.0 | | |
| SOYBEAN | 9.0 | 3.0 | 1.0 | 0.0 | 0.0 | 0.0 | | |
| WHEAT, SPRING, X | 8.0 | 0.0 | 0.0 | 0.0 | 0.0 | 0.0 | | |
| 3-[3-Chloro-4-(7-phenylheptyloxy)phenyl]-1,1-dimethylurea | | | | | | | | |
| BARNYARDGRASS | 0.0 | 0.0 | 0.0 | 0.0 | 0.0 | 0.0 | | |
| FOXTAIL, GREEN | 3.0 | 2.0 | 2.0 | 1.0 | 0.0 | 0.0 | | |
| NUTSEDGE, PURPLE | 0.0 | 0.0 | 0.0 | 0.0 | 0.0 | 0.0 | | |
| OAT, WILD | 0.0 | 0.0 | 0.0 | 0.0 | 0.0 | 0.0 | | |
| COCKLEBUR | 0.0 | 0.0 | 8.0 | 3.0 | 0.0 | 0.0 | | |
| JIMSONWEED | 0.0 | 0.0 | 0.0 | 0.0 | 0.0 | 0.0 | | |
| LAMBSQUARTERS, C | 1.0 | 0.0 | 0.0 | 0.0 | 0.0 | 0.0 | | |
| MORNINGGLORY SPP | 0.0 | 0.0 | 0.0 | 0.0 | 0.0 | 0.0 | | |
| MUSTARD, WILD | 8.0 | 9.0 | 9.0 | 7.0 | 6.0 | 0.0 | | |
| PIGWEED, REDROOT | 1.0 | 1.0 | 1.0 | 1.0 | 0.0 | 0.0 | | |
| RAGWEED, COMMON | 0.0 | 0.0 | 0.0 | 0.0 | 0.0 | 0.0 | | |
| VELVETLEAF | 0.0 | 0.0 | 0.0 | 0.0 | 0.0 | 0.0 | | |
| BARLEY, UNSPECIF | 0.0 | 0.0 | 0.0 | 0.0 | 0.0 | 0.0 | | |
| CORN, FIELD | 0.0 | 0.0 | 0.0 | 0.0 | 0.0 | 0.0 | | |
| RICE, UPLAND | 0.0 | 0.0 | 0.0 | 0.0 | 0.0 | 0.0 | | |
| SORGHUM, GRAIN | 0.0 | 0.0 | 0.0 | 0.0 | 0.0 | 0.0 | | |
| SOYBEAN | 0.0 | 0.0 | 0.0 | 0.0 | 0.0 | 0.0 | | |
| WHEAT, SPRING, X | 0.0 | 0.0 | 0.0 | 0.0 | 0.0 | 0.0 | | |
| 3-[3-Chloro-4-(8-phenyloctyloxy)phenyl]-1,1-dimethylurea | | | | | | | | |
| BARNYARDGRASS | 0.0 | 0.0 | 0.0 | 0.0 | 0.0 | 0.0 | | |
| FOXTAIL, GREEN | 3.0 | 3.0 | 3.0 | 1.0 | 1.0 | 1.0 | | |
| NUTSEDGE, PURPLE | 0.0 | 0.0 | 0.0 | 0.0 | 0.0 | 0.0 | | |
| OAT, WILD | 0.0 | 0.0 | 0.0 | 0.0 | 0.0 | 0.0 | | |
| COCKLEBUR | 9.0 | 8.0 | | 0.0 | 0.0 | 0.0 | | |
| JIMSONWEED | 0.0 | | 0.0 | 0.0 | 0.0 | 0.0 | | |
| LAMBSQUARTERS, C | 5.0 | 5.0 | 3.0 | 3.0 | 0.0 | 0.0 | | |
| MORNINGGLORY SPP | 0.0 | 0.0 | 0.0 | 0.0 | 0.0 | 0.0 | | |
| MUSTARD, WILD | 4.0 | 9.0 | 7.0 | 9.0 | 7.0 | 0.0 | | |
| PIGWEED, REDROOT | 7.0 | 6.0 | 2.0 | 4.0 | 0.0 | 0.0 | | |
| RAGWEED, COMMON | 8.0 | 0.0 | 0.0 | 0.0 | 0.0 | 0.0 | | |
| VELVETLEAF | 0.0 | 0.0 | 0.0 | 0.0 | 0.0 | 0.0 | | |
| BARLEY, UNSPECIF | 0.0 | 0.0 | 0.0 | 0.0 | 0.0 | 0.0 | | |
| CORN, FIELD | 0.0 | 0.0 | 0.0 | 0.0 | 0.0 | 0.0 | | |
| RICE, UPLAND | 0.0 | 0.0 | 0.0 | 0.0 | 0.0 | 0.0 | | |
| SORGHUM, GRAIN | 0.0 | 0.0 | 0.0 | 0.0 | 0.0 | 0.0 | | |
| SOYBEAN | 0.0 | 0.0 | 0.0 | 0.0 | 0.0 | 0.0 | | |
| WHEAT, SPRING, X | 0.0 | 0.0 | 0.0 | 0.0 | 0.0 | 0.0 | | |
| 3-[3-Chloro-4-(1-methyl-3-phenylpropoxy)phenyl]-1,1-dimethylurea | | | | | | | | |
| BARNYARDGRASS | 0.0 | 0.0 | 0.0 | 0.0 | 0.0 | 0.0 | | |
| FOXTAIL, GREEN | 2.0 | 3.5 | 4.0 | 4.5 | 0.5 | 0.0 | 0.0 | |
| NUTSEDGE, PURPLE | 6.0 | 4.0 | 1.0 | 0.0 | 0.0 | 0.0 | | |
| OAT, WILD | 0.0 | 0.0 | 0.0 | 0.0 | 0.0 | 0.0 | | |

TABLE III-continued

Evaluation of the Selective Postemergence Broadleaf Herbicidal Activity of the Compounds of the Invention in the Presence of Graminaceous Crops, Soybeans and Cotton

| Rate (kg/ha): | 2.000 | 1.000 | .500 | .250 | .125 | .063 | .032 | .016 |
|---|---|---|---|---|---|---|---|---|
| BINDWEED, FIELD |  | 6.0 | 5.0 | 8.0 | 0.0 | 0.0 | 0.0 |  |
| COCKLEBUR | 9.0 | 9.0 | 9.0 | 6.0 | 3.0 | 3.0 | 6.0 |  |
| JIMSONWEED | 9.0 | 4.5 | 5.0 | 9.0 | 9.0 | 4.5 | 4.0 |  |
| LAMBSQUARTERS, C | 9.0 | 9.0 | 9.0 | 6.5 | 5.5 | 1.0 | 0.0 |  |
| MORNINGGLORY SPP | 9.0 | 9.0 | 9.0 | 6.5 | 5.5 | 1.0 | 0.0 |  |
| MUSTARD, WILD | 9.0 | 9.0 | 9.0 | 9.0 | 9.0 | 4.5 | 0.0 |  |
| PIGWEED, REDROOT | 9.0 | 9.0 | 9.0 | 9.0 | 9.0 | 9.0 |  |  |
| PIGWEED SPP. |  | 9.0 | 9.0 | 3.0 | 0.0 | 3.0 | 0.0 |  |
| RAGWEED, COMMON | 7.0 | 6.5 | 6.0 | 5.0 | 2.5 | 1.5 | 0.0 |  |
| THISTLE, CANADA |  | 9.0 | 3.0 | 1.0 | 0.0 | 0.0 | 0.0 |  |
| VELVETLEAF | 9.0 | 5.5 | 5.5 | 2.0 | 1.5 | 0.0 | 0.0 |  |
| BARLEY, UNSPECIF | 0.0 | 0.0 | 0.0 | 0.0 | 0.0 | 0.0 |  |  |
| SUGAR-BEET |  | 9.0 | 9.0 | 9.0 | 9.0 | 3.0 | 1.0 |  |
| CORN, FIELD | 0.0 | 6.0 | 5.5 | 5.0 | 2.5 | 0.0 | 0.0 |  |
| COTTON |  | 7.0 | 7.0 | 0.0 | 0.0 | 0.0 | 0.0 |  |
| RICE, UPLAND | 0.0 | 0.0 | 0.0 | 0.0 | 0.0 | 0.0 |  |  |
| RICE, SATURN |  | 3.0 | 2.0 | 0.0 | 0.0 | 0.0 | 0.0 |  |
| SORGHUM, GRAIN | 0.0 | 0.0 | 0.0 | 0.0 | 0.0 | 0.0 |  |  |
| SOYBEAN | 0.0 | 4.8 | 1.8 | 0.3 | 0.0 | 0.0 | 0.0 |  |
| WHEAT, SPRING, X | 0.0 | 0.0 | 0.0 | 0.0 | 0.0 | 0.0 |  |  |
| WHEAT, SPRING, E |  | 1.0 | 0.0 | 0.0 | 0.0 | 0.0 | 0.0 |  |
| 3-[3-Chloro-4-(β-ethylphenethyloxy)phenyl]-1,1-dimethylurea | | | | | | | | |
| BARNYARDGRASS | 0.0 | 0.0 | 0.0 | 0.0 | 0.0 | 0.0 |  |  |
| FOXTAIL, GREEN | 0.0 | 0.0 | 0.0 | 0.0 | 0.0 | 0.0 |  |  |
| NUTSEDGE, PURPLE | 0.0 | 0.0 | 0.0 | 0.0 | 0.0 | 0.0 |  |  |
| OAT, WILD | 0.0 | 0.0 | 0.0 | 0.0 | 0.0 | 0.0 |  |  |
| JIMSONWEED | 9.0 | 0.0 | 0.0 | 0.0 | 0.0 | 0.0 |  |  |
| LAMBSQUARTERS, C | 9.0 | 9.0 | 9.0 | 9.0 | 9.0 | 9.0 |  |  |
| MORNINGGLORY SPP | 9.0 | 9.0 | 0.0 |  | 0.0 | 0.0 |  |  |
| MUSTARD, WILD | 9.0 | 9.0 | 9.0 | 9.0 | 9.0 | 9.0 |  |  |
| PIGWEED, REDROOT | 9.0 | 9.0 | 9.0 | 6.0 | 6.0 |  |  |  |
| RAGWEED, COMMON | 9.0 | 9.0 | 9.0 | 9.0 | 7.0 | 3.0 |  |  |
| VELVETLEAF | 2.0 | 0.0 | 0.0 | 0.0 | 0.0 | 0.0 |  |  |
| BARLEY, UNSPECIF | 0.0 | 0.0 | 0.0 | 0.0 | 0.0 | 0.0 |  |  |
| CORN, FIELD | 0.0 | 0.0 | 0.0 | 0.0 | 0.0 | 0.0 |  |  |
| RICE, UPLAND | 1.0 | 0.0 | 0.0 | 0.0 | 0.0 | 0.0 |  |  |
| SORGHUM, GRAIN | 0.0 | 0.0 | 0.0 | 0.0 | 0.0 | 0.0 |  |  |
| SOYBEAN | 7.0 | 6.0 | 1.0 | 0.0 | 0.0 | 0.0 |  |  |
| WHEAT, SPRING, X | 0.0 | 0.0 | 0.0 | 0.0 | 0.0 | 0.0 |  |  |
| 1-[3-Chloro-4-(phenethyloxy)phenyl]-3-ethylurea | | | | | | | | |
| BARNYARDGRASS | 0.0 | 0.0 | 0.0 | 0.0 | 0.0 | 0.0 |  |  |
| FOXTAIL, GREEN | 0.0 | 0.0 | 0.0 | 0.0 | 0.0 | 0.0 |  |  |
| NUTSEDGE, PURPLE | 0.0 | 0.0 | 0.0 | 0.0 | 0.0 | 0.0 |  |  |
| OAT, WILD | 0.0 | 0.0 | 0.0 | 0.0 | 0.0 | 0.0 |  |  |
| COCKLEBUR | 9.0 | 9.0 | 8.0 | 9.0 |  |  |  |  |
| LAMBSQUARTERS, C | 8.0 | 8.0 | 8.0 | 0.0 | 0.0 | 0.0 |  |  |
| MORNINGGLORY SPP | 3.0 | 2.0 | 1.0 | 0.0 | 0.0 | 0.0 |  |  |
| MUSTARD, WILD | 9.0 | 9.0 | 9.0 | 9.0 | 9.0 | 9.0 |  |  |
| PIGWEED, REDROOT | 9.0 | 9.0 | 6.0 | 6.0 | 3.0 | 2.0 |  |  |
| RAGWEED, COMMON | 0.0 | 0.0 | 0.0 | 0.0 | 0.0 | 0.0 |  |  |
| VELVETLEAF | 0.0 | 0.0 | 0.0 | 0.0 | 0.0 | 0.0 |  |  |
| BARLEY, UNSPECIF | 0.0 | 0.0 | 0.0 | 0.0 | 0.0 | 0.0 |  |  |
| CORN, FIELD | 0.0 | 0.0 | 0.0 | 0.0 | 0.0 | 0.0 |  |  |
| RICE, UPLAND | 0.0 | 0.0 | 0.0 | 0.0 | 0.0 | 0.0 |  |  |
| SORGHUM, GRAIN | 0.0 | 0.0 | 0.0 | 0.0 | 0.0 | 0.0 |  |  |
| SOYBEAN | 7.0 | 0.0 | 0.0 | 0.0 | 0.0 | 0.0 |  |  |
| WHEAT, SPRING, X | 0.0 | 0.0 | 0.0 | 0.0 | 0.0 | 0.0 |  |  |
| 3-[3-Chloro-4-(phenethyloxy)phenyl]-1,1-dimethyl-2-thiourea | | | | | | | | |
| BARNYARDGRASS | 0.0 | 0.0 | 0.0 | 0.0 | 0.0 | 0.0 |  |  |
| FOXTAIL, GREEN | 6.0 | 3.0 | 2.5 | 1.0 | 1.0 | 0.5 | 0.0 |  |
| NUTSEDGE, PURPLE | 1.0 | 0.0 | 0.0 | 0.0 | 0.0 | 0.0 |  |  |
| OAT, WILD | 0.0 | 0.0 | 0.0 | 0.0 | 0.0 | 0.0 |  |  |
| BINDWEED, FIELD |  | 0.0 | 0.0 | 0.0 | 0.0 | 0.0 | 0.0 |  |
| COCKLEBUR | 9.0 | 9.0 | 9.0 | 8.0 | 7.0 | 7.0 | 0.0 |  |
| JIMSONWEED | 9.0 | 9.0 | 9.0 | 1.0 | 0.0 | 0.0 | 0.0 |  |
| LAMBSQUARTERS, C | 9.0 | 8.5 | 8.5 | 2.5 | 2.5 | 1.5 | 0.0 |  |
| MORNINGGLORY SPP | 0.0 | 4.5 | 4.5 | 4.5 | 4.5 | 0.0 | 0.0 |  |
| MUSTARD, WILD | 9.0 | 8.0 | 9.0 | 9.0 | 8.0 | 5.0 | 0.0 |  |
| PIGWEED, REDROOT | 9.0 | 9.0 | 9.0 | 3.0 | 0.0 | 0.0 |  |  |
| PIGWEED SPP. |  | 9.0 | 9.0 | 2.0 | 0.0 | 0.0 | 0.0 |  |
| RAGWEED, COMMON | 9.0 | 6.0 | 5.5 | 1.5 | 1.0 | 0.0 | 0.0 |  |
| THISTLE, CANADA |  | 9.0 | 9.0 | 3.0 | 0.0 | 0.0 | 0.0 |  |
| VELVETLEAF | 0.0 | 0.5 | 0.5 | 0.0 | 0.0 | 0.0 | 0.0 |  |
| BARLEY, UNSPECIF | 0.0 | 0.0 | 0.0 | 0.0 | 0.0 | 0.0 |  |  |
| SUGAR-BEET |  | 0.0 | 9.0 | 8.0 | 0.0 | 2.0 | 0.0 |  |
| CORN, FIELD | 0.0 | 4.5 | 4.5 | 4.5 | 4.5 | 4.5 | 0.0 |  |

TABLE III-continued

Evaluation of the Selective Postemergence Broadleaf Herbicidal Activity of the Compounds of the Invention in the Presence of Graminaceous Crops, Soybeans and Cotton

| Rate (kg/ha): | 2.000 | 1.000 | .500 | .250 | .125 | .063 | .032 | .016 |
|---|---|---|---|---|---|---|---|---|
| COTTON | | 8.0 | 0.0 | 0.0 | 2.0 | 0.0 | 0.0 | |
| RICE, UPLAND | 0.0 | 0.0 | 0.0 | 0.0 | 0.0 | 0.0 | | |
| RICE, SATURN | | 1.0 | 2.0 | 2.0 | 0.0 | 0.0 | 0.0 | |
| SORGHUM, GRAIN | 0.0 | 8.0 | 0.0 | 0.0 | 0.0 | 0.0 | | |
| SOYBEAN | 0.0 | 0.3 | 1.0 | 0.0 | 0.0 | 0.0 | 0.0 | |
| WHEAT, SPRING, X | 0.0 | 0.0 | 0.0 | 0.0 | 0.0 | 0.0 | | |
| WHEAT, SPRING, E | | 0.0 | 0.0 | 0.0 | 0.0 | 0.0 | 0.0 | |
| 3-{3-Chloro-4-[2-(2-naphthyl)ethoxy]phenyl}-1,1-dimethylurea | | | | | | | | |
| BARNYARDGRASS | 0.0 | 0.0 | 0.0 | 0.0 | 0.0 | 0.0 | | |
| FOXTAIL, GREEN | 0.0 | 0.0 | 0.0 | 0.0 | 0.0 | 0.0 | | |
| NUTSEDGE, PURPLE | 0.0 | 0.0 | 0.0 | 0.0 | 0.0 | 0.0 | | |
| OAT, WILD | 0.0 | 0.0 | 0.0 | 0.0 | 0.0 | 0.0 | | |
| COCKLEBUR | 2.0 | 2.0 | 2.0 | 8.0 | 0.0 | 0.0 | | |
| LAMBSQUARTERS, C | 6.0 | 3.0 | 2.0 | 1.0 | 0.0 | 0.0 | | |
| MORNINGGLORY SPP | 1.0 | 0.0 | 0.0 | 0.0 | 0.0 | 0.0 | | |
| MUSTARD, WILD | 8.0 | 4.0 | 4.0 | 4.0 | 0.0 | 0.0 | | |
| PIGWEED, REDROOT | 3.0 | 1.0 | 0.0 | 0.0 | 0.0 | 0.0 | | |
| RAGWEED, COMMON | 9.0 | 3.0 | 1.0 | 0.0 | 0.0 | 0.0 | | |
| VELVETLEAF | 1.0 | 0.0 | 0.0 | 0.0 | 0.0 | 0.0 | | |
| BARLEY, UNSPECIF | 0.0 | 0.0 | 0.0 | 0.0 | 0.0 | 0.0 | | |
| CORN, FIELD | 0.0 | 0.0 | 0.0 | 0.0 | 0.0 | 0.0 | | |
| RICE, UPLAND | 2.0 | 0.0 | 0.0 | 0.0 | 0.0 | 0.0 | | |
| SORGHUM, GRAIN | 0.0 | 0.0 | 0.0 | 0.0 | 0.0 | 0.0 | | |
| SOYBEAN | 2.0 | 0.0 | 0.0 | 0.0 | 0.0 | 0.0 | | |
| WHEAT, SPRING, X | 0.0 | 0.0 | 0.0 | 0.0 | 0.0 | 0.0 | | |
| 3-{3-Chloro-4-[(3,4-dimethoxyphenethyl)oxy]phenyl}-1,1-dimethylurea | | | | | | | | |
| BARNYARDGRASS | 0.0 | 0.0 | 0.0 | 0.0 | 0.0 | 0.0 | | |
| FOXTAIL, GREEN | 0.0 | 0.0 | 0.0 | 0.0 | 0.0 | 0.0 | | |
| NUTSEDGE, PURPLE | 0.0 | 0.0 | 0.0 | 0.0 | 0.0 | 0.0 | | |
| OAT, WILD | 0.0 | 0.0 | 0.0 | 0.0 | 0.0 | 0.0 | | |
| COCKLEBUR | 9.0 | 9.0 | 2.0 | 2.0 | 0.0 | 0.0 | | |
| JIMSONWEED | | | | | 0.0 | 0.0 | | |
| LAMBSQUARTERS, C | 8.0 | 6.0 | 6.0 | 3.0 | 1.0 | 0.0 | | |
| MORNINGGLORY SPP | 2.0 | 1.0 | 4.0 | 0.0 | 0.0 | 0.0 | | |
| MUSTARD, WILD | | | | | 0.0 | 0.0 | | |
| PIGWEED, REDROOT | 1.0 | 1.0 | 0.0 | 0.0 | 0.0 | 0.0 | | |
| RAGWEED, COMMON | 9.0 | 0.0 | 6.0 | 0.0 | 0.0 | 0.0 | | |
| VELVETLEAF | 0.0 | 0.0 | 0.0 | 0.0 | 0.0 | 0.0 | | |
| BARLEY, UNSPECIF | 0.0 | 0.0 | 0.0 | 0.0 | 0.0 | 0.0 | | |
| CORN, FIELD | 0.0 | 0.0 | 0.0 | 0.0 | 0.0 | 0.0 | | |
| RICE, UPLAND | 2.0 | 0.0 | 2.0 | 0.0 | 0.0 | 0.0 | | |
| SORGHUM, GRAIN | 0.0 | 0.0 | 0.0 | 0.0 | 0.0 | 0.0 | | |
| SOYBEAN | 0.0 | 0.0 | 0.0 | 0.0 | 0.0 | 0.0 | | |
| WHEAT, SPRING, X | 0.0 | 0.0 | 0.0 | 0.0 | 0.0 | 0.0 | | |
| 1-[3-Chloro-4-(phenethyloxy)phenyl]-3-methyl-2-thiourea | | | | | | | | |
| BARNYARDGRASS | 3.0 | 0.0 | 0.0 | 0.0 | 0.0 | 0.0 | | |
| FOXTAIL, GREEN | 0.0 | 0.0 | 0.0 | 0.0 | 0.0 | 0.0 | | |
| NUTSEDGE, PURPLE | 0.0 | 0.0 | 0.0 | 0.0 | 0.0 | 0.0 | | |
| OAT, WILD | 1.0 | 0.0 | 0.0 | 0.0 | 0.0 | 0.0 | | |
| COCKLEBUR | 0.0 | 0.0 | 0.0 | 0.0 | 0.0 | 0.0 | | |
| JIMSONWEED | 9.0 | 9.0 | 0.0 | 0.0 | 0.0 | 0.0 | | |
| LAMBSQUARTERS, C | 9.0 | 9.0 | 9.0 | 4.0 | 2.0 | 1.0 | | |
| MORNINGGLORY SPP | 6.0 | 9.0 | 9.0 | 6.0 | 6.0 | 0.0 | | |
| MUSTARD, WILD | 9.0 | 9.0 | 9.0 | 4.0 | 3.0 | 0.0 | | |
| PIGWEED, REDROOT | 9.0 | 6.0 | 0.0 | 0.0 | 0.0 | 0.0 | | |
| RAGWEED, COMMON | 9.0 | 9.0 | 9.0 | 8.0 | 0.0 | 0.0 | | |
| VELVETLEAF | 9.0 | 9.0 | 9.0 | 0.0 | 0.0 | 0.0 | | |
| BARLEY, UNSPECIF | 0.0 | 0.0 | 0.0 | 0.0 | 0.0 | 0.0 | | |
| CORN, FIELD | 1.0 | 0.0 | 0.0 | 0.0 | 0.0 | 0.0 | | |
| RICE, UPLAND | 8.0 | 3.0 | 3.0 | 3.0 | 1.0 | 1.0 | | |
| SOYBEAN | 9.0 | 9.0 | 9.0 | 3.0 | 9.0 | 4.0 | | |
| WHEAT, SPRING, X | 0.0 | 0.0 | 0.0 | 0.0 | 0.0 | 0.0 | | |
| 1-[3-Chloro-4-(phenethylthio)phenyl]-3-methylurea | | | | | | | | |
| BARNYARDGRASS | 0.0 | 0.0 | 0.0 | 0.0 | 0.0 | 0.0 | | |
| FOXTAIL, GREEN | 0.0 | 0.0 | 0.0 | 0.0 | 0.0 | 0.0 | | |
| NUTSEDGE, PURPLE | 0.0 | 0.0 | 0.0 | 0.0 | 0.0 | 0.0 | | |
| OAT, WILD | 0.0 | 0.0 | 0.0 | 0.0 | 0.0 | 0.0 | | |
| COCKLEBUR | 0.0 | 0.0 | 0.0 | 0.0 | 0.0 | 0.0 | | |
| JIMSONWEED | 0.0 | 0.0 | 0.0 | 0.0 | 0.0 | 0.0 | | |
| LAMBSQUARTERS, C | 9.0 | 9.0 | 0.0 | | | | | |
| MORNINGGLORY SPP | 9.0 | 2.0 | 0.0 | 0.0 | 0.0 | 0.0 | | |
| MUSTARD, WILD | 9.0 | 9.0 | 9.0 | 0.0 | 0.0 | 0.0 | | |
| PIGWEED, REDROOT | 9.0 | 8.0 | 0.0 | 0.0 | 0.0 | 0.0 | | |
| RAGWEED, COMMON | 9.0 | 9.0 | 0.0 | | 0.0 | 0.0 | | |
| VELVETLEAF | 0.0 | 0.0 | 0.0 | 0.0 | 0.0 | 0.0 | | |
| BARLEY, UNSPECIF | 0.0 | 0.0 | 0.0 | 0.0 | 0.0 | 0.0 | | |

TABLE III-continued

Evaluation of the Selective Postemergence Broadleaf Herbicidal Activity of the Compounds of the Invention in the Presence of Graminaceous Crops, Soybeans and Cotton (Rates are given in kg/ha)

| Rate (kg/ha): | 2.000 | 1.000 | .500 | .250 | .125 | .063 | .032 | .016 |
|---|---|---|---|---|---|---|---|---|
| CORN, FIELD | 0.0 | 0.0 | 0.0 | 0.0 | 0.0 | 0.0 | | |
| RICE, UPLAND | 0.0 | 0.0 | 0.0 | 0.0 | 0.0 | 0.0 | | |
| SORGHUM, GRAIN | 0.0 | 0.0 | 0.0 | 0.0 | 0.0 | 0.0 | | |
| SOYBEAN | 0.0 | 0.0 | 0.0 | 0.0 | 0.0 | 0.0 | | |
| WHEAT, SPRING, X | 0.0 | 0.0 | 0.0 | 0.0 | 0.0 | 0.0 | | |

1-Butyl-3-[3-chloro-4-(phenethyloxy)phenyl]urea

| | 2.000 | 1.000 | .500 | .250 | .125 | .063 | | |
|---|---|---|---|---|---|---|---|---|
| BARNYARDGRASS | 0.0 | 0.0 | 0.0 | 0.0 | 0.0 | 0.0 | | |
| FOXTAIL, GREEN | 0.0 | 0.0 | 0.0 | 0.0 | 0.0 | 0.0 | | |
| NUTSEDGE, PURPLE | 0.0 | 0.0 | 0.0 | 0.0 | 0.0 | 0.0 | | |
| OAT, WILD | 0.0 | 0.0 | 0.0 | 0.0 | 0.0 | 0.0 | | |
| COCKLEBUR | 0.0 | 0.0 | 0.0 | 0.0 | 0.0 | 0.0 | | |
| JIMSONWEED | 0.0 | 0.0 | 0.0 | 0.0 | 0.0 | 0.0 | | |
| LAMBSQUARTERS, C | 7.0 | 4.0 | 3.0 | 3.0 | 0.0 | 0.0 | | |
| MORNINGGLORY SPP | 0.0 | 0.0 | 0.0 | 0.0 | 0.0 | 0.0 | | |
| MUSTARD, WILD | 0.0 | 0.0 | 0.0 | 0.0 | 0.0 | 0.0 | | |
| PIGWEED, REDROOT | 3.0 | 3.0 | 0.0 | 0.0 | 0.0 | 0.0 | | |
| RAGWEED, COMMON | 8.0 | 0.0 | 0.0 | 0.0 | 0.0 | 0.0 | | |
| VELVETLEAF | 0.0 | 0.0 | 0.0 | 0.0 | 0.0 | 0.0 | | |
| BARLEY, UNSPECIF | 0.0 | 0.0 | 0.0 | 0.0 | 0.0 | 0.0 | | |
| CORN, FIELD | 0.0 | 0.0 | 0.0 | 0.0 | 0.0 | 0.0 | | |
| RICE, UPLAND | 0.0 | 0.0 | 0.0 | 0.0 | 0.0 | 0.0 | | |
| SORGHUM, GRAIN | 0.0 | 0.0 | 0.0 | 0.0 | 0.0 | 0.0 | | |
| SOYBEAN | 0.0 | 0.0 | 0.0 | 0.0 | 0.0 | 0.0 | | |
| WHEAT, SPRING, X | 0.0 | 0.0 | 0.0 | 0.0 | 0.0 | 0.0 | | |

1,1-Dimethyl-3-[4-(3-phenyl-2-propynyloxy)phenyl]urea

| | 2.000 | 1.000 | .500 | .250 | .125 | .063 | | |
|---|---|---|---|---|---|---|---|---|
| BARNYARDGRASS | 0.0 | 0.0 | 0.0 | 0.0 | 0.0 | 0.0 | | |
| FOXTAIL, GREEN | 0.0 | 0.0 | 0.0 | 0.0 | 0.0 | 0.0 | | |
| NUTSEDGE, PURPLE | 0.0 | 0.0 | 0.0 | 0.0 | 0.0 | 0.0 | | |
| OAT, WILD | 0.0 | 0.0 | 0.0 | 0.0 | 0.0 | 0.0 | | |
| COCKLEBUR | 9.0 | 9.0 | 9.0 | 9.0 | 9.0 | 0.0 | | |
| JIMSONWEED | 9.0 | 9.0 | 0.0 | | | | | |
| LAMBSQUARTERS, C | 9.0 | 9.0 | 8.0 | 7.0 | 3.0 | 1.0 | | |
| MORNINGGLORY SPP | 4.0 | 4.0 | 4.0 | 0.0 | 0.0 | 0.0 | | |
| MUSTARD, WILD | 9.0 | 9.0 | 6.0 | 9.0 | 0.0 | 0.0 | | |
| PIGWEED, REDROOT | 9.0 | 8.0 | 8.0 | 7.0 | 0.0 | 0.0 | | |
| RAGWEED, COMMON | 9.0 | 9.0 | 9.0 | 9.0 | 8.0 | 6.0 | | |
| VELVETLEAF | 0.0 | 0.0 | 0.0 | 0.0 | 0.0 | 0.0 | | |
| BARLEY, UNSPECIF | 0.0 | 0.0 | 0.0 | 0.0 | 0.0 | 0.0 | | |
| CORN, FIELD | 1.0 | 0.0 | 0.0 | 0.0 | 0.0 | 0.0 | | |
| RICE, UPLAND | 7.0 | 3.0 | 3.0 | 3.0 | 0.0 | 0.0 | | |
| SOYBEAN | 9.0 | 3.0 | | 0.0 | | 0.0 | | |
| WHEAT, SPRING, X | 4.0 | 1.0 | 0.0 | 0.0 | 0.0 | 0.0 | | |

1,1-Dimethyl-3-[4-(β-methylphenethyloxy)phenyl]urea

| | 2.000 | 1.000 | .500 | .250 | .125 | .063 | | |
|---|---|---|---|---|---|---|---|---|
| BARNYARDGRASS | 2.0 | 0.0 | 0.0 | 0.0 | 0.0 | 0.0 | | |
| FOXTAIL, GREEN | 1.0 | 1.0 | 0.0 | 0.0 | 0.0 | 0.0 | | |
| NUTSEDGE, PURPLE | 2.0 | 1.0 | 0.0 | 0.0 | 0.0 | 0.0 | | |
| OAT, WILD | 0.0 | 0.0 | 0.0 | 0.0 | 0.0 | 0.0 | | |
| COCKLEBUR | 9.0 | 9.0 | 9.0 | 9.0 | 9.0 | 9.0 | | |
| JIMSONWEED | 9.0 | 9.0 | 9.0 | 2.0 | 0.0 | 0.0 | | |
| LAMBSQUARTERS, C | 9.0 | 9.0 | 9.0 | 9.0 | 8.0 | 2.0 | | |
| MORNINGGLORY SPP | 9.0 | 9.0 | 9.0 | 9.0 | 9.0 | 9.0 | | |
| MUSTARD, WILD | 9.0 | 9.0 | 9.0 | 9.0 | 3.0 | 0.0 | | |
| PIGWEED, REDROOT | 9.0 | 9.0 | 9.0 | 9.0 | 8.0 | 2.0 | | |
| RAGWEED, COMMON | 9.0 | 9.0 | 9.0 | 9.0 | 9.0 | 9.0 | | |
| VELVETLEAF | 9.0 | 9.0 | 9.0 | 9.0 | 9.0 | 9.0 | | |
| BARLEY, UNSPECIF | 1.0 | 0.0 | 0.0 | 0.0 | 0.0 | 0.0 | | |
| CORN, FIELD | 9.0 | 2.0 | 1.0 | 0.0 | 0.0 | 0.0 | | |
| RICE, UPLAND | 9.0 | 8.0 | 6.0 | 4.0 | 4.0 | 0.0 | | |
| SOYBEAN | 9.0 | 9.0 | 9.0 | 9.0 | 9.0 | 9.0 | | |
| WHEAT, SPRING, X | 6.0 | 1.0 | 0.0 | 0.0 | 0.0 | 0.0 | | |

3-[3-Chloro-4-(α-ethylphenethyloxy)phenyl]-1,1-dimethylurea

| | 2.000 | 1.000 | .500 | .250 | .125 | .063 | | |
|---|---|---|---|---|---|---|---|---|
| BARNYARDGRASS | 0.0 | 0.0 | 0.0 | 0.0 | 0.0 | 0.0 | | |
| FOXTAIL, GREEN | 3.0 | 3.0 | 1.0 | 0.0 | 0.0 | 0.0 | | |
| NUTSEDGE, PURPLE | 0.0 | 0.0 | 0.0 | 0.0 | 0.0 | 0.0 | | |
| OAT, WILD | 1.0 | 0.0 | 0.0 | 0.0 | 0.0 | 0.0 | | |
| COCKLEBUR | 9.0 | 9.0 | 9.0 | 9.0 | 9.0 | 9.0 | | |
| JIMSONWEED | 9.0 | 9.0 | 9.0 | 9.0 | 9.0 | 9.0 | | |
| LAMBSQUARTERS, C | 9.0 | 9.0 | 9.0 | 9.0 | 8.0 | 7.0 | | |
| MORNINGGLORY SPP | 9.0 | 9.0 | 9.0 | 8.0 | | 0.0 | | |
| MUSTARD, WILD | 9.0 | 9.0 | 9.0 | 9.0 | 9.0 | 9.0 | | |
| PIGWEED, REDROOT | 9.0 | 9.0 | 9.0 | 8.0 | 0.0 | 0.0 | | |
| RAGWEED, COMMON | 9.0 | 9.0 | 9.0 | 0.0 | 0.0 | 0.0 | | |
| VELVETLEAF | 9.0 | 9.0 | 1.0 | 1.0 | 0.0 | 0.0 | | |
| BARLEY, UNSPECIF | 0.0 | 0.0 | 0.0 | 0.0 | 0.0 | 0.0 | | |
| CORN, FIELD | 3.0 | 2.0 | 2.0 | 1.0 | 0.0 | 0.0 | | |
| RICE, UPLAND | 1.0 | 0.0 | 0.0 | 0.0 | 0.0 | 0.0 | | |

TABLE III-continued

Evaluation of the Selective Postemergence Broadleaf Herbicidal Activity of the Compounds of the Invention in the Presence of Graminaceous Crops, Soybeans and Cotton

| Rate (kg/ha): | 2.000 | 1.000 | .500 | .250 | .125 | .063 | .032 | .016 |
|---|---|---|---|---|---|---|---|---|
| SORGHUM, GRAIN | 9.0 | 2.0 | 2.0 | 2.0 | 2.0 | 0.0 | | |
| SOYBEAN | 9.0 | 2.0 | 2.0 | 2.0 | 1.0 | 0.0 | | |
| WHEAT, SPRING, X | 0.0 | 0.0 | 0.0 | 0.0 | 0.0 | 0.0 | | |
| 1,1-Dimethyl-3-[4-(α-methylphenethyloxy)phenyl]urea | | | | | | | | |
| BARNYARDGRASS | 0.0 | 0.0 | 0.0 | 0.0 | 0.0 | 0.0 | | |
| FOXTAIL, GREEN | 2.0 | 0.0 | 0.0 | 0.0 | 0.0 | 0.0 | | |
| NUTSEDGE, PURPLE | 0.0 | 0.0 | 0.0 | 0.0 | 0.0 | 0.0 | | |
| OAT, WILD | 0.0 | 0.0 | 0.0 | 0.0 | 0.0 | 0.0 | | |
| COCKLEBUR | 9.0 | 0.0 | 0.0 | 0.0 | 0.0 | 0.0 | | |
| JIMSONWEED | 9.0 | 9.0 | 0.0 | 0.0 | 0.0 | 0.0 | | |
| LAMBSQUARTERS, C | 9.0 | 9.0 | 8.0 | 6.0 | 6.0 | 0.0 | | |
| MORNINGGLORY SPP | 9.0 | 9.0 | 2.0 | 1.0 | 1.0 | 0.0 | | |
| MUSTARD, WILD | 9.0 | 0.0 | 0.0 | 0.0 | 0.0 | 0.0 | | |
| PIGWEED, REDROOT | 9.0 | 9.0 | 9.0 | 2.0 | 0.0 | 0.0 | | |
| RAGWEED, COMMON | 9.0 | 8.0 | 2.0 | 0.0 | 0.0 | 0.0 | | |
| VELVETLEAF | 4.0 | 0.0 | 0.0 | 0.0 | 0.0 | 0.0 | | |
| BARLEY, UNSPECIF | 1.0 | 0.0 | 0.0 | 0.0 | 0.0 | 0.0 | | |
| CORN, FIELD | 9.0 | 0.0 | 0.0 | 0.0 | 0.0 | 0.0 | | |
| RICE, UPLAND | 1.0 | 0.0 | 0.0 | 0.0 | 0.0 | 0.0 | | |
| SORGHUM, GRAIN | 0.0 | 0.0 | 0.0 | 0.0 | 0.0 | 0.0 | | |
| SOYBEAN | 9.0 | 2.0 | 2.0 | 1.0 | 1.0 | 0.0 | | |
| WHEAT, SPRING, X | 0.0 | 0.0 | 0.0 | 0.0 | 0.0 | 0.0 | | |
| 1-[3-Chloro-4-(phenethyloxy)phenyl]-1-formyl-3-methylurea | | | | | | | | |
| BARNYARDGRASS | 0.0 | 0.0 | 0.0 | 0.0 | 0.0 | 0.0 | | |
| FOXTAIL, GREEN | 0.0 | 0.0 | 0.0 | 0.0 | 0.0 | 0.0 | | |
| NUTSEDGE, PURPLE | 0.0 | 0.0 | 0.0 | 0.0 | 0.0 | 0.0 | | |
| OAT, WILD | 0.0 | 0.0 | 0.0 | 0.0 | 0.0 | 0.0 | | |
| COCKLEBUR | 9.0 | 9.0 | 9.0 | 9.0 | 2.0 | 2.0 | | |
| JIMSONWEED | 9.0 | 0.0 | 0.0 | 0.0 | 0.0 | 0.0 | | |
| LAMBSQUARTERS, C | 9.0 | 9.0 | 9.0 | 3.0 | 0.0 | 0.0 | | |
| MORNINGGLORY SPP | 9.0 | 9.0 | 9.0 | 9.0 | 0.0 | 0.0 | | |
| MUSTARD, WILD | 9.0 | 9.0 | 9.0 | 9.0 | 0.0 | 0.0 | | |
| PIGWEED, REDROOT | 9.0 | 6.0 | 1.0 | | 0.0 | 0.0 | | |
| RAGWEED, COMMON | 9.0 | 9.0 | 2.0 | 0.0 | 0.0 | 0.0 | | |
| VELVETLEAF | 9.0 | 9.0 | 9.0 | 9.0 | 0.0 | 0.0 | | |
| BARLEY, UNSPECIF | 0.0 | 0.0 | 0.0 | 0.0 | 0.0 | 0.0 | | |
| CORN, FIELD | 7.0 | 9.0 | 9.0 | 1.0 | 0.0 | 0.0 | | |
| RICE, UPLAND | 9.0 | 3.0 | 2.0 | 2.0 | 2.0 | 2.0 | | |
| SOYBEAN | 9.0 | 9.0 | 9.0 | 0.0 | 0.0 | 0.0 | | |
| WHEAT, SPRING, X | 4.0 | 0.0 | 0.0 | 0.0 | 0.0 | 0.0 | | |
| 3-[4-(β-ethylphenethyloxy)phenyl]-1,1-dimethylurea | | | | | | | | |
| BARNYARDGRASS | 0.0 | 0.0 | 0.0 | 0.0 | 0.0 | 0.0 | | |
| FOXTAIL, GREEN | 1.0 | 1.0 | 0.0 | 0.0 | 0.0 | 0.0 | | |
| NUTSEDGE, PURPLE | 0.0 | 0.0 | 0.0 | 0.0 | 0.0 | 0.0 | | |
| OAT, WILD | 0.0 | 0.0 | 0.0 | 0.0 | 0.0 | 0.0 | | |
| COCKLEBUR | 9.0 | 0.0 | | | | | | |
| JIMSONWEED | 9.0 | 9.0 | 9.0 | | | | | |
| LAMBSQUARTERS, C | 9.0 | 9.0 | 9.0 | 9.0 | 9.0 | 9.0 | | |
| MORNINGGLORY SPP | 9.0 | 7.0 | | 0.0 | 0.0 | 0.0 | | |
| MUSTARD, WILD | 9.0 | 9.0 | 9.0 | 9.0 | 9.0 | 9.0 | | |
| PIGWEED, REDROOT | 9.0 | 9.0 | 9.0 | 9.0 | 9.0 | 9.0 | | |
| RAGWEED, COMMON | 9.0 | 7.0 | | | 1.0 | | | |
| VELVETLEAF | 1.0 | 1.0 | 1.0 | 1.0 | 0.0 | 0.0 | | |
| BARLEY, UNSPECIF | 0.0 | 0.0 | 0.0 | 0.0 | 0.0 | 0.0 | | |
| CORN, FIELD | 1.0 | 1.0 | 1.0 | | 1.0 | 1.0 | | |
| RICE, UPLAND | 1.0 | 1.0 | 1.0 | 1.0 | 0.0 | 0.0 | | |
| SORGHUM, GRAIN | 1.0 | 1.0 | 1.0 | 1.0 | 1.0 | 1.0 | | |
| SOYBEAN | 9.0 | 9.0 | 9.0 | 9.0 | 1.0 | 0.0 | | |
| WHEAT, SPRING, X | 0.0 | 0.0 | 0.0 | 0.0 | 0.0 | 0.0 | | |
| 3-[3-Chloro-4-(phenethylsulfonyl)phenyl]-1,1-dimethylurea | | | | | | | | |
| BARNYARDGRASS | 0.0 | 0.0 | 0.0 | 0.0 | 0.0 | 0.0 | | |
| FOXTAIL, GREEN | 0.0 | 0.0 | 0.0 | 0.0 | 0.0 | 0.0 | | |
| NUTSEDGE, PURPLE | 0.0 | 0.0 | 0.0 | 0.0 | 0.0 | 0.0 | | |
| OAT, WILD | 0.0 | 0.0 | 0.0 | 0.0 | 0.0 | 0.0 | | |
| COCKLEBUR | 5.5 | 8.5 | 8.5 | 0.5 | 0.0 | 0.0 | | |
| JIMSONWEED | 6.0 | 1.0 | 0.5 | 0.0 | 0.0 | 0.0 | | |
| LAMBSQUARTERS, C | 9.0 | 4.5 | 3.5 | 3.0 | 3.0 | 0.0 | | |
| MORNINGGLORY SPP | 4.5 | 4.5 | 4.5 | 0.0 | 0.0 | 0.0 | | |
| MUSTARD, WILD | 9.0 | 4.5 | 4.5 | 4.5 | 4.0 | 4.0 | | |
| PIGWEED, REDROOT | 4.0 | 2.0 | 1.0 | 0.0 | 0.0 | 0.0 | | |
| RAGWEED, COMMON | 9.0 | 3.5 | 3.0 | 1.5 | 0.0 | 0.0 | | |
| VELVETLEAF | 4.5 | 3.5 | 3.5 | 0.0 | 0.0 | 0.0 | | |
| BARLEY, UNSPECIF | 0.0 | 0.0 | 0.0 | 0.0 | 0.0 | 0.0 | | |
| CORN, FIELD | 0.0 | 0.0 | 0.0 | 0.0 | 0.0 | 0.0 | | |
| RICE, UPLAND | 2.5 | 0.5 | 0.0 | 0.0 | 0.0 | 0.0 | | |
| SORGHUM, GRAIN | 0.0 | 0.0 | 0.0 | 0.0 | 0.0 | 0.0 | | |

TABLE III-continued

Evaluation of the Selective Postemergence Broadleaf Herbicidal Activity of the Compounds of the Invention in the Presence of Graminaceous Crops, Soybeans and Cotton

| Rate (kg/ha): | 2.000 | 1.000 | .500 | .250 | .125 | .063 | .032 | .016 |
|---|---|---|---|---|---|---|---|---|
| (Rates are given in kg/ha) | | | | | | | | |
| SOYBEAN | 3.5 | 4.0 | 1.5 | 0.0 | 0.0 | 0.0 | | |
| WHEAT, SPRING, X | 0.0 | 0.0 | 0.0 | 0.0 | 0.0 | 0.0 | | |
| 1-[3-Chloro-4-(phenethyloxy)phenyl]-1,3,3-trimethylurea | | | | | | | | |
| BARNYARDGRASS | 0.0 | 0.0 | 0.0 | 0.0 | 0.0 | 0.0 | | |
| FOXTAIL, GREEN | 0.0 | 0.0 | 0.0 | 0.0 | 0.0 | 0.0 | | |
| NUTSEDGE, PURPLE | 0.0 | 0.0 | 0.0 | 0.0 | 0.0 | 0.0 | | |
| OAT, WILD | 0.0 | 0.0 | 0.0 | 0.0 | 0.0 | 0.0 | | |
| COCKLEBUR | 0.0 | 0.0 | 0.0 | 0.0 | 0.0 | 0.0 | | |
| JIMSONWEED | 0.0 | 0.0 | 0.0 | 0.0 | 0.0 | 0.0 | | |
| LAMBSQUARTERS, C | 4.0 | 4.0 | 1.0 | 0.0 | 0.0 | 0.0 | | |
| MORNINGGLORY SPP | 0.0 | 0.0 | 0.0 | 0.0 | 0.0 | 0.0 | | |
| MUSTARD, WILD | 2.0 | 2.0 | 0.0 | 0.0 | 0.0 | 0.0 | | |
| PIGWEED, REDROOT | 1.0 | 0.0 | 0.0 | 0.0 | 0.0 | 0.0 | | |
| RAGWEED, COMMON | 0.0 | 0.0 | 0.0 | 0.0 | 0.0 | 0.0 | | |
| VELVETLEAF | 1.0 | 0.0 | 0.0 | 0.0 | 0.0 | 0.0 | | |
| BARLEY, UNSPECIF | 0.0 | 0.0 | 0.0 | 0.0 | 0.0 | 0.0 | | |
| CORN, FIELD | 0.0 | 0.0 | 0.0 | 0.0 | 0.0 | 0.0 | | |
| RICE, UPLAND | 2.0 | 1.0 | 0.0 | 0.0 | 0.0 | 0.0 | | |
| SORGHUM, GRAIN | 0.0 | 0.0 | 0.0 | 0.0 | 0.0 | 0.0 | | |
| SOYBEAN | 1.0 | 0.0 | 0.0 | 0.0 | 0.0 | 0.0 | | |
| WHEAT, SPRING, X | 0.0 | 0.0 | 0.0 | 0.0 | 0.0 | 0.0 | | |
| 3-[3-Chloro-4-(phenethylthio)phenyl]-1,1-dimethylurea | | | | | | | | |
| BARNYARDGRASS | 0.0 | 0.0 | 0.0 | 0.0 | 0.0 | 0.0 | | |
| FOXTAIL, GREEN | 1.0 | 0.0 | 0.0 | 0.0 | 0.0 | 0.0 | | |
| NUTSEDGE, PURPLE | 0.0 | 0.0 | 0.0 | 0.0 | 0.0 | 0.0 | | |
| OAT, WILD | 0.0 | 0.0 | 0.0 | 0.0 | 0.0 | 0.0 | | |
| COCKLEBUR | 9.0 | 9.0 | 7.0 | 0.0 | 0.0 | 0.0 | | |
| JIMSONWEED | 9.0 | 0.0 | 0.0 | 0.0 | 0.0 | 0.0 | | |
| LAMBSQUARTERS, C | 9.0 | 2.0 | 2.0 | | 0.0 | 0.0 | | |
| MORNINGGLORY SPP | 9.0 | 7.0 | 4.0 | 0.0 | 0.0 | 0.0 | | |
| MUSTARD, WILD | 9.0 | 3.0 | 3.0 | 2.0 | | | | |
| PIGWEED, REDROOT | 9.0 | 9.0 | 9.0 | 4.0 | 0.0 | 0.0 | | |
| RAGWEED, COMMON | 3.0 | 0.0 | 0.0 | 0.0 | 0.0 | 0.0 | | |
| VELVETLEAF | 0.0 | 0.0 | 0.0 | 0.0 | 0.0 | 0.0 | | |
| BARLEY, UNSPECIF | 0.0 | 0.0 | 0.0 | 0.0 | 0.0 | 0.0 | | |
| CORN, FIELD | 0.0 | 0.0 | 0.0 | 0.0 | 0.0 | 0.0 | | |
| RICE, UPLAND | 0.0 | 0.0 | 0.0 | 0.0 | 0.0 | 0.0 | | |
| SORGHUM, GRAIN | 0.0 | 0.0 | 0.0 | 0.0 | 0.0 | 0.0 | | |
| SOYBEAN | 9.0 | 2.0 | 4.0 | 0.0 | 0.0 | 0.0 | | |
| WHEAT, SPRING, X | 0.0 | 0.0 | 0.0 | 0.0 | 0.0 | 0.0 | | |
| 1-[3-Chloro-4-(α-methylphenethyloxy)phenyl]-3-methylurea | | | | | | | | |
| BARNYARDGRASS | 0.0 | 0.0 | 0.0 | 0.0 | 0.0 | 0.0 | | |
| FOXTAIL, GREEN | 3.0 | | 0.0 | 0.0 | 0.0 | 0.0 | | |
| NUTSEDGE, PURPLE | 0.0 | 0.0 | 0.0 | 0.0 | 0.0 | 0.0 | | |
| OAT, WILD | 0.0 | 0.0 | 0.0 | 0.0 | 0.0 | 0.0 | | |
| COCKLEBUR | 3.0 | 0.0 | 0.0 | | 0.0 | 0.0 | | |
| JIMSONWEED | 9.0 | 9.0 | 9.0 | 9.0 | 9.0 | 0.0 | | |
| LAMBSQUARTERS, C | 9.0 | 9.0 | 9.0 | 9.0 | 9.0 | 4.0 | | |
| MORNINGGLORY SPP | 9.0 | 9.0 | 9.0 | 8.0 | 0.0 | 0.0 | | |
| MUSTARD, WILD | 9.0 | 9.0 | 9.0 | 9.0 | 9.0 | 6.0 | | |
| PIGWEED, REDROOT | 9.0 | 9.0 | 9.0 | 6.0 | 6.0 | 0.0 | | |
| RAGWEED, COMMON | 9.0 | 9.0 | 9.0 | 7.0 | 7.0 | 5.0 | | |
| VELVETLEAF | 7.0 | 7.0 | 7.0 | 4.0 | 0.0 | 0.0 | | |
| BARLEY, UNSPECIF | 0.0 | 0.0 | 0.0 | 0.0 | 0.0 | 0.0 | | |
| CORN, FIELD | 6.0 | 2.0 | | 4.0 | 0.0 | 0.0 | | |
| RICE, UPLAND | 3.0 | 3.0 | 2.0 | 0.0 | 0.0 | 0.0 | | |
| SORGHUM, GRAIN | 1.0 | 0.0 | 0.0 | 0.0 | 0.0 | 0.0 | | |
| SOYBEAN | 9.0 | 9.0 | 4.0 | 9.0 | 2.0 | 2.0 | | |
| WHEAT, SPRING, X | 1.0 | 0.0 | 0.0 | 0.0 | 0.0 | 0.0 | | |
| 3-[4-(α-ethylphenethyloxy)phenyl]-1,1-dimethylurea | | | | | | | | |
| BARNYARDGRASS | 0.0 | 0.0 | 0.0 | 0.0 | 0.0 | 0.0 | | |
| FOXTAIL, GREEN | 0.0 | 0.0 | 0.0 | 0.0 | 0.0 | 0.0 | | |
| NUTSEDGE, PURPLE | 0.0 | 0.0 | 0.0 | 0.0 | 0.0 | 0.0 | | |
| OAT, WILD | 0.0 | 0.0 | 0.0 | 0.0 | 0.0 | 0.0 | | |
| COCKLEBUR | 0.0 | 0.0 | 0.0 | 0.0 | 0.0 | 0.0 | | |
| JIMSONWEED | | | 0.0 | 0.0 | 0.0 | 0.0 | | |
| LAMBSQUARTERS, C | 9.0 | 7.0 | 2.0 | 1.0 | 1.0 | 0.0 | | |
| MORNINGGLORY SPP | 4.0 | 1.0 | 1.0 | 0.0 | 0.0 | 0.0 | | |
| MUSTARD, WILD | 7.0 | 0.0 | 0.0 | 0.0 | 0.0 | 0.0 | | |
| PIGWEED, REDROOT | 6.0 | 0.0 | 0.0 | 0.0 | 0.0 | 0.0 | | |
| RAGWEED, COMMON | 0.0 | 0.0 | 0.0 | 0.0 | 0.0 | 0.0 | | |
| VELVETLEAF | 4.0 | 1.0 | 0.0 | 0.0 | 0.0 | 0.0 | | |
| BARLEY, UNSPECIF | 0.0 | 0.0 | 0.0 | 0.0 | 0.0 | 0.0 | | |
| CORN, FIELD | 0.0 | 0.0 | 0.0 | 0.0 | 0.0 | 0.0 | | |
| RICE, UPLAND | 0.0 | 0.0 | 0.0 | 0.0 | 0.0 | 0.0 | | |
| SORGHUM, GRAIN | 0.0 | 0.0 | 0.0 | 0.0 | 0.0 | 0.0 | | |

TABLE III-continued

Evaluation of the Selective Postemergence Broadleaf Herbicidal Activity of the Compounds of the Invention in the Presence of Graminaceous Crops, Soybeans and Cotton

| Rate (kg/ha): | 2.000 | 1.000 | .500 | .250 | .125 | .063 | .032 | .016 |
|---|---|---|---|---|---|---|---|---|
| SOYBEAN | 0.0 | 0.0 | 0.0 | 0.0 | 0.0 | 0.0 | | |
| WHEAT, SPRING, X | 0.0 | 0.0 | 0.0 | 0.0 | 0.0 | 0.0 | | |
| 1-[3-Chloro-4-($\beta$-methylphenethyloxy)phenyl]-3-methylurea | | | | | | | | |
| BARNYARDGRASS | 0.0 | 0.0 | 0.0 | 0.0 | 0.0 | 0.0 | | |
| FOXTAIL, GREEN | 2.0 | 2.0 | 2.0 | 0.0 | 0.0 | 0.0 | | |
| NUTSEDGE, PURPLE | 0.0 | 0.0 | 0.0 | 0.0 | 0.0 | 0.0 | | |
| OAT, WILD | 0.0 | 0.0 | 0.0 | 0.0 | 0.0 | 0.0 | | |
| COCKLEBUR | 9.0 | 9.0 | | 1.0 | 0.0 | 0.0 | | |
| JIMSONWEED | 9.0 | 9.0 | 9.0 | | | | | |
| LAMBSQUARTERS, C | 9.0 | 9.0 | 9.0 | 9.0 | 9.0 | 9.0 | | |
| MORNINGGLORY SPP | 9.0 | 9.0 | 9.0 | 9.0 | 2.0 | 3.0 | | |
| MUSTARD, WILD | 9.0 | 9.0 | 9.0 | 9.0 | 9.0 | 3.0 | | |
| PIGWEED, REDROOT | 9.0 | 9.0 | 9.0 | 9.0 | 9.0 | 9.0 | | |
| RAGWEED, COMMON | 9.0 | 9.0 | 8.0 | 9.0 | 3.0 | 3.0 | | |
| VELVETLEAF | 8.0 | 9.0 | 9.0 | 2.0 | 2.0 | 2.0 | | |
| BARLEY, UNSPECIF | 0.0 | 0.0 | 0.0 | 0.0 | 0.0 | 0.0 | | |
| CORN, FIELD | 9.0 | 9.0 | 0.0 | 0.0 | 0.0 | 0.0 | | |
| RICE, UPLAND | 4.0 | 3.0 | 2.0 | 0.0 | 3.0 | 0.0 | | |
| SORGHUM, GRAIN | 2.0 | 1.0 | 1.0 | 1.0 | 0.0 | 0.0 | | |
| SOYBEAN | 8.0 | 9.0 | 6.0 | 0.0 | 0.0 | 0.0 | | |
| WHEAT, SPRING, X | 0.0 | 0.0 | 0.0 | 0.0 | 0.0 | 0.0 | | |
| 1,1-Dimethyl-3-[4-(3-phenylpropoxy)-3-tolyl]urea | | | | | | | | |
| BARNYARDGRASS | 0.0 | 0.0 | 0.0 | 0.0 | 0.0 | 0.0 | | |
| FOXTAIL, GREEN | 8.0 | 7.0 | 7.0 | 3.0 | 3.0 | 0.0 | | |
| NUTSEDGE, PURPLE | 0.0 | 0.0 | 0.0 | 0.0 | 0.0 | 0.0 | | |
| OAT, WILD | 0.0 | 0.0 | 0.0 | 0.0 | 0.0 | 0.0 | | |
| COCKLEBUR | 0.0 | 7.0 | 9.0 | 1.0 | 0.0 | 0.0 | | |
| JIMSONWEED | 8.0 | 9.0 | 9.0 | 9.0 | 0.0 | 0.0 | | |
| LAMBSQUARTERS, C | 9.0 | 9.0 | 9.0 | 9.0 | 8.0 | 6.0 | | |
| MORNINGGLORY SPP | 9.0 | 9.0 | 9.0 | 9.0 | 9.0 | 9.0 | | |
| MUSTARD, WILD | 9.0 | 9.0 | 9.0 | 9.0 | 9.0 | 9.0 | | |
| PIGWEED, REDROOT | 9.0 | 9.0 | 9.0 | 6.0 | 3.0 | 0.0 | | |
| RAGWEED, COMMON | 9.0 | 7.0 | 2.0 | 0.0 | 0.0 | 0.0 | | |
| VELVETLEAF | 9.0 | 9.0 | 9.0 | 2.0 | | 4.0 | | |
| BARLEY, UNSPECIF | 0.0 | 0.0 | 0.0 | 0.0 | 0.0 | 0.0 | | |
| CORN, FIELD | 1.0 | 2.0 | 1.0 | 1.0 | 0.0 | 0.0 | | |
| RICE, UPLAND | 4.0 | 2.0 | 2.0 | 1.0 | 1.0 | 0.0 | | |
| SORGHUM, GRAIN | 2.0 | 2.0 | 1.0 | 1.0 | 1.0 | 1.0 | | |
| SOYBEAN | 9.0 | 9.0 | 9.0 | 5.0 | | 5.0 | | |
| WHEAT, SPRING, X | 0.0 | 0.0 | 0.0 | 0.0 | 0.0 | 0.0 | | |
| 3'-Chloro-2,5-dimethyl-4'-phenethyloxy-1-pyrrolidinecarboxanilide | | | | | | | | |
| BARNYARDGRASS | 0.0 | 0.0 | 0.0 | 0.0 | 0.0 | 0.0 | | |
| FOXTAIL, GREEN | 1.0 | 0.0 | 0.0 | 0.0 | 0.0 | 0.0 | | |
| NUTSEDGE, PURPLE | 0.0 | 0.0 | 0.0 | 0.0 | 0.0 | 0.0 | | |
| OAT, WILD | 0.0 | 0.0 | 0.0 | 0.0 | 0.0 | 0.0 | | |
| COCKLEBUR | 9.0 | 9.0 | 0.0 | 0.0 | 0.0 | 0.0 | | |
| JIMSONWEED | | 0.0 | 0.0 | 0.0 | 0.0 | 0.0 | | |
| LAMBSQUARTERS, C | 9.0 | 7.0 | 2.0 | 0.0 | 0.0 | 0.0 | | |
| MORNINGGLORY SPP | 0.0 | | | 0.0 | 0.0 | 0.0 | | |
| MUSTARD, WILD | 9.0 | 9.0 | 9.0 | 7.0 | | 7.0 | | |
| PIGWEED, REDROOT | 9.0 | 9.0 | 9.0 | 0.0 | 0.0 | 0.0 | | |
| RAGWEED, COMMON | 0.0 | 0.0 | 0.0 | 0.0 | 0.0 | 0.0 | | |
| VELVETLEAF | 0.0 | 0.0 | 0.0 | 0.0 | 0.0 | 0.0 | | |
| BARLEY, UNSPECIF | 0.0 | 0.0 | 0.0 | 0.0 | 0.0 | 0.0 | | |
| CORN, FIELD | 0.0 | 0.0 | 0.0 | 0.0 | 0.0 | 0.0 | | |
| RICE, UPLAND | 0.0 | 0.0 | 0.0 | 0.0 | 0.0 | 0.0 | | |
| SORGHUM, GRAIN | 0.0 | 0.0 | 0.0 | 0.0 | 0.0 | 0.0 | | |
| SOYBEAN | 0.0 | 0.0 | 0.0 | 0.0 | 0.0 | 0.0 | | |
| WHEAT, SPRING, X | 0.0 | 0.0 | 0.0 | 0.0 | 0.0 | 0.0 | | |
| 1-[3-Chloro-4-(phenethyloxy)phenyl]-3-(2-propynyl)urea | | | | | | | | |
| BARNYARDGRASS | 0.0 | 0.0 | 0.0 | 0.0 | 0.0 | 0.0 | | |
| FOXTAIL, GREEN | 0.0 | 0.0 | 0.0 | 0.0 | 0.0 | 0.0 | | |
| NUTSEDGE, PURPLE | 0.0 | 0.0 | 0.0 | 0.0 | 0.0 | 0.0 | | |
| OAT, WILD | 0.0 | 0.0 | 0.0 | 0.0 | 0.0 | 0.0 | | |
| COCKLEBUR | 2.0 | 0.0 | 0.0 | 0.0 | 0.0 | 0.0 | | |
| JIMSONWEED | | | | | | 0.0 | | |
| LAMBSQUARTERS, C | 9.0 | 9.0 | 9.0 | 1.0 | 0.0 | | | |
| MORNINGGLORY SPP | 0.0 | 0.0 | 0.0 | 0.0 | 0.0 | | | |
| MUSTARD, WILD | 6.0 | 6.0 | 6.0 | 6.0 | 5.0 | 0.0 | | |
| PIGWEED, REDROOT | 4.0 | 4.0 | 3.0 | | 3.0 | 0.0 | | |
| RAGWEED, COMMON | 0.0 | 0.0 | 0.0 | 0.0 | 0.0 | 0.0 | | |
| VELVETLEAF | 0.0 | 0.0 | 0.0 | 0.0 | 0.0 | 0.0 | | |
| BARLEY, UNSPECIF | 0.0 | 0.0 | 0.0 | 0.0 | 0.0 | 0.0 | | |
| CORN, FIELD | 0.0 | 0.0 | 0.0 | 0.0 | 0.0 | 0.0 | | |
| RICE, UPLAND | 0.0 | 0.0 | 0.0 | 0.0 | 0.0 | 0.0 | | |
| SORGHUM, GRAIN | 0.0 | 0.0 | 0.0 | 0.0 | 0.0 | 0.0 | | |

TABLE III-continued

Evaluation of the Selective Postemergence Broadleaf Herbicidal Activity of the Compounds of the Invention in the Presence of Graminaceous Crops, Soybeans and Cotton (Rates are given in kg/ha)

| Rate (kg/ha): | 2.000 | 1.000 | .500 | .250 | .125 | .063 | .032 | .016 |
|---|---|---|---|---|---|---|---|---|
| SOYBEAN | 0.0 | 0.0 | 0.0 | 0.0 | 0.0 | 0.0 | | |
| WHEAT, SPRING, X | 0.0 | 0.0 | 0.0 | 0.0 | 0.0 | 0.0 | | |
| 3-[3-Methoxy-4-(phenethyloxy)phenyl]-1,1-dimethylurea | | | | | | | | |
| BARNYARDGRASS | 2.0 | 1.0 | 0.0 | 0.0 | 0.0 | 0.0 | | |
| FOXTAIL, GREEN | 1.0 | 1.0 | 0.0 | 0.0 | 0.0 | 0.0 | | |
| NUTSEDGE, PURPLE | 0.0 | 0.0 | 0.0 | 0.0 | 0.0 | 0.0 | | |
| OAT, WILD | 0.0 | 0.0 | 0.0 | 0.0 | 0.0 | 0.0 | | |
| COCKLEBUR | | 9.0 | 9.0 | 9.0 | 7.0 | 0.0 | | |
| JIMSONWEED | 9.0 | 9.0 | 9.0 | 9.0 | 9.0 | 0.0 | | |
| LAMBSQUARTERS, C | 9.0 | 8.0 | 6.0 | 3.0 | 0.0 | 0.0 | | |
| MORNINGGLORY, SPP | 9.0 | 8.0 | 4.0 | 0.0 | 0.0 | 0.0 | | |
| MUSTARD, WILD | 9.0 | 9.0 | 9.0 | 9.0 | 2.0 | 0.0 | | |
| PIGWEED, REDROOT | 9.0 | 9.0 | 9.0 | 9.0 | 8.0 | | | |
| RAGWEED, COMMON | 9.0 | 7.0 | 7.0 | 3.0 | 0.0 | 0.0 | | |
| VELVETLEAF | 9.0 | 9.0 | 0.0 | 0.0 | 0.0 | 0.0 | | |
| BARLEY, UNSPECIF | 0.0 | 0.0 | 0.0 | 0.0 | 0.0 | 0.0 | | |
| CORN, FIELD | 1.0 | 1.0 | 0.0 | 0.0 | 0.0 | 0.0 | | |
| RICE, UPLAND | 0.0 | 0.0 | 0.0 | 0.0 | 0.0 | 0.0 | | |
| SORGHUM, GRAIN | 0.0 | 0.0 | 3.0 | 0.0 | 0.0 | 0.0 | | |
| SOYBEAN | 8.0 | 3.0 | 0.0 | 2.0 | 0.0 | 0.0 | | |
| WHEAT, SPRING, X | 0.0 | 0.0 | 0.0 | 0.0 | 0.0 | 0.0 | | |
| 3-{3-Chloro-4-[3-(2-phenyl-1,3-dioxolan-2-yl)propoxy]phenyl}-1,1-dimethylurea | | | | | | | | |
| BARNYARDGRASS | 0.0 | 0.0 | 0.0 | 0.0 | 0.0 | 0.0 | | |
| FOXTAIL, GREEN | 0.0 | 0.0 | 0.0 | 0.0 | 0.0 | 0.0 | | |
| NUTSEDGE, PURPLE | 0.0 | 0.0 | 0.0 | 0.0 | 0.0 | 0.0 | | |
| OAT, WILD | 0.0 | 0.0 | 0.0 | 0.0 | 0.0 | 0.0 | | |
| COCKLEBUR | 0.0 | 0.0 | 0.0 | 0.0 | 0.0 | 0.0 | | |
| JIMSONWEED | 9.0 | 9.0 | 9.0 | 9.0 | 9.0 | 9.0 | | |
| LAMBSQUARTERS, C | 9.0 | 9.0 | 6.0 | 9.0 | 3.0 | 0.0 | | |
| MORNINGGLORY SPP | 4.0 | 2.0 | 0.0 | 0.0 | 0.0 | 0.0 | | |
| MUSTARD, WILD | 9.0 | 9.0 | 9.0 | 9.0 | 9.0 | 3.0 | | |
| PIGWEED, REDROOT | 9.0 | 9.0 | 9.0 | 9.0 | 3.0 | 9.0 | | |
| RAGWEED, COMMON | 6.0 | 4.0 | 0.0 | 0.0 | 0.0 | 0.0 | | |
| VELVETLEAF | 9.0 | 9.0 | 9.0 | 9.0 | 9.0 | 0.0 | | |
| BARLEY, UNSPECIF | 0.0 | 0.0 | 0.0 | 0.0 | 0.0 | 0.0 | | |
| CORN, FIELD | 9.0 | 0.0 | 0.0 | 0.0 | 0.0 | 0.0 | | |
| RICE, UPLAND | 2.0 | 1.0 | 1.0 | 1.0 | 0.0 | 0.0 | | |
| SORGHUM, GRAIN | 0.0 | 0.0 | 0.0 | 0.0 | 0.0 | 0.0 | | |
| SOYBEAN | 9.0 | 9.0 | 9.0 | 9.0 | 2.0 | 0.0 | | |
| WHEAT, SPRING, X | 0.0 | 0.0 | 0.0 | 0.0 | 0.0 | 0.0 | | |

EXAMPLE 26

Preemergence Herbicidal Activity

The preemergence herbicidal activity of the compounds of the present invention is exemplified by the following tests in which the seeds or propagating organs of a varity of monocotyledonous and dicotyledonous plants are separately mixed with potting soil and planted on top of approximately 2.5 cm of soil in separate cups. After planting, the cups are sprayed with selected aqueous/acetone solution containing test compound in sufficient quantity to provide the equivalence of about 0.07 kg to 2.0 kg per hectare of test compound per cup. The treated cups are then placed on greenhouse benches, watered and cared for in accordance with conventional greenhouse procedures. Three to five weeks after treatment, the tests are terminated and each cup is examined and rated according to the rating system set forth in Example 25. The data obtained are reported in Table IV below.

The rates displayed in Table IV below are the averages of two or more replicates.

TABLE IV

Evaluation of the Selective Preemergence Broadleaf Herbicidal Activity of the Compounds of the Invention in the Presence of Graminaceous Crops, Soybeans and Cotton (Rates are given in kg/ha)

| Rate (kg/ha): | 2.000 | 1.000 | .500 | .250 | .125 | .063 | .032 |
|---|---|---|---|---|---|---|---|
| 3-[3-Chloro-4-(5-phenylpentyloxy)phenyl]-1,1-dimethylurea | | | | | | | |
| Barnyardgrass | 0.0 | 0.0 | 0.0 | 0.0 | 0.0 | 0.0 | |
| Foxtail, Green | 0.0 | 0.0 | 0.0 | 0.0 | 0.0 | 0.0 | |
| Nutsedge, Purple | 0.0 | 0.0 | 0.0 | 0.0 | 0.0 | 0.0 | |
| Oat, Wild | 0.0 | 0.0 | 0.0 | 0.0 | 0.0 | 0.0 | |
| Cocklebur | 0.0 | 0.0 | 0.0 | 0.0 | 0.0 | 0.0 | |
| Jimsonweed | 0.0 | 0.0 | 0.0 | 0.0 | 0.0 | 0.0 | |
| Lambsquarters, C | 9.0 | 9.0 | 9.0 | 9.0 | 7.0 | 7.0 | |
| Morningglory Spp | 0.0 | 0.0 | 0.0 | 0.0 | 0.0 | 0.0 | |
| Mustard, Wild | 9.0 | 9.0 | 3.0 | 0.0 | 0.0 | 0.0 | |
| Pigweed, Redroot | 9.0 | 9.0 | 8.0 | 0.0 | 0.0 | 0.0 | |
| Ragweed, Common | 0.0 | 0.0 | 0.0 | 0.0 | 0.0 | 0.0 | |
| Velvetleaf | 0.0 | 0.0 | 0.0 | 0.0 | 0.0 | 0.0 | |
| Barley, Unspecif | 0.0 | 0.0 | 0.0 | 0.0 | 0.0 | 0.0 | |
| Corn, Field | 0.0 | 0.0 | 0.0 | 0.0 | 0.0 | 0.0 | |
| Rice, Upland | 0.0 | 0.0 | 0.0 | 0.0 | 0.0 | 0.0 | |
| Sorghum, Grain | 0.0 | 0.0 | 0.0 | 0.0 | 0.0 | 0.0 | |
| Soybean | 0.0 | 0.0 | 0.0 | 0.0 | 0.0 | 0.0 | |
| Wheat, Spring, X | 0.0 | 0.0 | 0.0 | 0.0 | 0.0 | 0.0 | |
| 3-[3-Chloro-4-(phenethyloxy)phenyl]-1,1-dimethylurea | | | | | | | |
| Barnyardgrass | 0.7 | 0.3 | 0.1 | 0.0 | 0.0 | 0.0 | |
| Blackgrass | 0.0 | 0.0 | 0.0 | | | | |
| Canarygrass, Lit | 0.0 | 0.0 | 0.0 | | | | |
| Crabgrass, (Hair | 3.0 | 1.0 | 0.0 | 0.0 | 0.0 | 0.0 | |

TABLE IV-continued
Evaluation of the Selective Preemergence Broadleaf Herbicidal Activity of the Compounds of the Invention in the Presence of Graminaceous Crops, Soybeans and Cotton
(Rates are given in kg/ha)

| Rate (kg/ha): | 2.000 | 1.000 | .500 | .250 | .125 | .063 | .032 |
|---|---|---|---|---|---|---|---|
| Foxtail, Green | 2.1 | 0.7 | 0.1 | 0.0 | 0.0 | 0.0 | |
| Johnsongrass (Fr | 0.0 | 0.0 | 0.0 | | | | |
| Nutsedge, Purple | 0.0 | 0.0 | 0.0 | 0.0 | 0.0 | 0.0 | |
| Nutsedge, Yellow | 0.0 | 0.0 | 0.0 | | | | |
| Oat, Wild | 0.2 | 0.0 | 0.0 | 0.0 | 0.0 | 0.0 | |
| Quackgrass | 0.0 | 0.0 | 0.0 | | | | |
| Bindweed, Field | 0.0 | 0.0 | 0.0 | | | | |
| Buckwheat, Tarta | 2.0 | 0.0 | 0.0 | | | | |
| Cocklebur | 0.2 | 0.0 | 0.0 | 0.0 | 0.0 | 0.0 | |
| Jimsonweed | 6.1 | 4.6 | 3.6 | 2.1 | 0.9 | 0.9 | |
| Lambsquarters, C | 8.8 | 9.0 | 8.8 | 7.8 | 7.0 | 4.6 | |
| Mayweed | 7.0 | 7.0 | 6.0 | | | | |
| Morningglory Spp | 4.8 | 2.4 | 0.7 | 0.3 | 0.0 | 0.0 | |
| Mustard, Wild | 9.0 | 9.0 | 9.0 | 8.2 | 3.5 | 1.5 | |
| Pigweed, Redroot | 9.0 | 9.0 | 8.9 | 8.5 | 5.9 | 2.7 | |
| Ragweed, Common | 5.1 | 1.4 | 0.3 | 0.1 | 0.0 | 0.0 | |
| Thistle, Canada | 0.0 | 0.0 | 0.0 | | | | |
| Velvetleaf | 4.5 | 0.5 | 0.0 | 0.0 | 0.0 | 0.0 | |
| Barley, Unspecif | 0.0 | 0.0 | 0.0 | | | | |
| Barley, Larker | 0.0 | 0.0 | 0.0 | | | | |
| Corn, Field | 0.1 | 0.1 | 0.0 | 0.0 | 0.0 | 0.0 | |
| Cotton | 0.0 | 0.0 | 0.0 | 0.0 | 0.0 | 0.0 | |
| Rice, Upland | 0.2 | 0.2 | 0.1 | 0.0 | 0.0 | 0.0 | |
| Rice, Saturn | 0.0 | 0.0 | 0.0 | | | | |
| Sorghum, Grain | 0.0 | 0.0 | 0.0 | 0.0 | 0.0 | 0.0 | |
| Soybean | 0.1 | 0.0 | 0.4 | 0.0 | 0.0 | 0.0 | |
| Wheat, Spring, X | 0.1 | 0.0 | 0.0 | 0.0 | 0.0 | 0.0 | |
| Wheat, Spring, E | 0.0 | 0.0 | 0.0 | | | | |
| 3-[3-Chloro-4-(3-phenylpropoxy)phenyl]-1,1-dimethylurea | | | | | | | |
| Barnyardgrass | 0.0 | 0.0 | 0.0 | 0.0 | 0.0 | 0.0 | |
| Blackgrass | 0.0 | 0.0 | 0.0 | | | | |
| Canarygrass, Lit | 0.0 | 0.0 | 0.0 | | | | |
| Crabgrass, (Hair | | 1.0 | 0.0 | 0.0 | 0.0 | 0.0 | |
| Foxtail, Green | 0.0 | 1.0 | 0.0 | 0.0 | 0.0 | 0.0 | |
| Johnsongrass (Fr | 0.0 | 0.0 | 0.0 | | | | |
| Nutsedge, Purple | 0.0 | 0.0 | 0.0 | 0.0 | 0.0 | 0.0 | |
| Nutsedge, Yellow | 0.0 | 0.0 | 0.0 | | | | |
| Oat, Wild | 0.0 | 0.0 | 0.0 | 0.0 | 0.0 | 0.0 | |
| Quackgrass | 0.0 | 0.0 | 0.0 | | | | |
| Bindweed, Field | 0.0 | 0.0 | 0.0 | | | | |
| Buckwheat, Tarta | 0.0 | 0.0 | 0.0 | | | | |
| Cocklebur | 0.0 | 0.3 | 0.0 | 0.0 | 0.0 | 0.0 | |
| Jimsonweed | 4.0 | 1.0 | 0.3 | 0.0 | 0.0 | 0.0 | |
| Lambsquarters, C | 9.0 | 8.0 | 8.0 | 6.5 | 3.5 | 3.5 | |
| Mayweed | 9.0 | 8.0 | 2.0 | | | | |
| Morningglory Spp | 4.0 | 0.5 | 0.0 | 0.0 | 0.0 | 0.0 | |
| Mustard, Wild | 9.0 | 9.0 | 7.5 | 4.5 | 3.0 | 2.0 | |
| Pigweed, Redroot | 9.0 | 9.0 | 8.0 | 5.0 | 0.5 | 0.0 | |
| Ragweed, Common | 0.0 | 0.0 | 0.0 | 0.0 | 0.0 | 0.0 | |
| Thistle, Canada | 1.0 | 0.0 | 0.0 | | | | |
| Velvetleaf | 0.0 | 0.0 | 0.0 | 0.0 | 0.0 | 0.0 | |
| Barley, Unspecif | 0.0 | 0.0 | 0.0 | 0.0 | 0.0 | 0.0 | |
| Barley, Larker | 0.0 | 0.0 | 0.0 | | | | |
| Corn, Field | 0.0 | 0.0 | 0.0 | 0.0 | 0.0 | 0.0 | |
| Cotton | | 0.0 | 0.0 | 0.0 | 0.0 | 0.0 | |
| Rice, Upland | 0.0 | 0.0 | 0.0 | 0.0 | 0.0 | 0.0 | |
| Rice, Saturn | 0.0 | 0.0 | 0.0 | | | | |
| Sorghum, Grain | 0.0 | 0.0 | 0.0 | 0.0 | 0.0 | 0.0 | |
| Soybean | 0.0 | 0.0 | 0.0 | 0.0 | 0.0 | 0.0 | |
| Wheat, Spring, X | 0.0 | 0.0 | 0.0 | 0.0 | 0.0 | 0.0 | |
| Wheat, Spring, E | 0.0 | 0.0 | 0.0 | | | | |
| 1,1-Dimethyl-3-[4-(phenethyloxy)phenyl]urea | | | | | | | |
| Barnyardgrass | | 4.0 | 1.0 | 0.0 | 0.0 | 0.0 | |
| Blackgrass | 0.0 | 0.0 | 0.0 | | | | |
| Canarygrass, Lit | 0.0 | 0.0 | 0.0 | | | | |
| Crabgrass (Hair | | 2.0 | 0.0 | 0.0 | 0.0 | 0.0 | |
| Foxtail, Green | | 3.0 | 0.0 | 0.0 | 0.0 | 0.0 | |
| Johnsongrass (Fr | 0.0 | 0.0 | 0.0 | | | | |
| Nutsedge, Purple | 0.0 | 0.0 | 0.0 | | | | |
| Nutsedge, Yellow | 0.0 | 0.0 | 0.0 | | | | |
| Oat, Wild | 0.0 | 0.0 | 0.0 | 0.0 | 0.0 | 0.0 | |
| Quackgrass | 0.0 | 0.0 | 0.0 | | | | |
| Bindweed, Field | 1.0 | 0.0 | 0.0 | | | | |
| Buckwheat, Tarta | 9.0 | 3.0 | 0.0 | | | | |
| Cocklebur | 0.0 | 0.0 | 0.0 | 0.0 | 0.0 | 0.0 | |
| Jimsonweed | 0.0 | 4.5 | 4.5 | 2.0 | 0.0 | 0.0 | |
| Lambsquarters, C | | 9.0 | 9.0 | 4.0 | 4.0 | 0.0 | |
| Mayweed | 3.0 | 2.0 | 1.0 | | | | |
| Morningglory Spp | | 6.0 | 0.0 | 0.0 | 0.0 | 0.0 | |
| Mustard, Wild | | 9.0 | 9.0 | 3.0 | 2.0 | 0.0 | |
| Pigweed, Redroot | | 9.0 | 9.0 | 9.0 | 8.0 | 0.0 | |
| Ragweed, Common | | 9.0 | 6.0 | 0.0 | 0.0 | 0.0 | |
| Thistle, Canada | 1.0 | 0.0 | 0.0 | | | | |
| Velvetleaf | | 0.0 | 0.0 | 0.0 | 0.0 | 0.0 | |
| Barley, Unspecif | | 0.0 | 0.0 | 0.0 | 0.0 | 0.0 | |
| Barley, Larker | 0.0 | 0.0 | 0.0 | | | | |
| Corn, Field | 0.0 | 0.0 | 0.0 | 0.0 | 0.0 | 0.0 | |
| Cotton | | 0.0 | 0.0 | 0.0 | 0.0 | 0.0 | |
| Rice, Upland | | 0.0 | 0.0 | 0.0 | 0.0 | 0.0 | |
| Rice, Saturn | 0.0 | 0.0 | 0.0 | | | | |
| Soybean | 0.0 | 0.0 | 0.0 | 0.0 | 0.0 | 0.0 | |
| Wheat, Spring, X | | 0.0 | 0.0 | 0.0 | 0.0 | 0.0 | |
| Wheat, Spring, E | 0.0 | 0.0 | 0.0 | | | | |
| 1,1-Dimethyl-3-[4-(3-phenylpropoxy)phenyl]urea | | | | | | | |
| Barnyardgrass | | 1.0 | 1.0 | 0.0 | 0.0 | 0.0 | |
| Crabgrass, (Hair | | 1.0 | 0.0 | 0.0 | 0.0 | 0.0 | |
| Foxtail, Green | | 1.0 | 0.0 | 0.0 | 0.0 | 0.0 | |
| Oat, Wild | | 0.0 | 0.0 | 0.0 | 0.0 | 0.0 | |
| Cocklebur | | 0.0 | 0.0 | 0.0 | 0.0 | 0.0 | |
| Jimsonweed | | 4.0 | 0.0 | 0.0 | 0.0 | 0.0 | |
| Lambsquarters, C | | 9.0 | 7.0 | 9.0 | 2.0 | 0.0 | |
| Morningglory Spp | | 0.0 | 0.0 | 0.0 | 0.0 | 0.0 | |
| Mustard, Wild | | 9.0 | 9.0 | 6.0 | 0.0 | 0.0 | |
| Pigweed, Redroot | | 9.0 | 9.0 | 9.0 | 1.0 | 0.0 | |
| Ragweed, Cotton | | 1.0 | 0.0 | 0.0 | 0.0 | 0.0 | |
| Velvetleaf | | 0.0 | 0.0 | 0.0 | 0.0 | 0.0 | |
| Barley, Unspecif | | 0.0 | 0.0 | 0.0 | 0.0 | 0.0 | |
| Corn, Field | | 0.0 | 0.0 | 0.0 | 0.0 | 0.0 | |
| Cotton | | 0.0 | 0.0 | 0.0 | 0.0 | 0.0 | |
| Rice, Upland | | 0.0 | 0.0 | 0.0 | 0.0 | 0.0 | |
| Soybean | | 0.0 | 0.0 | 0.0 | 0.0 | 0.0 | |
| Wheat, Spring, X | | 0.0 | 0.0 | 0.0 | 0.0 | 0.0 | |
| 3-[3-Chloro-4-(4-phenylbutoxy)phenyl]-1,1-dimethylurea | | | | | | | |
| Barnyardgrass | | 0.0 | 0.0 | 0.0 | 0.0 | 0.0 | |
| Crabgrass, (Hair | | 0.0 | 0.0 | 0.0 | 0.0 | 0.0 | |
| Foxtail, Green | | 0.0 | 0.0 | 0.0 | 0.0 | 0.0 | |
| Oat, Wild | | 0.0 | 0.0 | 0.0 | 0.0 | 0.0 | |
| Cocklebur | | 0.0 | 0.0 | 0.0 | 0.0 | 0.0 | |
| Jimsonweed | | 2.0 | 1.0 | 0.0 | 0.0 | 0.0 | |
| Lambsquarters, C | | 9.0 | 3.0 | 0.0 | 0.0 | 0.0 | |
| Morningglory Spp | | 0.0 | 0.0 | 0.0 | 0.0 | 0.0 | |
| Mustard, Wild | | 8.0 | 9.0 | 1.0 | 0.0 | 0.0 | |
| Pigweed, Redroot | | 9.0 | 6.0 | 0.0 | 0.0 | 0.0 | |
| Ragweed, Common | | 0.0 | 0.0 | 0.0 | 0.0 | 0.0 | |
| Velvetleaf | | 0.0 | 0.0 | 0.0 | 0.0 | 0.0 | |
| Barley, Unspecif | | 0.0 | 0.0 | 0.0 | 0.0 | 0.0 | |
| Corn, Field | | 0.0 | 0.0 | 0.0 | 0.0 | 0.0 | |
| Cotton | | 0.0 | 0.0 | 0.0 | 0.0 | 0.0 | |
| Rice, Upland | | 0.0 | 0.0 | 0.0 | 0.0 | 0.0 | |
| Soybean | | 0.0 | 0.0 | 0.0 | 0.0 | 0.0 | |
| Wheat, Spring, X | | 0.0 | 0.0 | 0.0 | 0.0 | 0.0 | |
| 3-[3-Chloro-4-(4-fluorophenethyloxy)phenyl]-1,1-dimethylurea | | | | | | | |
| Barnyardgrass | 5.0 | 2.0 | 0.0 | 0.0 | 0.0 | 0.0 | |
| Crabgrass, (Hair | 8.0 | 2.0 | 1.0 | 0.0 | 0.0 | 0.0 | |
| Foxtail, Green | 9.0 | 3.0 | 0.0 | 0.0 | 0.0 | 0.0 | |
| Oat, Wild | 0.0 | 0.0 | 0.0 | 0.0 | 0.0 | 0.0 | |
| Cocklebur | 0.0 | 0.0 | 0.0 | 0.0 | 0.0 | 0.0 | |
| Jimsonweed | 9.0 | 3.0 | 1.0 | 0.0 | 0.0 | 0.0 | |
| Lambsquarters, C | 9.0 | 9.0 | 9.0 | 7.0 | 2.0 | 0.0 | |
| Morningglory Spp | 0.0 | 0.0 | 0.0 | 0.0 | 0.0 | 0.0 | |
| Mustard, Wild | 9.0 | 9.0 | 6.0 | 6.0 | 3.0 | 0.0 | |
| Pigweed, Redroot | 9.0 | 9.0 | 9.0 | 9.0 | 4.0 | 0.0 | |
| Ragweed, Common | 3.0 | 3.0 | 0.0 | 0.0 | 0.0 | 0.0 | |
| Velvetleaf | 3.0 | 2.0 | 1.0 | 0.0 | 0.0 | 0.0 | |
| Corn, Field | 9.0 | 9.0 | 0.0 | 0.0 | 0.0 | 0.0 | |
| Cotton | 0.0 | 0.0 | 0.0 | 0.0 | 0.0 | 0.0 | |
| Rice, Upland | 1.0 | 0.0 | 0.0 | 0.0 | 0.0 | 0.0 | |

TABLE IV-continued

Evaluation of the Selective Preemergence Broadleaf Herbicidal Activity of the Compounds of the Invention in the Presence of Graminaceous Crops, Soybeans and Cotton
(Rates are given in kg/ha)

| Rate (kg/ha): | 2.000 | 1.000 | .500 | .250 | .125 | .063 | .032 |
|---|---|---|---|---|---|---|---|
| Sorghum, Grain | 0.0 | 0.0 | 0.0 | 0.0 | 0.0 | 0.0 | |
| Soybean | 2.0 | 1.0 | 0.0 | 0.0 | 0.0 | 0.0 | |
| Wheat, Spring, X | 1.0 | 0.0 | 0.0 | 0.0 | 0.0 | 0.0 | |

3-[3-Chloro-4-(β-methylphenethyloxy)phenyl]-1,1-dimethylurea

| | | | | | | | |
|---|---|---|---|---|---|---|---|
| Barnyardgrass | 0.0 | 0.5 | 0.0 | 0.0 | 0.0 | 0.0 | |
| Crabgrass, (Hair | 8.0 | 2.0 | 0.0 | 0.0 | 0.0 | 0.0 | |
| Foxtail, Green | 9.0 | 1.5 | 0.5 | 0.0 | 0.0 | 0.0 | |
| Nutsedge, Purple | 0.0 | 0.0 | 0.0 | 0.0 | 0.0 | 0.0 | |
| Oat, Wild | 0.0 | 0.0 | 0.0 | 0.0 | 0.0 | 0.0 | |
| Cocklebur | 4.5 | 0.0 | 0.0 | 0.0 | 0.0 | 0.0 | |
| Jimsonweed | 8.5 | 9.0 | 1.5 | 0.0 | 1.0 | 0.0 | |
| Lambsquarters, C | 9.0 | 9.0 | 9.0 | 6.0 | 4.5 | 0.0 | |
| Morningglory Spp | 5.0 | 4.5 | 0.0 | 0.0 | 0.0 | 0.0 | |
| Mustard, Wild | 9.0 | 9.0 | 9.0 | 8.5 | 6.0 | 5.0 | |
| Pigweed, Redroot | 9.0 | 9.0 | 9.0 | 9.0 | 2.0 | 0.0 | |
| Ragweed, Common | 6.0 | 1.5 | 0.0 | 0.0 | 0.0 | 0.0 | |
| Velvetleaf | 1.5 | 0.0 | 0.0 | 0.0 | 0.0 | 0.0 | |
| Barley, Unspecif | 0.0 | 0.0 | 0.0 | 0.0 | 0.0 | 0.0 | |
| Corn, Field | 4.5 | 4.5 | 0.0 | 0.0 | 0.0 | 0.0 | |
| Cotton | 0.0 | 0.0 | 0.0 | 0.0 | 0.0 | 0.0 | |
| Rice, Upland | 0.0 | 0.0 | 0.0 | 0.0 | 0.0 | 0.0 | |
| Sorghum, Grain | 0.0 | 0.0 | 0.0 | 0.0 | 0.0 | 0.0 | |
| Soybean | 0.0 | 0.0 | 0.0 | 0.0 | 0.0 | 0.0 | |
| Wheat, Spring, X | 0.0 | 0.0 | 0.0 | 0.0 | 0.0 | 0.0 | |

3-[3-Chloro-4-(4-chlorophenethyloxy)phenyl]-1,1-dimethylurea

| | | | | | | | |
|---|---|---|---|---|---|---|---|
| Barnyardgrass | 0.0 | 0.0 | 0.0 | 0.0 | 0.0 | 0.0 | |
| Crabgrass, (Hair | 1.0 | 0.0 | 0.0 | 0.0 | 0.0 | 0.0 | |
| Foxtail, Green | 3.0 | 1.0 | 0.0 | 0.0 | 0.0 | 0.0 | |
| Oat, Wild | 1.0 | 0.0 | 0.0 | 0.0 | 0.0 | 0.0 | |
| Jimsonweed | 2.0 | 0.0 | 0.0 | 0.0 | 0.0 | 0.0 | |
| Lambsquarters, C | 8.0 | 5.0 | 4.0 | 0.0 | 0.0 | 0.0 | |
| Morningglory Spp | 0.0 | 0.0 | 0.0 | 0.0 | 0.0 | 0.0 | |
| Mustard, Wild | 9.0 | 9.0 | 2.0 | 0.0 | 0.0 | 0.0 | |
| Pigweed, Redroot | 9.0 | 9.0 | 3.0 | 0.0 | 0.0 | 0.0 | |
| Ragweed, Common | 0.0 | 0.0 | 0.0 | 0.0 | 0.0 | 0.0 | |
| Velvetleaf | 1.0 | 0.0 | 0.0 | 0.0 | 0.0 | 0.0 | |
| Corn, Field | 0.0 | 0.0 | 0.0 | 0.0 | 0.0 | 0.0 | |
| Cotton | 0.0 | 0.0 | 0.0 | 0.0 | 0.0 | 0.0 | |
| Rice, Upland | 0.0 | 0.0 | 0.0 | 0.0 | 0.0 | 0.0 | |
| Sorghum, Grain | 0.0 | 0.0 | 0.0 | 0.0 | 0.0 | 0.0 | |
| Soybean | 0.0 | 0.0 | 0.0 | 0.0 | 0.0 | 0.0 | |
| Wheat, Spring, X | 0.0 | 0.0 | 0.0 | 0.0 | 0.0 | 0.0 | |

3-[3-Chloro-4-(α-methylphenethyloxy)phenyl]-1,1-dimethylurea

| | | | | | | | |
|---|---|---|---|---|---|---|---|
| Barnyardgrass | 0.0 | 0.0 | 0.0 | 0.0 | 0.0 | 0.0 | |
| Crabgrass, (Hair | 2.0 | 0.0 | 0.0 | 0.0 | 0.0 | 0.0 | |
| Foxtail, Green | 8.0 | 6.0 | 1.0 | 0.0 | 0.0 | 0.0 | |
| Oat, Wild | 1.0 | 0.0 | 0.0 | 0.0 | 0.0 | 0.0 | |
| Cocklebur | 0.0 | 0.0 | 0.0 | 0.0 | 0.0 | 0.0 | |
| Jimsonweed | 3.0 | 7.0 | 0.0 | 0.0 | 0.0 | 0.0 | |
| Lambsquarters, C | 9.0 | 9.0 | 9.0 | | 8.0 | 0.0 | |
| Morningglory, Spp | 0.0 | 0.0 | 0.0 | 0.0 | 0.0 | 0.0 | |
| Mustard, Wild | 9.0 | 9.0 | 9.0 | 3.0 | 1.0 | 0.0 | |
| Pigweed, Redroot | 9.0 | 9.0 | 9.0 | | 9.0 | 0.0 | |
| Ragweed, Common | 3.0 | 0.0 | 0.0 | 0.0 | 0.0 | 0.0 | |
| Velvetleaf | 0.0 | 0.0 | 0.0 | 0.0 | 0.0 | 0.0 | |
| Corn, Field | 0.0 | | | 0.0 | 0.0 | 0.0 | |
| Cotton | 0.0 | 0.0 | 0.0 | 0.0 | 0.0 | 0.0 | |
| Rice, Upland | 0.0 | 0.0 | 0.0 | 0.0 | 0.0 | 0.0 | |
| Sorghum, Grain | 0.0 | 0.0 | 0.0 | 0.0 | 0.0 | 0.0 | |
| Soybean | 0.0 | 0.0 | 0.0 | 0.0 | 0.0 | 0.0 | |
| Wheat, Spring, X | 0.0 | 0.0 | 0.0 | 0.0 | 0.0 | 0.0 | |

1-[3-Chloro-4-(phenethoxy)phenyl]-3-methylurea

| | | | | | | | |
|---|---|---|---|---|---|---|---|
| Barnyardgrass | 0.0 | 0.0 | 0.0 | 0.0 | 0.0 | 0.0 | |
| Foxtail, Green | 0.0 | 0.0 | 0.0 | 0.0 | 0.0 | 0.0 | |
| Nutsedge, Purple | 0.0 | 0.0 | 0.0 | 0.0 | 0.0 | 0.0 | |
| Oat, Wild | 0.0 | 0.0 | 0.0 | 0.0 | 0.0 | 0.0 | |
| Cocklebur | 0.0 | 0.0 | 0.0 | 0.0 | 0.0 | 0.0 | |
| Jimsonweed | 3.0 | 0.0 | 0.0 | 0.0 | 0.0 | 0.0 | |
| Lambsquarters, C | 9.0 | 9.0 | 9.0 | 9.0 | 8.0 | 6.0 | |
| Morningglory Spp | 1.0 | 0.0 | 0.0 | 0.0 | 0.0 | 0.0 | |
| Mustard, Wild | 9.0 | 9.0 | 6.0 | 0.0 | 0.0 | 0.0 | |
| Pigweed, Redroot | 8.0 | 8.0 | 8.0 | 0.0 | 0.0 | 0.0 | |
| Ragweed, Common | 0.0 | 0.0 | 0.0 | 0.0 | 0.0 | 0.0 | |
| Velvetleaf | 0.0 | 0.0 | 0.0 | 0.0 | 0.0 | 0.0 | |
| Barley, Unspecif | 0.0 | 0.0 | 0.0 | 0.0 | 0.0 | 0.0 | |
| Corn, Field | 0.0 | 0.0 | 0.0 | 0.0 | 0.0 | 0.0 | |
| Rice, Upland | 0.0 | 0.0 | 0.0 | 0.0 | 0.0 | 0.0 | |
| Sorghum, Grain | 0.0 | 0.0 | 0.0 | 0.0 | 0.0 | 0.0 | |
| Soybean | 0.0 | 0.0 | 0.0 | 0.0 | 0.0 | 0.0 | |
| Wheat, Spring, X | 0.0 | 0.0 | 0.0 | 0.0 | 0.0 | 0.0 | |

1,1-Dimethyl-3-[3-nitro-4-(3-phenylpropoxy)phenyl]urea

| | | | | | | | |
|---|---|---|---|---|---|---|---|
| Barnyardgrass | 0.0 | 0.0 | 0.0 | 0.0 | 0.0 | 0.0 | |
| Foxtail, Green | 0.0 | 0.0 | 0.0 | 0.0 | 0.0 | 0.0 | |
| Oat, Wild | 0.0 | 0.0 | 0.0 | 0.0 | 0.0 | 0.0 | |
| Jimsonweed | 0.0 | 0.0 | 0.0 | 0.0 | 0.0 | 0.0 | |
| Lambsquarters, C | 9.0 | 9.0 | 9.0 | 3.0 | 0.0 | 0.0 | |
| Morningglory Spp | 0.0 | 0.0 | 0.0 | 0.0 | 0.0 | 0.0 | |
| Mustard, Wild | 9.0 | 4.0 | 0.0 | 0.0 | 0.0 | 0.0 | |
| Pigweed, Redroot | 9.0 | 8.0 | 3.0 | 0.0 | 0.0 | 0.0 | |
| Ragweed, Common | 0.0 | 0.0 | 0.0 | 0.0 | 0.0 | 0.0 | |
| Velvetleaf | 0.0 | 0.0 | 0.0 | 0.0 | 0.0 | 0.0 | |
| Barley, Unspecif | 0.0 | 0.0 | 0.0 | 0.0 | 0.0 | 0.0 | |
| Corn, Field | 0.0 | 0.0 | 0.0 | 0.0 | 0.0 | 0.0 | |
| Rice, Upland | 0.0 | 0.0 | 0.0 | 0.0 | 0.0 | 0.0 | |
| Sorghum, Grain | 0.0 | 0.0 | 0.0 | 0.0 | 0.0 | 0.0 | |
| Soybean | 0.0 | 0.0 | 0.0 | 0.0 | 0.0 | 0.0 | |
| Wheat, Spring, X | 0.0 | 0.0 | 0.0 | 0.0 | 0.0 | 0.0 | |

1-[3-Chloro-4-(phenethyloxy)phenyl]-3-(2-ethoxyethyl)urea

| | | | | | | | |
|---|---|---|---|---|---|---|---|
| Barnyardgrass | 0.0 | 0.0 | 0.0 | 0.0 | 0.0 | 0.0 | |
| Foxtail, Green | 0.0 | 0.0 | 0.0 | 0.0 | 0.0 | 0.0 | |
| Nutsedge, Purple | 0.0 | 0.0 | 0.0 | 0.0 | 0.0 | 0.0 | |
| Oat, Wild | 0.0 | 0.0 | 0.0 | 0.0 | 0.0 | 0.0 | |
| Cocklebur | 0.0 | 0.0 | 0.0 | 0.0 | 0.0 | 0.0 | |
| Jimsonweed | 9.0 | 0.0 | 0.0 | 0.0 | 0.0 | 0.0 | |
| Lambsquarters, C | 9.0 | 9.0 | 3.0 | 0.0 | 0.0 | 0.0 | |
| Morningglory Spp | 0.0 | 0.0 | 0.0 | 0.0 | 0.0 | 0.0 | |
| Mustard, Wild | 9.0 | 9.0 | 9.0 | 9.0 | 9.0 | 9.0 | |
| Pigweed, Redroot | 2.0 | 1.0 | 0.0 | 0.0 | 0.0 | 0.0 | |
| Ragweed, Common | 0.0 | 0.0 | 0.0 | 0.0 | 0.0 | 0.0 | |
| Velvetleaf | 0.0 | 0.0 | 0.0 | 0.0 | 0.0 | 0.0 | |
| Barley, Unspecif | 0.0 | 0.0 | 0.0 | 0.0 | 0.0 | 0.0 | |
| Corn, Field | 0.0 | 0.0 | 0.0 | 0.0 | 0.0 | 0.0 | |
| Rice, Upland | 0.0 | 0.0 | 0.0 | 0.0 | 0.0 | 0.0 | |
| Sorghum, Grain | 0.0 | 0.0 | 0.0 | 0.0 | 0.0 | 0.0 | |
| Soybean | 0.0 | 0.0 | 0.0 | 0.0 | 0.0 | 0.0 | |
| Wheat, Spring, X | 0.0 | 0.0 | 0.0 | 0.0 | 0.0 | 0.0 | |

3'-Chloro-4'-phenethyloxy-4-morpholinecarboxanilide

| | | | | | | | |
|---|---|---|---|---|---|---|---|
| Barnyardgrass | 0.0 | 0.0 | 0.0 | 0.0 | 0.0 | 0.0 | |
| Foxtail, Green | 0.0 | 0.0 | 0.0 | 0.0 | 0.0 | 0.0 | |
| Nutsedge, Purple | 0.0 | 0.0 | 0.0 | 0.0 | 0.0 | 0.0 | |
| Oat, Wild | 0.0 | 0.0 | 0.0 | 0.0 | 0.0 | 0.0 | |
| Cocklebur | 0.0 | 0.0 | 0.0 | 0.0 | 0.0 | 0.0 | |
| Jimsonweed | 0.0 | 0.0 | 0.0 | 0.0 | 0.0 | 0.0 | |
| Lambsquarters, C | 9.0 | 9.0 | 9.0 | 6.0 | 9.0 | 9.0 | |
| Morningglory Spp | 4.0 | 0.0 | 0.0 | 0.0 | 0.0 | 0.0 | |
| Mustard, Wild | 9.0 | 9.0 | 0.0 | 0.0 | 0.0 | 0.0 | |
| Pigweed, Redroot | 9.0 | 9.0 | 9.0 | 0.0 | 0.0 | 0.0 | |
| Ragweed, Common | 0.0 | 0.0 | 0.0 | 0.0 | 0.0 | 0.0 | |
| Velvetleaf | 3.0 | 1.0 | 0.0 | 0.0 | 0.0 | 0.0 | |
| Barley, Unspecif | 0.0 | 0.0 | 0.0 | 0.0 | 0.0 | 0.0 | |
| Corn, Field | 0.0 | 0.0 | 0.0 | 0.0 | 0.0 | 0.0 | |
| Rice, Upland | 0.0 | 0.0 | 0.0 | 0.0 | 0.0 | 0.0 | |
| Sorghum, Grain | 0.0 | 0.0 | 0.0 | 0.0 | 0.0 | 0.0 | |
| Soybean | 0.0 | 0.0 | 0.0 | 0.0 | 0.0 | 0.0 | |
| Wheat, Spring, X | 0.0 | 0.0 | 0.0 | 0.0 | 0.0 | 0.0 | |

3-[3-Chloro-4-(4-methylphenethyloxy)phenyl]-1,1-dimethylurea

| | | | | | | | |
|---|---|---|---|---|---|---|---|
| Barnyardgrass | 0.0 | 0.0 | 0.0 | 0.0 | 0.0 | 0.0 | |
| Foxtail, Green | 0.0 | 0.0 | 0.0 | 0.0 | 0.0 | 0.0 | |
| Nutsedge, Purple | 0.0 | 0.0 | 0.0 | 0.0 | 0.0 | 0.0 | |
| Oat, Wild | 0.0 | 0.0 | 0.0 | 0.0 | 0.0 | 0.0 | |
| Cocklebur | 0.0 | 0.0 | 0.0 | 0.0 | 0.0 | 0.0 | |
| Jimsonweed | 9.0 | 0.0 | 0.0 | 0.0 | 0.0 | 0.0 | |

TABLE IV-continued

Evaluation of the Selective Preemergence Broadleaf Herbicidal Activity of the Compounds of the Invention in the Presence of Graminaceous Crops, Soybeans and Cotton
(Rates are given in kg/ha)

| Rate (kg/ha): | 2.000 | 1.000 | .500 | .250 | .125 | .063 | .032 |
|---|---|---|---|---|---|---|---|
| Lambsquarters, C | 9.0 | 9.0 | 9.0 | 7.0 | 0.0 | 0.0 | |
| Morningglory Spp | 0.0 | 0.0 | 0.0 | 0.0 | 0.0 | 0.0 | |
| Mustard, Wild | 9.0 | 9.0 | 9.0 | 0.0 | 0.0 | 0.0 | |
| Pigweed, Redroot | 9.0 | 9.0 | 0.0 | 0.0 | 0.0 | 0.0 | |
| Ragweed, Common | 3.0 | 0.0 | 0.0 | 0.0 | 0.0 | 0.0 | |
| Velvetleaf | 0.0 | 0.0 | 0.0 | 0.0 | 0.0 | 0.0 | |
| Barley, Unspecif | 0.0 | 0.0 | 0.0 | 0.0 | 0.0 | 0.0 | |
| Corn, Field | 0.0 | 0.0 | 0.0 | 0.0 | 0.0 | 0.0 | |
| Rice, Upland | 1.0 | 0.0 | 0.0 | 0.0 | 0.0 | 0.0 | |
| Sorghum, Grain | 0.0 | 0.0 | 0.0 | 0.0 | 0.0 | 0.0 | |
| Soybean | 0.0 | 0.0 | 0.0 | 0.0 | 0.0 | 0.0 | |
| Wheat, Spring, X | 0.0 | 0.0 | 0.0 | 0.0 | 0.0 | 0.0 | |

3-[3-Chloro-4-(4-methoxyphenethyloxy)phenyl]-1,1-dimethylurea

| | | | | | | | |
|---|---|---|---|---|---|---|---|
| Barnyardgrass | 0.0 | 0.0 | 0.0 | 0.0 | 0.0 | 0.0 | |
| Foxtail, Green | 0.0 | 0.0 | 0.0 | 0.0 | 0.0 | 0.0 | |
| Nutsedge, Purple | 0.0 | 0.0 | 0.0 | 0.0 | 0.0 | 0.0 | |
| Oat, Wild | 0.0 | 0.0 | 0.0 | 0.0 | 0.0 | 0.0 | |
| Cocklebur | 0.0 | 0.0 | 0.0 | 0.0 | 0.0 | 0.0 | |
| Jimsonweed | 0.0 | 0.0 | 0.0 | 0.0 | 0.0 | 0.0 | |
| Lambsquarters, C | 9.0 | 9.0 | 9.0 | 9.0 | 0.0 | 0.0 | |
| Morningglory Spp | 0.0 | 0.0 | 0.0 | 0.0 | 0.0 | 0.0 | |
| Mustard, Wild | 9.0 | 9.0 | 7.0 | 0.0 | 0.0 | 0.0 | |
| Pigweed, Redroot | 9.0 | 9.0 | 9.0 | 0.0 | 0.0 | 0.0 | |
| Ragweed, Common | 0.0 | 0.0 | 0.0 | 0.0 | 0.0 | 0.0 | |
| Velvetleaf | 0.0 | 0.0 | 0.0 | 0.0 | 0.0 | 0.0 | |
| Barley, Unspecif | 0.0 | 0.0 | 0.0 | 0.0 | 0.0 | 0.0 | |
| Corn, Field | 0.0 | 0.0 | 0.0 | 0.0 | 0.0 | 0.0 | |
| Rice, Upland | 1.0 | 0.0 | 0.0 | 0.0 | 0.0 | 0.0 | |
| Sorghum, Grain | 0.0 | 0.0 | 0.0 | 0.0 | 0.0 | 0.0 | |
| Soybean | 0.0 | 0.0 | 0.0 | 0.0 | 0.0 | 0.0 | |
| Wheat, Spring, X | 0.0 | 0.0 | 0.0 | 0.0 | 0.0 | 0.0 | |

1,1-Dimethyl-3-[3-nitro-4-(phenethyloxy)phenyl]urea

| | | | | | | | |
|---|---|---|---|---|---|---|---|
| Barnyardgrass | 4.0 | 0.0 | 0.0 | 0.0 | 0.0 | 0.0 | |
| Foxtail, Green | 6.0 | 0.0 | 0.0 | 0.0 | 0.0 | 0.0 | |
| Nutsedge, Purple | 0.0 | 0.0 | 0.0 | 0.0 | 0.0 | 0.0 | |
| Oat, Wild | 0.0 | 0.0 | 0.0 | 0.0 | 0.0 | 0.0 | |
| Cocklebur | 1.0 | 0.0 | 0.0 | 0.0 | 0.0 | 0.0 | |
| Jimsonweed | 9.0 | 0.0 | 0.0 | 0.0 | 0.0 | 0.0 | |
| Lambsquarters, C | 9.0 | 9.0 | 9.0 | 4.0 | 4.0 | 0.0 | |
| Morningglory Spp | 2.0 | 0.0 | 0.0 | 0.0 | 0.0 | 0.0 | |
| Mustard, Wild | 9.0 | 9.0 | 9.0 | 0.0 | 0.0 | 0.0 | |
| Pigweed, Redroot | 9.0 | 9.0 | 9.0 | 4.0 | 0.0 | 0.0 | |
| Ragweed, Common | 2.0 | 0.0 | 0.0 | 0.0 | 0.0 | 0.0 | |
| Velvetleaf | 0.0 | 0.0 | 0.0 | 0.0 | 0.0 | 0.0 | |
| Barley, Unspecif | 0.0 | 0.0 | 0.0 | 0.0 | 0.0 | 0.0 | |
| Corn, Field | 0.0 | 0.0 | 0.0 | 0.0 | 0.0 | 0.0 | |
| Rice, Upland | 0.0 | 0.0 | 0.0 | 0.0 | 0.0 | 0.0 | |
| Sorghum, Grain | 0.0 | 0.0 | 0.0 | 0.0 | 0.0 | 0.0 | |
| Soybean | 0.0 | 0.0 | 0.0 | 0.0 | 0.0 | 0.0 | |
| Wheat, Spring, X | 0.0 | 0.0 | 0.0 | 0.0 | 0.0 | 0.0 | |

3-{3-Chloro-4-[3-(4-methoxyphenyl)propoxy]phenyl}-1,1-dimethylurea

| | | | | | | | |
|---|---|---|---|---|---|---|---|
| Barnyardgrass | 0.0 | 0.0 | 0.0 | 0.0 | 0.0 | 0.0 | |
| Foxtail, Green | 0.0 | 0.0 | 0.0 | 0.0 | 0.0 | 0.0 | |
| Nutsedge, Purple | 0.0 | 0.0 | 0.0 | 0.0 | 0.0 | 0.0 | |
| Oat, Wild | 0.0 | 0.0 | 0.0 | 0.0 | 0.0 | 0.0 | |
| Cocklebur | 0.0 | 0.0 | 0.0 | 0.0 | 0.0 | 0.0 | |
| Jimsonweed | 0.0 | 0.0 | 0.0 | 0.0 | 0.0 | 0.0 | |
| Lambsquarters, C | 9.0 | 9.0 | 9.0 | 3.0 | 0.0 | 0.0 | |
| Morningglory Spp | 0.0 | 0.0 | 0.0 | 0.0 | 0.0 | 0.0 | |
| Mustard, Wild | 9.0 | 9.0 | 0.0 | 0.0 | 0.0 | 0.0 | |
| Pigweed, Redroot | 9.0 | 9.0 | 9.0 | 0.0 | 0.0 | 0.0 | |
| Ragweed, Common | 0.0 | 0.0 | 0.0 | 0.0 | 0.0 | 0.0 | |
| Velvetleaf | 0.0 | 0.0 | 0.0 | 0.0 | 0.0 | 0.0 | |
| Barley, Unspecif | 0.0 | 0.0 | 0.0 | 0.0 | 0.0 | 0.0 | |
| Corn, Field | 0.0 | 0.0 | 0.0 | 0.0 | 0.0 | 0.0 | |
| Rice, Upland | 0.0 | 0.0 | 0.0 | 0.0 | 0.0 | 0.0 | |
| Sorghum, Grain | 0.0 | 0.0 | 0.0 | 0.0 | 0.0 | 0.0 | |
| Soybean | 0.0 | 0.0 | 0.0 | 0.0 | 0.0 | 0.0 | |
| Wheat, Spring, X | 0.0 | 0.0 | 0.0 | 0.0 | 0.0 | 0.0 | |

3-[3-Chloro-4-(3-phenylbutoxy)phenyl]-1,1-dimethylurea

| | | | | | | | |
|---|---|---|---|---|---|---|---|
| Barnyardgrass | 0.0 | 0.0 | 0.0 | 0.0 | 0.0 | 0.0 | |
| Foxtail, Green | 7.0 | 0.0 | 0.0 | 0.0 | 0.0 | 0.0 | |
| Nutsedge, Purple | 0.0 | 0.0 | 0.0 | 0.0 | 0.0 | 0.0 | |
| Oat, Wild | 0.0 | 0.0 | 0.0 | 0.0 | 0.0 | 0.0 | |
| Cocklebur | 0.0 | 0.0 | 0.0 | 0.0 | 0.0 | 0.0 | |
| Jimsonweed | 9.0 | 0.0 | 0.0 | 0.0 | 0.0 | 0.0 | |
| Lambsquarters, C | 9.0 | 9.0 | 9.0 | 9.0 | 9.0 | 9.0 | |
| Morningglory Spp | 1.0 | 1.0 | 0.0 | 0.0 | 0.0 | 0.0 | |
| Mustard, Wild | 9.0 | 9.0 | 9.0 | 0.0 | 0.0 | 0.0 | |
| Pigweed, Redroot | 9.0 | 9.0 | 9.0 | 9.0 | 0.0 | 0.0 | |
| Ragweed, Common | 3.0 | 1.0 | 0.0 | 0.0 | 0.0 | 0.0 | |
| Velvetleaf | 9.0 | 0.0 | 0.0 | 0.0 | 0.0 | 0.0 | |
| Barley, Unspecif | 0.0 | 0.0 | 0.0 | 0.0 | 0.0 | 0.0 | |
| Corn, Field | 0.0 | 0.0 | 0.0 | 0.0 | 0.0 | 0.0 | |
| Rice, Upland | 0.0 | 0.0 | 0.0 | 0.0 | 0.0 | 0.0 | |
| Sorghum, Grain | 0.0 | 0.0 | 0.0 | 0.0 | 0.0 | 0.0 | |
| Soybean | 9.0 | 0.0 | 0.0 | 0.0 | 0.0 | 0.0 | |
| Wheat, Spring, X | 0.0 | 0.0 | 0.0 | 0.0 | 0.0 | 0.0 | |

3-[3-Chloro-4-(7-phenylheptyloxy)phenyl]-1,1-dimethylurea

| | | | | | | | |
|---|---|---|---|---|---|---|---|
| Barnyardgrass | 0.0 | 0.0 | 0.0 | 0.0 | 0.0 | 0.0 | |
| Foxtail, Green | 0.0 | 0.0 | 0.0 | 0.0 | 0.0 | 0.0 | |
| Nutsedge, Purple | 0.0 | 0.0 | 0.0 | 0.0 | 0.0 | 0.0 | |
| Oat, Wild | 0.0 | 0.0 | 0.0 | 0.0 | 0.0 | 0.0 | |
| Cocklebur | 0.0 | 0.0 | 0.0 | 0.0 | 0.0 | 0.0 | |
| Jimsonweed | 0.0 | 8.0 | | 0.0 | 0.0 | 0.0 | |
| Lambsquarters, C | 9.0 | 8.0 | | | | | |
| Morningglory Spp | 0.0 | 0.0 | 0.0 | 0.0 | 0.0 | 0.0 | |
| Mustard, Wild | 9.0 | 4.0 | 2.0 | 0.0 | 0.0 | 0.0 | |
| Pigweed, Redroot | 9.0 | 2.0 | 1.0 | 0.0 | 0.0 | 0.0 | |
| Ragweed, Common | 0.0 | 0.0 | 0.0 | 0.0 | 0.0 | 0.0 | |
| Velvetleaf | 0.0 | 0.0 | 0.0 | 0.0 | 0.0 | 0.0 | |
| Barley, Unspecif | 0.0 | 0.0 | 0.0 | 0.0 | 0.0 | 0.0 | |
| Corn, Field | 0.0 | 0.0 | 0.0 | 0.0 | 0.0 | 0.0 | |
| Rice, Upland | 0.0 | 0.0 | 0.0 | 0.0 | 0.0 | 0.0 | |
| Sorghum, Grain | 0.0 | 0.0 | 0.0 | 0.0 | 0.0 | 0.0 | |
| Soybean | 0.0 | 0.0 | 0.0 | 0.0 | 0.0 | 0.0 | |
| Wheat, Spring, X | 0.0 | 0.0 | 0.0 | 0.0 | 0.0 | 0.0 | |

3-[3-Chloro-4-(8-phenyloctyloxy)phenyl]-1,1-dimethylurea

| | | | | | | | |
|---|---|---|---|---|---|---|---|
| Barnyardgrass | 0.0 | 0.0 | 0.0 | 0.0 | 0.0 | 0.0 | |
| Foxtail, Green | 0.0 | 0.0 | 0.0 | 0.0 | 0.0 | 0.0 | |
| Nutsedge, Purple | 0.0 | 0.0 | 0.0 | 0.0 | 0.0 | 0.0 | |
| Oat, Wild | 0.0 | 0.0 | 0.0 | 0.0 | 0.0 | 0.0 | |
| Cocklebur | 0.0 | 0.0 | 0.0 | 0.0 | 0.0 | 0.0 | |
| Jimsonweed | 0.0 | 0.0 | 0.0 | 0.0 | 0.0 | 0.0 | |
| Lambsquarters, C | 6.0 | 5.0 | | 4.0 | 4.0 | 4.0 | |
| Morningglory Spp | 7.0 | 7.0 | 5.0 | 0.0 | 0.0 | 0.0 | |
| Mustard, Wild | 6.0 | | 3.0 | 0.0 | 0.0 | 0.0 | |
| Pigweed, Redroot | 6.0 | 5.0 | 3.0 | 0.0 | 0.0 | 0.0 | |
| Ragweed, Common | 0.0 | 0.0 | 0.0 | 0.0 | 0.0 | 0.0 | |
| Velvetleaf | 0.0 | 0.0 | 0.0 | 0.0 | 0.0 | 0.0 | |
| Barley, Unspecif | 0.0 | 0.0 | 0.0 | 0.0 | 0.0 | 0.0 | |
| Corn, Field | 0.0 | 0.0 | 0.0 | 0.0 | 0.0 | 0.0 | |
| Rice, Upland | 0.0 | 0.0 | 0.0 | 0.0 | 0.0 | 0.0 | |
| Sorghum, Grain | 0.0 | 0.0 | 0.0 | 0.0 | 0.0 | 0.0 | |
| Soybean | 0.0 | 0.0 | 0.0 | 0.0 | 0.0 | 0.0 | |
| Wheat, Spring, X | 0.0 | 0.0 | 0.0 | 0.0 | 0.0 | 0.0 | |

3-[3-Chloro-4-(1-methyl-3-phenylpropoxy)phenyl]-1,1-dimethylurea

| | | | | | | | |
|---|---|---|---|---|---|---|---|
| Barnyardgrass | 0.0 | 0.0 | 0.0 | 0.0 | 0.0 | 0.0 | |
| Foxtail, Green | 0.0 | 0.0 | 0.0 | 0.0 | 0.0 | 0.0 | |
| Nutsedge, Purple | 0.0 | 0.0 | 0.0 | 0.0 | 0.0 | 0.0 | |
| Oat, Wild | 0.0 | 0.0 | 0.0 | 0.0 | 0.0 | 0.0 | |
| Cocklebur | 0.0 | 0.0 | 0.0 | 0.0 | 0.0 | 0.0 | |
| Jimsonweed | 9.0 | 2.0 | 0.0 | 0.0 | 0.0 | 0.0 | |
| Lambsquarters, C | 9.0 | 9.0 | 9.0 | 9.0 | 0.0 | 0.0 | |
| Morningglory Spp | 2.0 | 0.0 | 0.0 | 0.0 | 0.0 | 0.0 | |
| Mustard, Wild | 9.0 | 7.0 | 0.0 | 0.0 | 0.0 | 0.0 | |
| Pigweed, Redroot | 9.0 | 9.0 | 0.0 | 0.0 | 0.0 | 0.0 | |
| Ragweed, Common | 7.0 | 0.0 | 0.0 | 0.0 | 0.0 | 0.0 | |
| Velvetleaf | 0.0 | 0.0 | 0.0 | 0.0 | 0.0 | 0.0 | |
| Barley, Unspecif | 0.0 | 0.0 | 0.0 | 0.0 | 0.0 | 0.0 | |
| Corn, Field | 0.0 | 0.0 | 0.0 | 0.0 | 0.0 | 0.0 | |
| Rice, Upland | 0.0 | 0.0 | 0.0 | 0.0 | 0.0 | 0.0 | |
| Sorghum, Grain | 0.0 | 0.0 | 0.0 | 0.0 | 0.0 | 0.0 | |

TABLE IV-continued

Evaluation of the Selective Preemergence Broadleaf Herbicidal Activity of the Compounds of the Invention in the Presence of Graminaceous Crops, Soybeans and Cotton
(Rates are given in kg/ha)

| Rate (kg/ha): | 2.000 | 1.000 | .500 | .250 | .125 | .063 | .032 |
|---|---|---|---|---|---|---|---|
| Soybean | 0.0 | 0.0 | 0.0 | 0.0 | 0.0 | 0.0 | |
| Wheat, Spring, X | 0.0 | 0.0 | 0.0 | 0.0 | 0.0 | 0.0 | |

3-[3-Chloro-4-(β-ethylphenethyloxy)phenyl]-1,1-dimethylurea

| | 2.000 | 1.000 | .500 | .250 | .125 | .063 |
|---|---|---|---|---|---|---|
| Barnyardgrass | 0.0 | 0.0 | 0.0 | 0.0 | 0.0 | 0.0 |
| Foxtail, Green | 0.0 | 0.0 | 0.0 | 0.0 | 0.0 | 0.0 |
| Nutsedge, Purple | 0.0 | 0.0 | 0.0 | 0.0 | 0.0 | 0.0 |
| Oat, Wild | 0.0 | 0.0 | 0.0 | 0.0 | 0.0 | 0.0 |
| Cocklebur | 0.0 | 0.0 | 0.0 | 0.0 | 0.0 | 0.0 |
| Jimsonweed | 7.0 | 1.0 | 0.0 | 0.0 | 0.0 | 0.0 |
| Lambsquarters, C | 9.0 | 9.0 | 9.0 | 9.0 | 0.0 | 0.0 |
| Morningglory Spp | 9.0 | 0.0 | 0.0 | 0.0 | 0.0 | 0.0 |
| Mustard, Wild | 9.0 | 9.0 | 9.0 | 3.0 | 0.0 | 0.0 |
| Pigweed, Redroot | 9.0 | 9.0 | 9.0 | 0.0 | 0.0 | 0.0 |
| Ragweed, Common | 2.0 | 0.0 | 0.0 | 0.0 | 0.0 | 0.0 |
| Velvetleaf | 2.0 | 0.0 | 0.0 | 0.0 | 0.0 | 0.0 |
| Barley, Unspecif | 0.0 | 0.0 | 0.0 | 0.0 | 0.0 | 0.0 |
| Corn, Field | 0.0 | 0.0 | 0.0 | 0.0 | 0.0 | 0.0 |
| Rice, Upland | 0.0 | 0.0 | 0.0 | 0.0 | 0.0 | 0.0 |
| Sorghum, Grain | 0.0 | 0.0 | 0.0 | 0.0 | 0.0 | 0.0 |
| Soybean | 0.0 | 0.0 | 0.0 | 0.0 | 0.0 | 0.0 |
| Wheat, Spring, X | 0.0 | 0.0 | 0.0 | 0.0 | 0.0 | 0.0 |

1-[3-Chloro-4-(phenethyloxy)phenyl]-3-ethylurea

| | 2.000 | 1.000 | .500 | .250 | .125 | .063 |
|---|---|---|---|---|---|---|
| Barnyardgrass | 0.0 | 0.0 | 0.0 | 0.0 | 0.0 | 0.0 |
| Foxtail, Green | 0.0 | 0.0 | 0.0 | 0.0 | 0.0 | 0.0 |
| Nutsedge, Purple | 0.0 | 0.0 | 0.0 | 0.0 | 0.0 | 0.0 |
| Oat, Wild | 0.0 | 0.0 | 0.0 | 0.0 | 0.0 | 0.0 |
| Cocklebur | 0.0 | 0.0 | 0.0 | 0.0 | 0.0 | 0.0 |
| Jimsonweed | 0.0 | 0.0 | 0.0 | 0.0 | 0.0 | 0.0 |
| Lambsquarters, C | 9.0 | 9.0 | | | | |
| Morningglory Spp | 0.0 | 0.0 | 0.0 | 0.0 | 0.0 | 0.0 |
| Mustard, Wild | 6.0 | 9.0 | 1.0 | 0.0 | 0.0 | 0.0 |
| Pigweed, Redroot | 9.0 | 8.0 | 3.0 | 0.0 | 0.0 | 0.0 |
| Ragweed, Common | 0.0 | 0.0 | 0.0 | 0.0 | 0.0 | 0.0 |
| Velvetleaf | 0.0 | 0.0 | 0.0 | 0.0 | 0.0 | 0.0 |
| Barley, Unspecif | 0.0 | 0.0 | 0.0 | 0.0 | 0.0 | 0.0 |
| Corn, Field | 0.0 | 0.0 | 0.0 | 0.0 | 0.0 | 0.0 |
| Rice, Upland | 0.0 | 0.0 | 0.0 | 0.0 | 0.0 | 0.0 |
| Sorghum, Grain | 0.0 | 0.0 | 0.0 | 0.0 | 0.0 | 0.0 |
| Soybean | 0.0 | 0.0 | 0.0 | 0.0 | 0.0 | 0.0 |
| Wheat, Spring, X | 0.0 | 0.0 | 0.0 | 0.0 | 0.0 | 0.0 |

3-[3-Chloro-4-(phenethyloxy)phenyl]-1,1-dimethyl-2-thiourea

| | 2.000 | 1.000 | .500 | .250 | .125 | .063 |
|---|---|---|---|---|---|---|
| Barnyardgrass | 0.0 | 0.0 | 0.0 | 0.0 | 0.0 | 0.0 |
| Foxtail, Green | 0.0 | 0.0 | 0.0 | 0.0 | 0.0 | 0.0 |
| Nutsedge, Purple | 0.0 | 0.0 | 0.0 | 0.0 | 0.0 | 0.0 |
| Oat, Wild | 0.0 | 0.0 | 0.0 | 0.0 | 0.0 | 0.0 |
| Cocklebur | 0.0 | 0.0 | 0.0 | 0.0 | 0.0 | 0.0 |
| Jimsonweed | 0.0 | 0.0 | 0.0 | 0.0 | 0.0 | 0.0 |
| Lambsquarters, C | 9.0 | 9.0 | 0.0 | 0.0 | 0.0 | 0.0 |
| Morningglory Spp | 0.0 | 0.0 | 0.0 | 0.0 | 0.0 | 0.0 |
| Mustard, Wild | 9.0 | 2.0 | 0.0 | 0.0 | 0.0 | 0.0 |
| Pigweed, Redroot | 9.0 | 9.0 | 9.0 | 0.0 | 0.0 | 0.0 |
| Ragweed, Common | 0.0 | 0.0 | 0.0 | 0.0 | 0.0 | 0.0 |
| Velvetleaf | 0.0 | 0.0 | 0.0 | 0.0 | 0.0 | 0.0 |
| Barley, Unspecif | 0.0 | 0.0 | 0.0 | 0.0 | 0.0 | 0.0 |
| Corn, Field | 0.0 | 0.0 | 0.0 | 0.0 | 0.0 | 0.0 |
| Rice, Upland | 0.0 | 0.0 | 0.0 | 0.0 | 0.0 | 0.0 |
| Sorghum, Grain | 0.0 | 0.0 | 0.0 | 0.0 | 0.0 | 0.0 |
| Soybean | 0.0 | 0.0 | 0.0 | 0.0 | 0.0 | 0.0 |
| Wheat, Spring, X | 0.0 | 0.0 | 0.0 | 0.0 | 0.0 | 0.0 |

3-{3-Chloro-4-[2-(2-naphthyl)ethoxy]phenyl}-1,1-dimethylurea

| | 2.000 | 1.000 | .500 | .250 | .125 | .063 |
|---|---|---|---|---|---|---|
| Barnyardgrass | 0.0 | 0.0 | 0.0 | 0.0 | 0.0 | 0.0 |
| Foxtail, Green | 0.0 | 0.0 | 0.0 | 0.0 | 0.0 | 0.0 |
| Nutsedge, Purple | 0.0 | 0.0 | 0.0 | 0.0 | 0.0 | 0.0 |
| Oat, Wild | 0.0 | 0.0 | 0.0 | 0.0 | 0.0 | 0.0 |
| Cocklebur | 0.0 | 0.0 | 0.0 | 0.0 | 0.0 | 0.0 |
| Jimsonweed | 9.0 | 0.0 | | | | |
| Lambsquarters, C | 9.0 | 9.0 | 9.0 | 8.0 | 0.0 | 0.0 |
| Morningglory Spp | 0.0 | 0.0 | 0.0 | 0.0 | 0.0 | 0.0 |
| Mustard, Wild | 9.0 | 9.0 | 9.0 | 9.0 | 0.0 | |
| Pigweed, Redroot | 8.0 | 8.0 | 0.0 | 0.0 | 0.0 | 0.0 |
| Ragweed, Common | 0.0 | 0.0 | 0.0 | 0.0 | 0.0 | 0.0 |
| Velvetleaf | 0.0 | 0.0 | 0.0 | 0.0 | 0.0 | 0.0 |
| Barley, Unspecif | 0.0 | 0.0 | 0.0 | 0.0 | 0.0 | 0.0 |
| Corn, Field | 0.0 | 0.0 | 0.0 | 0.0 | 0.0 | 0.0 |
| Rice, Upland | 0.0 | 0.0 | 0.0 | 0.0 | 0.0 | 0.0 |
| Sorghum, Grain | 0.0 | 0.0 | 0.0 | 0.0 | 0.0 | 0.0 |
| Soybean | 0.0 | 0.0 | 0.0 | 0.0 | 0.0 | 0.0 |
| Wheat, Spring, X | 0.0 | 0.0 | 0.0 | 0.0 | 0.0 | 0.0 |

3-{3-Chloro-4-[(3,4-dimethoxyphenethyl)oxy]phenyl}-1,1-dimethylurea

| | 2.000 | 1.000 | .500 | .250 | .125 | .063 |
|---|---|---|---|---|---|---|
| Barnyardgrass | 0.0 | 0.0 | 0.0 | 0.0 | 0.0 | 0.0 |
| Foxtail, Green | 2.0 | 2.0 | 0.0 | 0.0 | 0.0 | 0.0 |
| Nutsedge, Purple | 0.0 | 0.0 | 0.0 | 0.0 | 0.0 | 0.0 |
| Oat, Wild | 0.0 | 0.0 | 0.0 | 0.0 | 0.0 | 0.0 |
| Cocklebur | 0.0 | 0.0 | 0.0 | 0.0 | 0.0 | 0.0 |
| Jimsonweed | 9.0 | 9.0 | 9.0 | 9.0 | 9.0 | 9.0 |
| Lambsquarters, C | 9.0 | 9.0 | 9.0 | 8.0 | 0.0 | 0.0 |
| Morningglory Spp | 0.0 | 0.0 | 0.0 | 0.0 | 0.0 | 0.0 |
| Mustard, Wild | 9.0 | 9.0 | 9.0 | 9.0 | 9.0 | 9.0 |
| Pigweed, Redroot | 9.0 | 9.0 | 7.0 | 0.0 | 0.0 | 0.0 |
| Ragweed, Common | 0.0 | 0.0 | 0.0 | 0.0 | 0.0 | 0.0 |
| Velvetleaf | 0.0 | 0.0 | 0.0 | 0.0 | 0.0 | 0.0 |
| Barley, Unspecif | 0.0 | 0.0 | 0.0 | 0.0 | 0.0 | 0.0 |
| Corn, Field | 0.0 | 0.0 | 0.0 | 0.0 | 0.0 | 0.0 |
| Rice, Upland | 0.0 | 0.0 | 0.0 | 0.0 | 0.0 | 0.0 |
| Sorghum, Grain | 0.0 | 0.0 | 0.0 | 0.0 | 0.0 | 0.0 |
| Soybean | 0.0 | 0.0 | | 0.0 | 0.0 | 0.0 |
| Wheat, Spring, X | 0.0 | 0.0 | 0.0 | 0.0 | 0.0 | 0.0 |

1-[3-Chloro-4-(phenethyloxy)phenyl]-3-methyl-2-thiourea

| | 2.000 | 1.000 | .500 | .250 | .125 | .063 |
|---|---|---|---|---|---|---|
| Barnyardgrass | 0.0 | 0.0 | 0.0 | 0.0 | 0.0 | 0.0 |
| Foxtail, Green | 0.0 | 0.0 | 0.0 | 0.0 | 0.0 | 0.0 |
| Nutsedge, Purple | 0.0 | 0.0 | 0.0 | 0.0 | 0.0 | 0.0 |
| Oat, Wild | 0.0 | 0.0 | 0.0 | 0.0 | 0.0 | 0.0 |
| Cocklebur | 0.0 | 0.0 | 0.0 | 0.0 | 0.0 | 0.0 |
| Jimsonweed | 0.0 | 0.0 | 0.0 | 0.0 | 0.0 | 0.0 |
| Lambsquarters, C | 9.0 | 9.0 | 9.0 | 9.0 | 9.0 | 9.0 |
| Morningglory Spp | 0.0 | 0.0 | 0.0 | 0.0 | 0.0 | 0.0 |
| Mustard, Wild | 3.0 | 1.0 | 0.0 | 0.0 | 0.0 | 0.0 |
| Pigweed, Redroot | 7.0 | 0.0 | 0.0 | 0.0 | 0.0 | 0.0 |
| Ragweed, Common | 0.0 | 0.0 | 0.0 | 0.0 | 0.0 | 0.0 |
| Velvetleaf | 0.0 | 0.0 | 0.0 | 0.0 | 0.0 | 0.0 |
| Barley, Unspecif | 0.0 | 0.0 | 0.0 | 0.0 | 0.0 | 0.0 |
| Corn, Field | 0.0 | 0.0 | 0.0 | 0.0 | 0.0 | 0.0 |
| Rice, Upland | 0.0 | 0.0 | 0.0 | 0.0 | 0.0 | 0.0 |
| Sorghum, Grain | 0.0 | 0.0 | 0.0 | 0.0 | 0.0 | 0.0 |
| Soybean | 1.0 | 0.0 | 0.0 | 0.0 | 0.0 | 0.0 |
| Wheat, Spring, X | 0.0 | 0.0 | 0.0 | 0.0 | 0.0 | 0.0 |

3-[3-Amino-4-(phenethoxy)phenyl]-1,1-dimethylurea

| | 2.000 | 1.000 | .500 | .250 | .125 | .063 |
|---|---|---|---|---|---|---|
| Barnyardgrass | 0.0 | 0.0 | 0.0 | 0.0 | 0.0 | 0.0 |
| Foxtail, Green | 0.0 | 0.0 | 0.0 | 0.0 | 0.0 | 0.0 |
| Nutsedge, Purple | 0.0 | 0.0 | 0.0 | 0.0 | 0.0 | 0.0 |
| Oat, Wild | 0.0 | 0.0 | 0.0 | 0.0 | 0.0 | 0.0 |
| Cocklebur | 0.0 | 0.0 | 0.0 | 0.0 | 0.0 | 0.0 |
| Jimsonweed | | 0.0 | 0.0 | 0.0 | 0.0 | 0.0 |
| Lambsquarters, C | 9.0 | 0.0 | 0.0 | 0.0 | 0.0 | 0.0 |
| Morningglory Spp | 0.0 | 0.0 | 0.0 | 0.0 | 0.0 | 0.0 |
| Mustard, Wild | 9.0 | 0.0 | 0.0 | 0.0 | 0.0 | 0.0 |
| Pigweed, Redroot | 0.0 | 0.0 | 0.0 | 0.0 | 0.0 | 0.0 |
| Ragweed, Common | 0.0 | 0.0 | 0.0 | 0.0 | 0.0 | 0.0 |
| Velvetleaf | 0.0 | 0.0 | 0.0 | 0.0 | 0.0 | 0.0 |
| Barley, Unspecif | 0.0 | 0.0 | 0.0 | 0.0 | 0.0 | 0.0 |
| Corn, Field | 0.0 | 0.0 | 0.0 | 0.0 | 0.0 | 0.0 |
| Rice, Upland | 0.0 | 0.0 | 0.0 | 0.0 | 0.0 | 0.0 |
| Sorghum, Grain | 0.0 | 0.0 | 0.0 | 0.0 | 0.0 | 0.0 |
| Soybean | 0.0 | 0.0 | 0.0 | 0.0 | 0.0 | 0.0 |
| Wheat, Spring, X | 0.0 | 0.0 | 0.0 | 0.0 | 0.0 | 0.0 |

1-[3-Chloro-4-(phenethylthio)phenyl]-3-methylurea

| | 2.000 | 1.000 | .500 | .250 | .125 | .063 |
|---|---|---|---|---|---|---|
| Barnyardgrass | 0.0 | 0.0 | 0.0 | 0.0 | 0.0 | 0.0 |
| Foxtail, Green | 0.0 | 0.0 | 0.0 | 0.0 | 0.0 | 0.0 |
| Nutsedge, Purple | 0.0 | 0.0 | 0.0 | 0.0 | 0.0 | 0.0 |
| Oat, Wild | 0.0 | 0.0 | 0.0 | 0.0 | 0.0 | 0.0 |
| Cocklebur | 0.0 | 0.0 | 0.0 | 0.0 | 0.0 | 0.0 |

TABLE IV-continued

Evaluation of the Selective Preemergence Broadleaf Herbicidal Activity of the Compounds of the Invention in the Presence of Graminaceous Crops, Soybeans and Cotton
(Rates are given in kg/ha)

| Rate (kg/ha): | 2.000 | 1.000 | .500 | .250 | .125 | .063 | .032 |
|---|---|---|---|---|---|---|---|
| Jimsonweed | 8.0 | 0.0 | 0.0 | 0.0 | 0.0 | 0.0 | |
| Lambsquarters, C | 9.0 | 9.0 | 9.0 | 8.0 | 0.0 | 0.0 | |
| Morningglory Spp | 0.0 | 0.0 | 0.0 | 0.0 | 0.0 | 0.0 | |
| Mustard, Wild | 5.0 | 3.0 | 0.0 | 0.0 | 0.0 | 0.0 | |
| Pigweed, Redroot | 9.0 | 0.0 | 0.0 | 0.0 | 0.0 | 0.0 | |
| Ragweed, Common | 0.0 | 0.0 | 0.0 | 0.0 | 0.0 | 0.0 | |
| Velvetleaf | 0.0 | 0.0 | 0.0 | 0.0 | 0.0 | 0.0 | |
| Barley, Unspecif | 0.0 | 0.0 | 0.0 | 0.0 | 0.0 | 0.0 | |
| Corn, Field | 0.0 | 0.0 | 0.0 | 0.0 | 0.0 | 0.0 | |
| Rice, Upland | 1.0 | 0.0 | 0.0 | 0.0 | 0.0 | 0.0 | |
| Sorghum, Grain | 0.0 | 0.0 | 0.0 | 0.0 | 0.0 | 0.0 | |
| Soybean | 0.0 | 0.0 | 0.0 | 0.0 | 0.0 | 0.0 | |
| Wheat, Spring, X | 0.0 | 0.0 | 0.0 | 0.0 | 0.0 | 0.0 | |
| *1,1-Dimethyl-3-[4-(3-phenyl-2-propynyloxy)phenyl]urea* | | | | | | | |
| Barnyardgrass | 6.0 | 2.0 | 1.0 | 0.0 | 0.0 | 0.0 | |
| Foxtail, Green | 9.0 | 9.0 | 3.0 | 0.0 | 0.0 | 0.0 | |
| Nutsedge, Purple | 0.0 | 0.0 | 0.0 | 0.0 | 0.0 | 0.0 | |
| Oat, Wild | 3.0 | 1.0 | 0.0 | 0.0 | 0.0 | 0.0 | |
| Cocklebur | 3.0 | 3.0 | 1.0 | 0.0 | 0.0 | 0.0 | |
| Jimsonweed | 9.0 | 9.0 | 4.0 | | 0.0 | 0.0 | |
| Lambsquarters, C | 9.0 | 9.0 | 9.0 | 9.0 | 9.0 | 9.0 | |
| Morningglory Spp | 9.0 | 1.0 | 0.0 | 0.0 | 0.0 | 0.0 | |
| Mustard, Wild | 9.0 | 9.0 | 1.0 | 0.0 | 0.0 | 0.0 | |
| Pigweed, Redroot | 9.0 | 9.0 | 9.0 | 9.0 | 9.0 | 0.0 | |
| Ragweed, Common | 9.0 | 9.0 | 8.0 | 0.0 | 0.0 | 0.0 | |
| Velvetleaf | 1.0 | 0.0 | 0.0 | 0.0 | 0.0 | 0.0 | |
| Barley, Unspecif | 0.0 | 0.0 | 0.0 | 0.0 | 0.0 | 0.0 | |
| Corn, Field | 1.0 | 0.0 | 0.0 | 0.0 | 0.0 | 0.0 | |
| Rice, Upland | 1.0 | 0.0 | 0.0 | 0.0 | 0.0 | 0.0 | |
| Sorghum, Grain | 0.0 | 0.0 | 0.0 | 0.0 | 0.0 | 0.0 | |
| Soybean | 4.0 | 3.0 | 2.0 | 1.0 | 0.0 | 0.0 | |
| Wheat, Spring, X | 0.0 | 0.0 | 0.0 | 0.0 | 0.0 | 0.0 | |
| Sorghum, Grain | 1.0 | 1.0 | 0.0 | 0.0 | 0.0 | 0.0 | |
| Soybean | 7.0 | 3.0 | 1.0 | 0.0 | 0.0 | 0.0 | |
| Wheat, Spring, X | 2.0 | 0.0 | 0.0 | 0.0 | 0.0 | 0.0 | |
| *3-[3-Chloro-4-(α-ethylphenethyloxy)phenyl]-1,1-dimethylurea* | | | | | | | |
| Barnyardgrass | 1.0 | 1.0 | 0.0 | 0.0 | 0.0 | 0.0 | |
| Foxtail, Green | 0.0 | 0.0 | 0.0 | 0.0 | 0.0 | 0.0 | |
| Nutsedge, Purple | 0.0 | 0.0 | 0.0 | 0.0 | 0.0 | 0.0 | |
| Oat, Wild | 0.0 | 0.0 | 0.0 | 0.0 | 0.0 | 0.0 | |
| Cocklebur | 0.0 | 0.0 | 0.0 | 0.0 | 0.0 | 0.0 | |
| Jimsonweed | 9.0 | 1.0 | 0.0 | 0.0 | 0.0 | 0.0 | |
| Lambsquarters, C | 9.0 | 9.0 | 9.0 | 9.0 | 9.0 | 0.0 | |
| Morningglory Spp | 0.0 | 0.0 | 0.0 | 0.0 | 0.0 | 0.0 | |
| Mustard, Wild | 9.0 | 9.0 | 8.0 | 9.0 | 0.0 | 0.0 | |
| Pigweed, Redroot | 9.0 | 8.0 | 7.0 | 7.0 | 0.0 | 0.0 | |
| Ragweed, Common | 3.0 | 0.0 | 0.0 | 0.0 | 0.0 | 0.0 | |
| Velvetleaf | 0.0 | 0.0 | 0.0 | 0.0 | 0.0 | 0.0 | |
| Barley, Unspecif | 0.0 | 0.0 | 0.0 | 0.0 | 0.0 | 0.0 | |
| Corn, Field | 0.0 | 0.0 | 0.0 | 0.0 | 0.0 | 0.0 | |
| Rice, Upland | 0.0 | 0.0 | 0.0 | 0.0 | 0.0 | 0.0 | |
| Sorghum, Grain | 0.0 | 0.0 | 0.0 | 0.0 | 0.0 | 0.0 | |
| Soybean | 0.0 | 0.0 | 0.0 | 0.0 | 0.0 | 0.0 | |
| Wheat, Spring, X | 0.0 | 0.0 | 0.0 | 0.0 | 0.0 | 0.0 | |
| *1,1-Dimethyl-3-[4-(α-methylphenethyloxy)phenyl]urea* | | | | | | | |
| Barnyardgrass | 0.0 | 0.0 | 0.0 | 0.0 | 0.0 | 0.0 | |
| Foxtail, Green | 0.0 | 0.0 | 0.0 | 0.0 | 0.0 | 0.0 | |
| Nutsedge, Purple | 0.0 | 0.0 | 0.0 | 0.0 | 0.0 | 0.0 | |
| Oat, Wild | 0.0 | 0.0 | 0.0 | 0.0 | 0.0 | 0.0 | |
| Cocklebur | 0.0 | 0.0 | 0.0 | 0.0 | 0.0 | 0.0 | |
| Jimsonweed | 8.0 | 0.0 | 0.0 | 0.0 | 0.0 | 0.0 | |
| Lambsquarters, C | 9.0 | 9.0 | 8.0 | 6.0 | 3.0 | 3.0 | |
| Morningglory Spp | 2.0 | 0.0 | 0.0 | 0.0 | 0.0 | 0.0 | |
| Mustard, Wild | 9.0 | 9.0 | 6.0 | 0.0 | 0.0 | 0.0 | |
| Pigweed, Redroot | 9.0 | 9.0 | 8.0 | 0.0 | 0.0 | 0.0 | |
| Ragweed, Common | 0.0 | 0.0 | 0.0 | 0.0 | 0.0 | 0.0 | |
| Velvetleaf | 0.0 | 0.0 | 0.0 | 0.0 | 0.0 | 0.0 | |
| Barley, Unspecif | 0.0 | 0.0 | 0.0 | 0.0 | 0.0 | 0.0 | |
| Corn, Field | 0.0 | 0.0 | 0.0 | 0.0 | 0.0 | 0.0 | |
| Rice, Upland | 0.0 | 0.0 | 0.0 | 0.0 | 0.0 | 0.0 | |
| Sorghum, Grain | 0.0 | 0.0 | 0.0 | 0.0 | 0.0 | 0.0 | |
| Soybean | 0.0 | 0.0 | 0.0 | 0.0 | 0.0 | 0.0 | |
| Wheat, Spring, X | 0.0 | 0.0 | 0.0 | 0.0 | 0.0 | 0.0 | |
| *1-[3-Chloro-4-(phenethyloxy)phenyl]-1-formyl-3-methylurea* | | | | | | | |
| Barnyardgrass | 0.0 | 0.0 | 0.0 | 0.0 | 0.0 | 0.0 | |
| Foxtail, Green | 0.0 | 0.0 | 0.0 | 0.0 | 0.0 | 0.0 | |
| Nutsedge, Purple | 0.0 | 0.0 | 0.0 | 0.0 | 0.0 | 0.0 | |
| Oat, Wild | 0.0 | 0.0 | 0.0 | 0.0 | 0.0 | 0.0 | |
| Cocklebur | 9.0 | 1.0 | 0.0 | 0.0 | 0.0 | 0.0 | |
| Jimsonweed | 4.0 | 2.0 | 0.0 | 0.0 | 0.0 | 0.0 | |
| Lambsquarters, C | 9.0 | 9.0 | 9.0 | 9.0 | 9.0 | 9.0 | |
| Morningglory Spp | 4.0 | 2.0 | 1.0 | 0.0 | 0.0 | 0.0 | |
| Mustard, Wild | 9.0 | 9.0 | 9.0 | 7.0 | 7.0 | 0.0 | |
| Pigweed, Redroot | 9.0 | 9.0 | 9.0 | 9.0 | 7.0 | 0.0 | |
| Ragweed, Common | 4.0 | 0.0 | 0.0 | 0.0 | 0.0 | 0.0 | |
| Velvetleaf | 9.0 | 1.0 | 0.0 | 0.0 | 0.0 | 0.0 | |
| Barley, Unspecif | 0.0 | 0.0 | 0.0 | 0.0 | 0.0 | 0.0 | |
| Corn, Field | 0.0 | 0.0 | 0.0 | 0.0 | 0.0 | 0.0 | |
| Rice, Upland | 0.0 | 0.0 | 0.0 | 0.0 | 0.0 | 0.0 | |
| Sorghum, Grain | 0.0 | 0.0 | 0.0 | 0.0 | 0.0 | 0.0 | |
| Soybean | 3.0 | 0.0 | 0.0 | 0.0 | 0.0 | 0.0 | |
| Wheat, Spring, X | 0.0 | 0.0 | 0.0 | 0.0 | 0.0 | 0.0 | |
| *3-[4-(β-ethylphenethyloxy)phenyl]-1,1-dimethylurea* | | | | | | | |
| Barnyardgrass | 3.0 | 1.0 | 1.0 | 0.0 | 0.0 | 0.0 | |
| Foxtail, Green | 3.0 | 0.0 | 0.0 | 0.0 | 0.0 | 0.0 | |
| Nutsedge, Purple | 0.0 | 0.0 | 0.0 | 0.0 | 0.0 | 0.0 | |
| Oat, Wild | 0.0 | 0.0 | 0.0 | 0.0 | 0.0 | 0.0 | |
| Cocklebur | 0.0 | 0.0 | 0.0 | 0.0 | 0.0 | 0.0 | |
| Jimsonweed | 9.0 | 9.0 | 9.0 | 0.0 | 0.0 | 0.0 | |
| Lambsquarters, C | 9.0 | 9.0 | 6.0 | 4.0 | 0.0 | 0.0 | |
| Morningglory Spp | 0.0 | 0.0 | 0.0 | 0.0 | 0.0 | 0.0 | |
| Mustard, Wild | 9.0 | 9.0 | 9.0 | 0.0 | 0.0 | 0.0 | |
| Pigweed, Redroot | 9.0 | 9.0 | 9.0 | 3.0 | 0.0 | 0.0 | |
| Ragweed, Common | 0.0 | 0.0 | 0.0 | 0.0 | 0.0 | 0.0 | |
| Velvetleaf | 9.0 | 3.0 | 0.0 | 0.0 | 0.0 | 0.0 | |
| Barley, Unspecif | 0.0 | 0.0 | 0.0 | 0.0 | 0.0 | 0.0 | |
| Corn, Field | 0.0 | 0.0 | 0.0 | 0.0 | 0.0 | 0.0 | |
| Rice, Upland | 0.0 | 0.0 | 0.0 | 0.0 | 0.0 | 0.0 | |
| Sorghum, Grain | 0.0 | 0.0 | 0.0 | 0.0 | 0.0 | 0.0 | |
| Soybean | 0.0 | 0.0 | 0.0 | 0.0 | 0.0 | 0.0 | |
| Wheat, Spring, X | 0.0 | 0.0 | 0.0 | 0.0 | 0.0 | 0.0 | |
| *3-[3-Chloro-4-(phenethylsulfonyl)phenyl]-1,1-dimethylurea* | | | | | | | |
| Barnyardgrass | 0.0 | 0.0 | 0.0 | 0.0 | 0.0 | 0.0 | |
| Foxtail, Green | 0.0 | 0.0 | 0.0 | 0.0 | 0.0 | 0.0 | |
| Nutsedge, Purple | 0.0 | 0.0 | 0.0 | 0.0 | 0.0 | 0.0 | |
| Oat, Wild | 0.0 | 0.0 | 0.0 | 0.0 | 0.0 | 0.0 | |
| Cocklebur | 0.0 | 0.0 | 0.0 | 0.0 | 0.0 | 0.0 | |
| Jimsonweed | 9.0 | 0.0 | 0.0 | 0.0 | 0.0 | 0.0 | |
| Lambsquarters, C | 9.0 | 9.0 | 9.0 | 9.0 | 9.0 | 0.0 | |
| Morningglory Spp | 0.0 | 0.0 | 0.0 | 0.0 | 0.0 | 0.0 | |
| Mustard, Wild | 9.0 | 9.0 | 1.0 | 6.0 | 0.0 | 0.0 | |
| Pigweed, Redroot | 9.0 | 0.0 | 0.0 | 0.0 | 0.0 | 0.0 | |
| Ragweed, Common | 3.0 | 1.0 | 0.0 | 0.0 | 0.0 | 0.0 | |
| Velvetleaf | 0.0 | 0.0 | 0.0 | 0.0 | 0.0 | 0.0 | |
| Barley, Unspecif | 0.0 | 0.0 | 0.0 | 0.0 | 0.0 | 0.0 | |
| Corn, Field | 0.0 | 0.0 | 0.0 | 0.0 | 0.0 | 0.0 | |
| Rice, Upland | 0.0 | 0.0 | 0.0 | 0.0 | 0.0 | 0.0 | |
| Sorghum, Grain | 0.0 | 0.0 | 0.0 | 0.0 | 0.0 | 0.0 | |
| Soybean | 0.0 | 0.0 | 0.0 | 0.0 | 0.0 | 0.0 | |
| Wheat, Spring, X | 0.0 | 0.0 | 0.0 | 0.0 | 0.0 | 0.0 | |
| *1-[3-Chloro-4-(phenethyloxy)phenyl]-1,3,3-trimethylurea* | | | | | | | |
| Barnyardgrass | 0.0 | 0.0 | 0.0 | 0.0 | 0.0 | 0.0 | |
| Foxtail, Green | 0.0 | 0.0 | 0.0 | 0.0 | 0.0 | 0.0 | |
| Oat, Wild | 0.0 | 0.0 | 0.0 | 0.0 | 0.0 | 0.0 | |
| Cocklebur | 0.0 | 0.0 | 0.0 | 0.0 | 0.0 | 0.0 | |
| Jimsonweed | 9.0 | 9.0 | 9.0 | 9.0 | 9.0 | 9.0 | |
| Lambsquarters, C | 8.0 | 9.0 | 8.0 | 3.0 | 0.0 | 0.0 | |
| Morningglory Spp | 0.0 | 9.0 | 0.0 | 0.0 | 0.0 | 0.0 | |
| Mustard, Wild | 9.0 | 9.0 | 9.0 | 9.0 | 9.0 | 9.0 | |
| Pigweed, Redroot | 2.0 | 2.0 | 1.0 | 0.0 | 0.0 | 0.0 | |
| Ragweed, Common | 0.0 | 0.0 | 0.0 | 0.0 | 0.0 | 0.0 | |
| Velvetleaf | 0.0 | 0.0 | 0.0 | | | | |
| Barley, Unspecif | | 0.0 | 0.0 | | | | |
| Corn, Field | 0.0 | 0.0 | 0.0 | 0.0 | 0.0 | 0.0 | |

TABLE IV-continued
Evaluation of the Selective Preemergence Broadleaf Herbicidal Activity of the Compounds of the Invention in the Presence of Graminaceous Crops, Soybeans and Cotton
(Rates are given in kg/ha)

| Rate (kg/ha): | 2.000 | 1.000 | .500 | .250 | .125 | .063 | .032 |
|---|---|---|---|---|---|---|---|
| Rice, Upland | 0.0 | 0.0 | 0.0 | 0.0 | 0.0 | 0.0 | |
| Sorghum, Grain | 0.0 | 0.0 | 0.0 | 0.0 | 0.0 | 0.0 | |
| Soybean | 0.0 | 0.0 | 0.0 | 0.0 | 0.0 | 0.0 | |
| Wheat, Spring, X | 0.0 | 0.0 | 0.0 | 0.0 | 0.0 | | |

3-[3-Chloro-4-(phenethylthio)phenyl]-1,1-dimethylurea

| | 2.000 | 1.000 | .500 | .250 | .125 | .063 |
|---|---|---|---|---|---|---|
| Barnyardgrass | 0.0 | 0.0 | 0.0 | 0.0 | 0.0 | 0.0 |
| Foxtail, Green | 0.0 | 0.0 | 0.0 | 0.0 | 0.0 | 0.0 |
| Nutsedge, Purple | 0.0 | 0.0 | 0.0 | 0.0 | 0.0 | 0.0 |
| Oat, Wild | 0.0 | 0.0 | 0.0 | 0.0 | 0.0 | 0.0 |
| Cocklebur | 0.0 | 0.0 | 0.0 | 0.0 | 0.0 | 0.0 |
| Jimsonweed | 9.0 | 0.0 | 0.0 | 0.0 | 0.0 | 0.0 |
| Lambsquarters, C | 9.0 | 9.0 | 8.0 | 0.0 | 0.0 | 0.0 |
| Morningglory Spp | 0.0 | 0.0 | 0.0 | 0.0 | 0.0 | 0.0 |
| Mustard, Wild | 9.0 | 8.0 | 0.0 | 0.0 | 0.0 | 0.0 |
| Pigweed, Redroot | 9.0 | 3.0 | 2.0 | 0.0 | 0.0 | 0.0 |
| Ragweed, Common | 8.0 | 0.0 | 0.0 | 0.0 | 0.0 | 0.0 |
| Velvetleaf | 0.0 | 0.0 | 0.0 | 0.0 | 0.0 | 0.0 |
| Barley, Unspecif | 0.0 | 0.0 | 0.0 | 0.0 | 0.0 | 0.0 |
| Corn, Field | 0.0 | 0.0 | 0.0 | 0.0 | 0.0 | 0.0 |
| Rice, Upland | 0.0 | 0.0 | 0.0 | 0.0 | 0.0 | 0.0 |
| Sorghum, Grain | 0.0 | 0.0 | 0.0 | 0.0 | 0.0 | 0.0 |
| Soybean | 0.0 | 0.0 | 0.0 | 0.0 | 0.0 | 0.0 |
| Wheat, Spring, X | 0.0 | 0.0 | 0.0 | 0.0 | 0.0 | 0.0 |

1-[3-Chloro-4-(α-methylphenethyloxy)phenyl]-3-methylurea

| | 2.000 | 1.000 | .500 | .250 | .125 | .063 |
|---|---|---|---|---|---|---|
| Barnyardgrass | 0.0 | 0.0 | 0.0 | 0.0 | 0.0 | 0.0 |
| Foxtail, Green | 0.0 | 0.0 | 0.0 | 0.0 | 0.0 | 0.0 |
| Nutsedge, Purple | 0.0 | 0.0 | 0.0 | 0.0 | 0.0 | 0.0 |
| Oat, Wild | 0.0 | 0.0 | 0.0 | 0.0 | 0.0 | 0.0 |
| Cocklebur | 0.0 | 0.0 | 0.0 | 0.0 | 0.0 | 0.0 |
| Jimsonweed | 9.0 | 2.0 | 0.0 | 0.0 | 0.0 | 0.0 |
| Lambsquarters, C | 9.0 | 9.0 | 9.0 | 8.0 | 6.0 | 6.0 |
| Morningglory Spp | 2.0 | 0.0 | 0.0 | 0.0 | 0.0 | 0.0 |
| Mustard, Wild | 9.0 | 9.0 | 2.0 | 0.0 | 0.0 | 0.0 |
| Pigweed, Redroot | 9.0 | 9.0 | 9.0 | 0.0 | 0.0 | 0.0 |
| Ragweed, Common | 9.0 | 9.0 | 9.0 | 0.0 | 0.0 | 0.0 |
| Velvetleaf | 0.0 | 0.0 | 0.0 | 0.0 | 0.0 | 0.0 |
| Barley, Unspecif | 0.0 | 0.0 | 0.0 | 0.0 | 0.0 | 0.0 |
| Corn, Field | 0.0 | 0.0 | 0.0 | 0.0 | 0.0 | 0.0 |
| Rice, Upland | 0.0 | 0.0 | 0.0 | 0.0 | 0.0 | 0.0 |
| Sorghum, Grain | 0.0 | 0.0 | 0.0 | 0.0 | 0.0 | 0.0 |
| Soybean | 0.0 | 0.0 | 0.0 | 0.0 | 0.0 | 0.0 |
| Wheat, Spring, X | 0.0 | 0.0 | 0.0 | 0.0 | 0.0 | 0.0 |

3-[4-(α-ethylphenethyloxy)phenyl]-1,1-dimethylurea

| | 2.000 | 1.000 | .500 | .250 | .125 | .063 |
|---|---|---|---|---|---|---|
| Barnyardgrass | 0.0 | 0.0 | 0.0 | 0.0 | 0.0 | 0.0 |
| Foxtail, Green | 0.0 | 0.0 | 0.0 | 0.0 | 0.0 | 0.0 |
| Nutsedge, Purple | 0.0 | 0.0 | 0.0 | 0.0 | 0.0 | 0.0 |
| Oat, Wild | 0.0 | 0.0 | 0.0 | 0.0 | 0.0 | 0.0 |
| Cocklebur | 0.0 | 0.0 | 0.0 | 0.0 | 0.0 | 0.0 |
| Jimsonweed | 0.0 | 0.0 | 0.0 | 0.0 | 0.0 | 0.0 |
| Lambsquarters, C | 9.0 | 8.0 | 0.0 | 0.0 | 0.0 | 0.0 |
| Morningglory Spp | 0.0 | 0.0 | 0.0 | 0.0 | 0.0 | 0.0 |
| Mustard, Wild | 7.0 | 7.0 | 3.0 | 0.0 | 0.0 | 0.0 |
| Pigweed, Redroot | 0.0 | 0.0 | 0.0 | 0.0 | 0.0 | 0.0 |
| Ragweed, Common | 0.0 | 0.0 | 0.0 | 0.0 | 0.0 | 0.0 |
| Velvetleaf | 0.0 | 0.0 | 0.0 | 0.0 | 0.0 | 0.0 |
| Barley, Unspecif | 0.0 | 0.0 | 0.0 | 0.0 | 0.0 | 0.0 |
| Corn, Field | 0.0 | 0.0 | 0.0 | 0.0 | 0.0 | 0.0 |
| Rice, Upland | 0.0 | 0.0 | 0.0 | 0.0 | 0.0 | 0.0 |
| Sorghum, Grain | 0.0 | 0.0 | 0.0 | 0.0 | 0.0 | 0.0 |
| Soybean | 0.0 | 0.0 | 0.0 | 0.0 | 0.0 | 0.0 |
| Wheat, Spring, X | 0.0 | 0.0 | 0.0 | 0.0 | 0.0 | 0.0 |

1-[3-Chloro-4-(β-methylphenethyloxy)phenyl]-3-methylurea

| | 2.000 | 1.000 | .500 | .250 | .125 | .063 |
|---|---|---|---|---|---|---|
| Barnyardgrass | 3.0 | 0.0 | 0.0 | 0.0 | 0.0 | 0.0 |
| Foxtail, Green | 0.0 | 0.0 | 0.0 | 0.0 | 0.0 | 0.0 |
| Nutsedge, Purple | 0.0 | 0.0 | 0.0 | 0.0 | 0.0 | 0.0 |
| Oat, Wild | 0.0 | 0.0 | 0.0 | 0.0 | 0.0 | 0.0 |
| Cocklebur | 0.0 | 0.0 | 0.0 | 0.0 | 0.0 | 0.0 |
| Jimsonweed | 1.0 | 0.0 | 0.0 | 0.0 | 0.0 | 0.0 |
| Lambsquarters, C | 9.0 | 9.0 | 9.0 | 9.0 | 9.0 | 2.0 |
| Morningglory Spp | 0.0 | 0.0 | 0.0 | 0.0 | 0.0 | 0.0 |
| Mustard, Wild | 9.0 | 9.0 | 9.0 | 0.0 | 0.0 | 0.0 |
| Pigweed, Redroot | 9.0 | 9.0 | 9.0 | 3.0 | 0.0 | 0.0 |
| Ragweed, Common | 0.0 | 0.0 | 0.0 | 0.0 | 0.0 | 0.0 |
| Velvetleaf | 0.0 | 0.0 | 0.0 | 0.0 | 0.0 | 0.0 |
| Barley, Unspecif | 0.0 | 0.0 | 0.0 | 0.0 | 0.0 | 0.0 |
| Corn, Field | 0.0 | 0.0 | 0.0 | 0.0 | 0.0 | 0.0 |
| Rice, Upland | 0.0 | 0.0 | 0.0 | 0.0 | 0.0 | 0.0 |
| Sorghum, Grain | 0.0 | 0.0 | 0.0 | 0.0 | 0.0 | 0.0 |
| Soybean | 0.0 | 0.0 | 0.0 | 0.0 | 0.0 | 0.0 |
| Wheat, Spring, X | 0.0 | 0.0 | 0.0 | 0.0 | 0.0 | 0.0 |

1,1-Dimethyl-3-[4-(3-phenylpropoxy)-3-tolyl]urea

| | 2.000 | 1.000 | .500 | .250 | .125 | .063 |
|---|---|---|---|---|---|---|
| Barnyardgrass | 0.0 | 0.0 | 0.0 | 0.0 | 0.0 | 0.0 |
| Foxtail, Green | 0.0 | 0.0 | 0.0 | 0.0 | 0.0 | 0.0 |
| Nutsedge, Purple | 0.0 | 0.0 | 0.0 | 0.0 | 0.0 | 0.0 |
| Oat, Wild | 0.0 | 0.0 | 0.0 | 0.0 | 0.0 | 0.0 |
| Cocklebur | 0.0 | 0.0 | 0.0 | 0.0 | 0.0 | 0.0 |
| Jimsonweed | 0.0 | 0.0 | 0.0 | 0.0 | 0.0 | 0.0 |
| Lambsquarters, C | 9.0 | 9.0 | 9.0 | 8.0 | 8.0 | 0.0 |
| Morningglory Spp | 9.0 | 0.0 | 0.0 | 0.0 | 0.0 | 0.0 |
| Mustard, Wild | 9.0 | 9.0 | 4.0 | 3.0 | 0.0 | 0.0 |
| Pigweed, Redroot | 9.0 | 9.0 | 9.0 | 0.0 | 0.0 | 0.0 |
| Ragweed, Common | 0.0 | 0.0 | 0.0 | 0.0 | 0.0 | 0.0 |
| Velvetleaf | 0.0 | 0.0 | 0.0 | 0.0 | 0.0 | 0.0 |
| Barley, Unspecif | 0.0 | 0.0 | 0.0 | 0.0 | 0.0 | 0.0 |
| Corn, Field | 0.0 | 0.0 | 0.0 | 0.0 | 0.0 | 0.0 |
| Rice, Upland | 0.0 | 0.0 | 0.0 | 0.0 | 0.0 | 0.0 |
| Sorghum, Grain | 0.0 | 0.0 | 0.0 | 0.0 | 0.0 | 0.0 |
| Soybean | 1.0 | 0.0 | 0.0 | 0.0 | 0.0 | 0.0 |
| Wheat, Spring, X | 0.0 | 0.0 | 0.0 | 0.0 | 0.0 | 0.0 |

3'-Chloro-2,5-dimethyl-4'-phenethyloxy-1-pyrrolidinecarboxanilide

| | 2.000 | 1.000 | .500 | .250 | .125 | .063 |
|---|---|---|---|---|---|---|
| Barnyardgrass | 0.0 | 0.0 | 0.0 | 0.0 | 0.0 | 0.0 |
| Foxtail, Green | 0.0 | 0.0 | 0.0 | 0.0 | 0.0 | 0.0 |
| Nutsedge, Purple | 0.0 | 0.0 | 0.0 | 0.0 | 0.0 | 0.0 |
| Oat, Wild | 0.0 | 0.0 | 0.0 | 0.0 | 0.0 | 0.0 |
| Cocklebur | 0.0 | 0.0 | 0.0 | 0.0 | 0.0 | 0.0 |
| Jimsonweed | 0.0 | | 0.0 | 0.0 | 0.0 | 0.0 |
| Lambsquarters, C | 9.0 | 9.0 | 9.0 | | 0.0 | 0.0 |
| Morningglory Spp | 9.0 | 2.0 | 0.0 | 0.0 | 0.0 | 0.0 |
| Mustard, Wild | 9.0 | 9.0 | 0.0 | 0.0 | 0.0 | 0.0 |
| Pigweed, Redroot | 9.0 | 9.0 | 9.0 | 0.0 | 0.0 | 0.0 |
| Ragweed, Common | 0.0 | 0.0 | 0.0 | 0.0 | 0.0 | 0.0 |
| Velvetleaf | 0.0 | 0.0 | 0.0 | 0.0 | 0.0 | 0.0 |
| Barley, Unspecif | 0.0 | 0.0 | 0.0 | 0.0 | 0.0 | 0.0 |
| Corn, Field | 0.0 | 0.0 | 0.0 | 0.0 | 0.0 | 0.0 |
| Rice, Upland | 0.0 | 0.0 | 0.0 | 0.0 | 0.0 | 0.0 |
| Sorghum, Grain | 0.0 | 0.0 | 0.0 | 0.0 | 0.0 | 0.0 |
| Soybean | 0.0 | 0.0 | 0.0 | 0.0 | 0.0 | 0.0 |
| Wheat, Spring, X | 0.0 | 0.0 | 0.0 | 0.0 | 0.0 | 0.0 |

1-[3-Chloro-4-(phenethyloxy)phenyl]-3-(2-propynyl)urea

| | 2.000 | 1.000 | .500 | .250 | .125 | .063 |
|---|---|---|---|---|---|---|
| Barnyardgrass | 0.0 | 0.0 | 0.0 | 0.0 | 0.0 | 0.0 |
| Foxtail, Green | 0.0 | 0.0 | 0.0 | 0.0 | 0.0 | 0.0 |
| Nutsedge, Purple | 0.0 | 0.0 | 0.0 | 0.0 | 0.0 | 0.0 |
| Oat, Wild | 0.0 | 0.0 | 0.0 | 0.0 | 0.0 | 0.0 |
| Cocklebur | 0.0 | 0.0 | 0.0 | 0.0 | 0.0 | 0.0 |
| Jimsonweed | 2.0 | 0.0 | 0.0 | 0.0 | 0.0 | 0.0 |
| Lambsquarters, C | 9.0 | 9.0 | 9.0 | 9.0 | 0.0 | 0.0 |
| Morningglory Spp | 0.0 | 0.0 | 0.0 | 0.0 | 0.0 | 0.0 |
| Mustard, Wild | 3.0 | 1.0 | 0.0 | 0.0 | 0.0 | 0.0 |
| Pigweed, Redroot | 9.0 | 9.0 | 9.0 | 0.0 | 0.0 | 0.0 |
| Ragweed, Common | 0.0 | 0.0 | 0.0 | 0.0 | 0.0 | 0.0 |
| Velvetleaf | 0.0 | 0.0 | 0.0 | 0.0 | 0.0 | 0.0 |
| Barley, Unspecif | 0.0 | 0.0 | 0.0 | 0.0 | 0.0 | 0.0 |
| Corn, Field | 0.0 | 0.0 | 0.0 | 0.0 | 0.0 | 0.0 |
| Rice, Upland | 0.0 | 0.0 | 0.0 | 0.0 | 0.0 | 0.0 |
| Sorghum, Grain | 0.0 | 0.0 | 0.0 | 0.0 | 0.0 | 0.0 |
| Soybean | 0.0 | 0.0 | 0.0 | 0.0 | 0.0 | 0.0 |
| Wheat, Spring, X | 0.0 | 0.0 | 0.0 | 0.0 | 0.0 | 0.0 |

3-[3-Methoxy-4-(phenethyloxy)phenyl]-1,1-dimethylurea

| | 2.000 | 1.000 | .500 | .250 | .125 | .063 |
|---|---|---|---|---|---|---|
| Barnyardgrass | 1.0 | 1.0 | 0.0 | 0.0 | 0.0 | 0.0 |
| Foxtail, Green | 1.0 | 0.0 | 0.0 | 0.0 | 0.0 | 0.0 |
| Nutsedge, Purple | 0.0 | 0.0 | 0.0 | 0.0 | 0.0 | 0.0 |
| Oat, Wild | 0.0 | 0.0 | 0.0 | 0.0 | 0.0 | 0.0 |

TABLE IV-continued
Evaluation of the Selective Preemergence Broadleaf Herbicidal Activity of the Compounds of the Invention in the Presence of Gramineaceous Crops, Soybeans and Cotton
(Rates are given in kg/ha)

| Rate (kg/ha): | 2.000 | 1.000 | .500 | .250 | .125 | .063 | .032 |
|---|---|---|---|---|---|---|---|
| Cocklebur | 0.0 | 0.0 | 0.0 | 0.0 | 0.0 | 0.0 | |
| Jimsonweed | 7.0 | 7.0 | 9.0 | 0.0 | 0.0 | 0.0 | |
| Lambsquarters, C | 9.0 | 9.0 | 9.0 | 9.0 | 9.0 | 3.0 | |
| Morningglory Spp | 3.0 | 0.0 | 0.0 | 0.0 | 0.0 | 0.0 | |
| Mustard, Wild | 9.0 | 8.0 | 6.0 | 0.0 | 0.0 | 0.0 | |
| Pigweed, Redroot | 9.0 | 9.0 | 9.0 | 0.0 | 0.0 | 0.0 | |
| Ragweed, Common | 8.0 | 4.0 | 0.0 | 0.0 | 0.0 | 0.0 | |
| Velvetleaf | 0.0 | 0.0 | 0.0 | 0.0 | 0.0 | 0.0 | |
| Barley, Unspecif | 0.0 | 0.0 | 0.0 | 0.0 | 0.0 | 0.0 | |
| Corn, Field | 0.0 | 0.0 | 0.0 | 0.0 | 0.0 | 0.0 | |
| Rice, Upland | 0.0 | 0.0 | 0.0 | 0.0 | 0.0 | 0.0 | |
| Sorghum, Grain | 0.0 | 0.0 | 0.0 | 0.0 | 0.0 | 0.0 | |
| Soybean | 0.0 | 0.0 | 0.0 | 0.0 | 0.0 | 0.0 | |
| Wheat, Spring, X | 0.0 | 0.0 | 0.0 | 0.0 | 0.0 | 0.0 | |

3-{3-Chloro-4-[3-(2-phenyl-1,3-dioxolan-2-yl)propoxy]phenyl}-1,1-dimethylurea

| Barnyardgrass | 1.0 | 0.0 | 0.0 | 0.0 | 0.0 | 0.0 |
|---|---|---|---|---|---|---|
| Foxtail, Green | 0.0 | 0.0 | 0.0 | 0.0 | 0.0 | 0.0 |
| Nutsedge, Purple | 0.0 | 0.0 | 0.0 | 0.0 | 0.0 | 0.0 |
| Oat, Wild | 0.0 | 0.0 | 0.0 | 0.0 | 0.0 | 0.0 |
| Cocklebur | 0.0 | 0.0 | 0.0 | 0.0 | 0.0 | 0.0 |
| Jimsonweed | 9.0 | 9.0 | 9.0 | 9.0 | 9.0 | 9.0 |
| Lambsquarters, C | 9.0 | 9.0 | 9.0 | 7.0 | 4.0 | 3.0 |
| Morningglory Spp | 0.0 | 0.0 | 0.0 | 0.0 | 0.0 | 0.0 |
| Mustard, Wild | 9.0 | 9.0 | 9.0 | 0.0 | 0.0 | 0.0 |
| Pigweed, Redroot | 9.0 | 9.0 | 9.0 | 3.0 | 0.0 | 0.0 |
| Ragweed, Common | 0.0 | 0.0 | 0.0 | 0.0 | 0.0 | 0.0 |
| Velvetleaf | 0.0 | 0.0 | 0.0 | 0.0 | 0.0 | 0.0 |
| Barley, Unspecif | 0.0 | 0.0 | 0.0 | 0.0 | 0.0 | 0.0 |
| Corn, Field | 0.0 | 0.0 | 0.0 | 0.0 | 0.0 | 0.0 |
| Rice, Upland | 0.0 | 0.0 | 0.0 | 0.0 | 0.0 | 0.0 |
| Sorghum, Grain | 0.0 | 0.0 | 0.0 | 0.0 | 0.0 | 0.0 |
| Soybean | 0.0 | 0.0 | 0.0 | 0.0 | 0.0 | 0.0 |
| Wheat, Spring, X | 0.0 | 0.0 | 0.0 | 0.0 | 0.0 | 0.0 |

3-[4-(3-Benzoylpropoxy)-3-chlorophenyl-1,1-dimethylurea

| Barnyardgrass | 0.0 | 0.0 | 0.0 | 0.0 | 0.0 | 0.0 |
|---|---|---|---|---|---|---|
| Foxtail, Green | 0.0 | 0.0 | 0.0 | 0.0 | 0.0 | 0.0 |
| Nutsedge, Purple | 0.0 | 0.0 | 0.0 | 0.0 | 0.0 | 0.0 |
| Oat, Wild | 0.0 | 0.0 | 0.0 | 0.0 | 0.0 | 0.0 |
| Cocklebur | 2.0 | 0.0 | 0.0 | 0.0 | 0.0 | 0.0 |
| Lambsquarters, C | 9.0 | 6.0 | 6.0 | 1.0 | 0.0 | 0.0 |
| Morningglory Spp | 0.0 | 0.0 | 0.0 | 0.0 | 0.0 | 0.0 |
| Mustard, Wild | 9.0 | 8.0 | 0.0 | 0.0 | 0.0 | 0.0 |
| Pigweed, Redroot | 9.0 | 9.0 | 0.0 | 0.0 | 0.0 | 0.0 |
| Ragweed, Common | 0.0 | 0.0 | 0.0 | 0.0 | 0.0 | 0.0 |
| Velvetleaf | 0.0 | 0.0 | 0.0 | 0.0 | 0.0 | 0.0 |
| Barley, Unspecif | 1.0 | 0.0 | 0.0 | 0.0 | 0.0 | 0.0 |
| Corn, Field | 0.0 | 0.0 | 0.0 | 0.0 | 0.0 | 0.0 |
| Rice, Upland | 2.0 | 0.0 | 0.0 | 0.0 | 0.0 | 0.0 |
| Soybean | 1.0 | 1.0 | 0.0 | 0.0 | 0.0 | 0.0 |
| Wheat, Spring, X | 0.0 | 0.0 | 0.0 | 0.0 | 0.0 | 0.0 |

EXAMPLE 27

By the methods of Examples 1 to 4 (A to D) the following compounds are prepared:

3-[3-chloro-4-(cinnamyloxy)phenyl]-1,1-dimethylurea, m.p. 157.5°–158.5° C.;

3-[3-chloro-4-(p-fluorocinnamyloxy)phenyl]-1,1-dimethylurea, m.p. 154°–156° C.;

3-[p-(p-fluorocinnamyloxy)phenyl]-1,1-dimethylurea, m.p. 141°–144° C.;

3-[p-(cinnamyloxy)phenyl]-1,1-dimethylurea, m.p. 142°–144° C.;

3-[3-chloro-4-(p-methoxycinnamyloxy)phenyl]-1,1-dimethylurea) 145°–147° C.;

3-[3-chloro-4-(p-methylcinnamyloxy)phenyl]-1,1-dimethylurea, 152°–154° C.

We claim:

1. A compound of the formula:

wherein X is selected from the group consisting of O, S, and $SO_2$; Q is O; $R_1$ is H or CHO; $R_2$ is H or $C_1$–$C_4$ alkyl; W is selected from the group consisting of H, halogen, $C_1$–$C_4$ alkyl, $CF_3$, $OCH_3$, and $NO_2$; $R_3$ is selected from the group consisting of H, $C_1$–$C_4$ alkyl, $C_1$–$C_4$ alkyl monosubstituted with either $C_1$–$C_3$ alkoxy or halogen, $C_3$–$C_5$ alkenyl, $C_3$–$C_5$ alkynyl and CHO; A represents $C_2$–$C_3$ alkyl; Y is selected from the group consisting of H, halogen, $C_1$–$C_4$ alkyl, $OCH_3$ and $CF_3$; Z represents H, halogen, $C_1$–$C_4$ alkyl, or $C_1$–$C_4$ alkoxy.

2. A compound of the formula:

wherein X is O; Q is S; $R_1$ is H; $R_2$ is H or $C_1$–$C_4$ alkyl; $R_3$ is $C_1$–$C_4$ alkyl; A is $C_2$–$C_3$ alkyl; Y or Z is H or halogen; and W is H or halogen.

3. The compound according to claim 1, 3-[3-chloro-4-(phenethyloxy)-phenyl]-1,1-diethylurea.

4. The compound according to claim 1, 1-[3-chloro-4-(phenethyloxy)-phenyl]-3-methylurea.

5. The compound according to claim 1, 1,1-dimethyl-3-[3-nitro-4-(phenethyloxy)phenyl]urea.

6. The compound according to claim 1, 3-[3-chloro-4-(phenethyloxy)-phenyl]-1-ethyl-1-methylurea.

7. The compound according to claim 1, 3-[3-chloro-4-phenethyloxy)-phenyl]-1-ethylurea.

8. The compound according to claim 1, 1-[3-chloro-4-(β-methylphenethyloxy)phenyl]-3-methylurea.

9. The compound according to claim 1, 1,1-dimethyl-3-[3-nitro-4-(3-phenylpropoxy)phenyl]urea.

10. The compound according to claim 1, 1-[3-chloro-4-(phenethyloxy)phenyl]-3-(2-ethoxyethyl)urea.

11. The compound according to claim 2, 3-[3-chloro-4-(phenethyloxy)phenyl]-1,1-dimethyl-2-thiourea.

12. The compound according to claim 2, 1-[3-chloro-4-(phenethyloxy)phenyl]-3-methyl-2-thiourea.

13. The compound according to claim 1, 1-[3-chloro-4-(phenethylthio)phenyl]-3-methylurea.

14. The compound according to claim 1, 1-[3-chloro-4-(phenethyloxy)phenyl]-1-formyl-3-methylurea.

15. The compound according to claim 1, 3-[3-chloro-4-(phenethylsulfonyl)phenyl]-1,1-dimethylurea.

16. The compound according to claim 1, 1-[3-chloro-4-(α-methylphenethoxyloxy)phenyl]-3-methylurea.

17. The compound according to claim 1, 1-[3-chloro-4-(β-methylphenethyloxy)phenyl]-3-methylurea.

18. The compound according to claim 1, 1,1-dimethyl-3-[4-(3-phenylpropoxy)-3-tolyl]urea.

* * * * *

REEXAMINATION CERTIFICATE (331st)

United States Patent [19]

Spatz et al.

[11] B1 4,289,903

[45] Certificate Issued Apr. 2, 1985

[54] PARA-PHENYLALKOXY PHENYLUREA AND THIOUREA COMPOUNDS AND HERBICIDAL USE THEREOF

[75] Inventors: David M. Spatz, Trenton; Barrington Cross, Rocky Hill, both of N.J.

[73] Assignee: American Cyanamid Company, Stamford, Conn.

Reexamination Request:
No. 90/000,474, Nov. 30, 1983

Reexamination Certificate for:
Patent No.: 4,289,903
Issued: Sep. 15, 1981
Appl. No.: 51,584
Filed: Jun. 25, 1979

[51] Int. Cl.³ .............. C07C 127/15; C07C 127/17; A01N 7/00; A01N 17/08

[52] U.S. Cl. .............. 564/20; 564/27; 564/28; 564/49; 564/50; 564/51; 564/52; 564/53; 564/29; 260/465 E; 260/340.9 R; 71/88; 71/99; 71/105; 71/107; 71/119; 71/120; 560/11; 560/13; 560/16; 560/18; 560/39; 560/251; 560/138; 560/22

[58] Field of Search .............. 564/27-29, 564/49, 50, 51-53

[56] References Cited

U.S. PATENT DOCUMENTS

| | | | |
|---|---|---|---|
| 3,125,601 | 3/1964 | Goebel | 564/53 X |
| 3,326,663 | 6/1967 | Soloway | 564/50 X |
| 3,655,755 | 4/1972 | Olin | 564/214 |
| 3,819,697 | 6/1974 | Cross et al. | 564/49 X |
| 4,221,817 | 9/1980 | Tenne | 424/322 |
| 4,249,938 | 2/1981 | Takemoto et al. | 71/98 |

FOREIGN PATENT DOCUMENTS

1232748 of 1971 United Kingdom

*Primary Examiner*—Robert V. Hines

[57] ABSTRACT

There are provided certain p-phenylalkoxy phenylurea and thiourea compounds useful for the control of undesirable plants in the presence of agronomic crops and to methods for the preparation of said phenylalkoxy phenylurea and thiourea compounds.

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-18 are cancelled.

* * * * *